United States Patent
Wallisch et al.

(10) Patent No.: US 12,134,657 B2
(45) Date of Patent: Nov. 5, 2024

(54) THERAPEUTIC FACTOR XII ANTIBODY

(71) Applicants: Oregon Health & Science University, Portland, OR (US); Aronora, Inc., Portland, OR (US)

(72) Inventors: Michael Wallisch, Portland, OR (US); Andras Gruber, Portland, OR (US); Erik I. Tucker, Portland, OR (US); Christina U. Lorentz, Portland, OR (US)

(73) Assignees: Oregon Health & Science University, Portland, OR (US); Aronora, Inc., Portland, OR (US)

( * ) Notice: Subject to any disclaimer, the term of this patent is extended or adjusted under 35 U.S.C. 154(b) by 813 days.

(21) Appl. No.: 17/297,967

(22) PCT Filed: Nov. 27, 2019

(86) PCT No.: PCT/US2019/063729
§ 371 (c)(1),
(2) Date: May 27, 2021

(87) PCT Pub. No.: WO2020/113084
PCT Pub. Date: Jun. 4, 2020

(65) Prior Publication Data
US 2022/0089776 A1    Mar. 24, 2022

Related U.S. Application Data

(60) Provisional application No. 62/772,235, filed on Nov. 28, 2018.

(51) Int. Cl.
| | | |
|---|---|---|
| C07K 16/36 | (2006.01) |
| A61K 39/00 | (2006.01) |
| A61K 39/395 | (2006.01) |
| A61K 45/06 | (2006.01) |
| A61K 49/00 | (2006.01) |
| A61P 7/02 | (2006.01) |

(52) U.S. Cl.
CPC .......... *C07K 16/36* (2013.01); *A61K 39/3955* (2013.01); *A61K 45/06* (2013.01); *A61K 49/0002* (2013.01); *A61P 7/02* (2018.01); *A61K 39/00* (2013.01); *A61K 2039/545* (2013.01); *C07K 2317/51* (2013.01); *C07K 2317/515* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | |
|---|---|---|
| 9,574,013 B2 | 2/2017 | Gruber et al. |
| 2008/0254039 A1 | 10/2008 | Nieswandt et al. |
| 2015/0315292 A1 | 11/2015 | Gruber et al. |
| 2017/0114119 A1* | 4/2017 | Kleinschnitz .......... A61K 47/50 |

FOREIGN PATENT DOCUMENTS

| | | | |
|---|---|---|---|
| CN | 101102819 | 1/2008 | |
| WO | WO 2003/013423 | 2/2003 | |
| WO | WO 2013/014092 | 1/2013 | |
| WO | WO-2013014092 A1 * | 1/2013 | ......... A61K 39/3955 |
| WO | WO 2014/089493 | 6/2014 | |

OTHER PUBLICATIONS

Zilberman-Rudenko et al. Factor XII Activation Promotes Platelet Consumption in the Presence of Bacterial-Type Long-Chain Polyphosphate In Vitro and In Vivo. Arterioscler Thromb Vasc Biol. 2018; 38:1748-1760. (Year: 2018).*
AHA/ASA Journals Research Guidelines; Research Materials Availability. 2024 (Year: 2024).*
International Search Report and Written Opinion for PCT/US2019/063729, mailed Mar. 11, 2020 (19 pages).
Kenne et al., "Factor XII: A Drug Target for Safe Interference with Thrombosis and Inflammation," *Drug Discov. Today*, vol. 19:1459-1464, 2014.
Pathak et al., "Coagulation Factor XII Protease Domain Crystal Structure," *J. Thromb. Haemost.*, vol. 13:580-591, 2015.
Pixley et al., "A Monoclonal Antibody Recognizing an Icosapeptide Sequence in the Heavy Chain of Human Factor XII Inhibits Surface-catalyzed Activation," *J. Biol. Chem.*, vol. 262:10140-10145, 1987.
Saito et al., "Production and Characterization of a Murine Monoclonal Antibody Against a Heavy Chain of Hageman Factor (Factor XII)," *Blood*, vol. 65:1263-1268, 1985.
Wallisch et al., "Antibody inhibition of contact factor FXII reduces platelet deposition in a model of extracorporeal membrane oxygenator perfusion in nonhuman primates," *Res Pract Thromb Haemost*, vol. 4:205-216, 2020.
Zilberman-Rudenko et al., "Factor XII Activation Promotes Platelet Consumption in the Presence of Bacterial-Type Long-Chain Polyphosphate In Vitro and In Vivo," *Arterioscler. Thromb. Vasc. Biol.*, vol. 38:1748-1760, 2018.
Gu et al., "Anticoagulant thrombolytic mechanism of anticoagulant proteins," Chinese Bulletin of Life Sciences 22(8):755-760, 2010 (in Japanese with English machine translation).

* cited by examiner

*Primary Examiner* — Daniel E Kolker
*Assistant Examiner* — Maureen Varina Driscoll
(74) *Attorney, Agent, or Firm* — Klarquist Sparkman, LLP

(57) ABSTRACT

Monoclonal antibodies that bind, such as specifically bind, blood protein factor XII (FXII) are described. The monoclonal antibodies (including antigen-binding fragments thereof) are capable of forming immune complexes with human FXII and inhibiting FXII activity, resulting in safe anti-inflammatory and anti-thrombotic effects.

21 Claims, 23 Drawing Sheets

Specification includes a Sequence Listing.

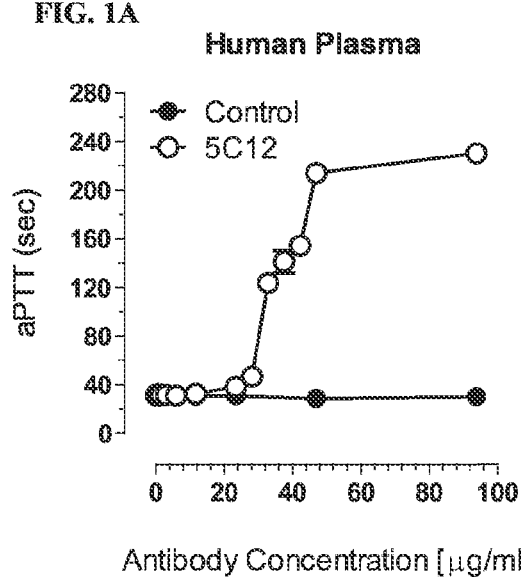
FIG. 1A Human Plasma
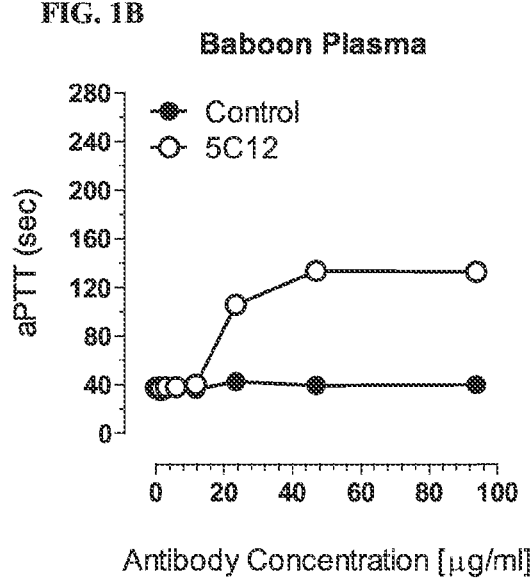
FIG. 1B Baboon Plasma
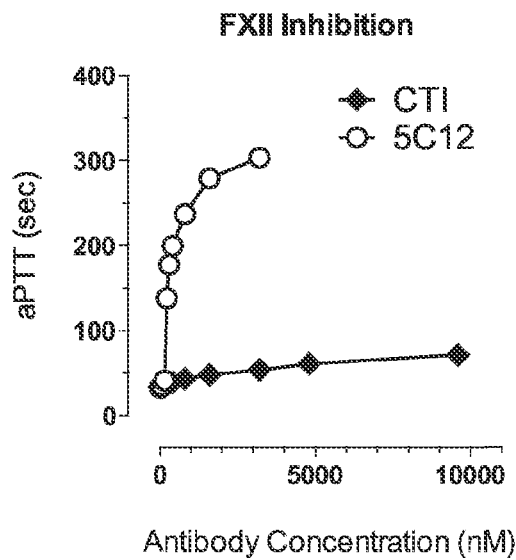
FIG. 1C FXII Inhibition

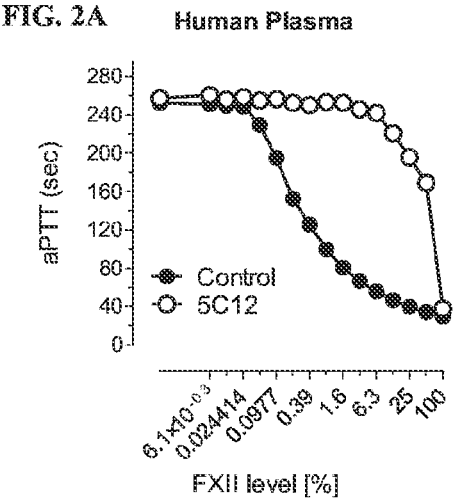
FIG. 2A  Human Plasma
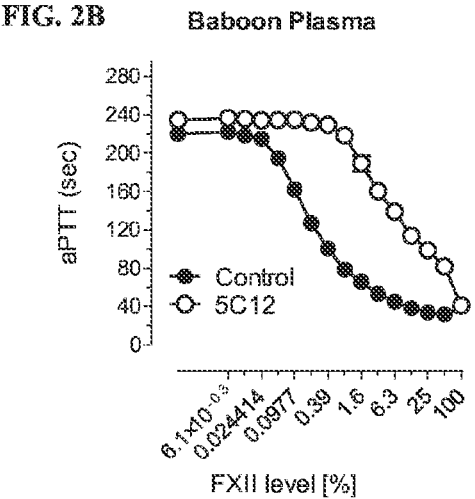
FIG. 2B  Baboon Plasma
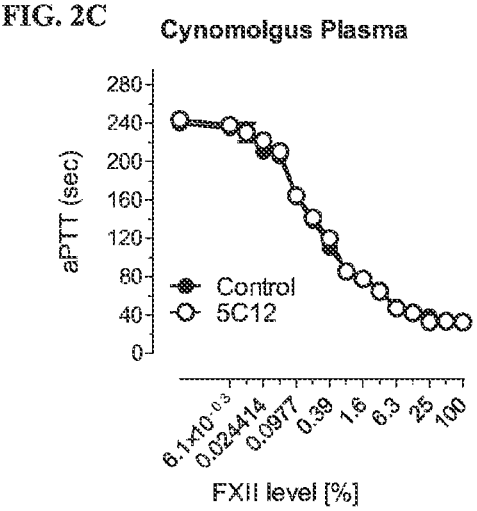
FIG. 2C  Cynomolgus Plasma
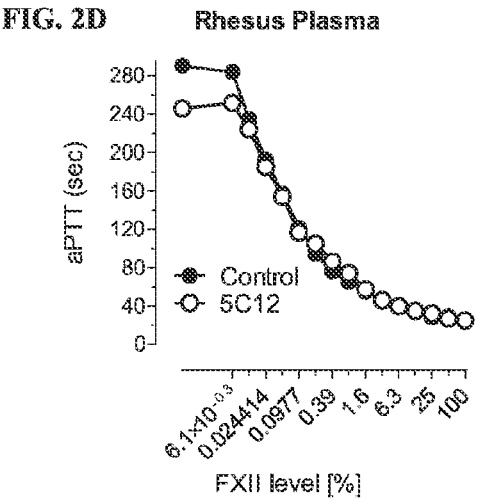
FIG. 2D  Rhesus Plasma
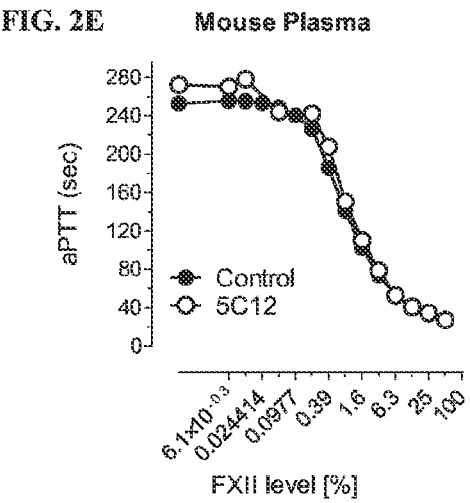
FIG. 2E  Mouse Plasma
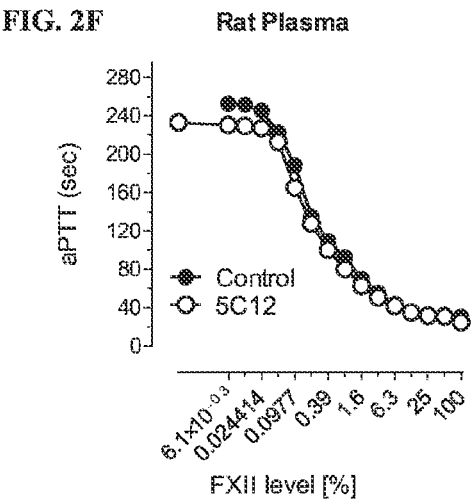
FIG. 2F  Rat Plasma

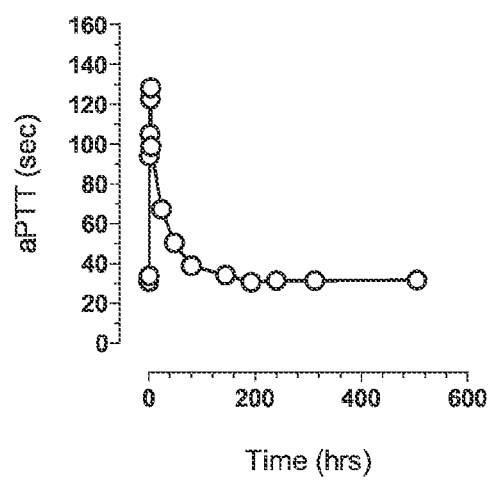
FIG. 5A aPTT
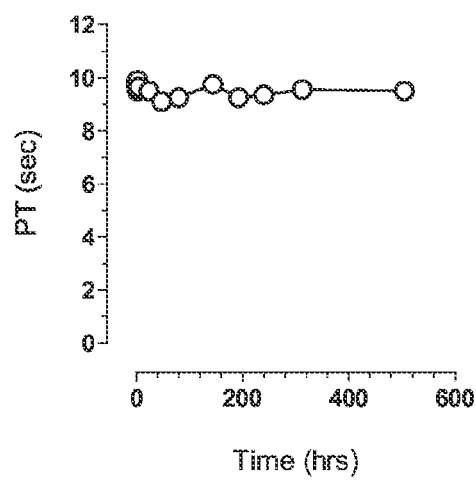
FIG. 5B PT
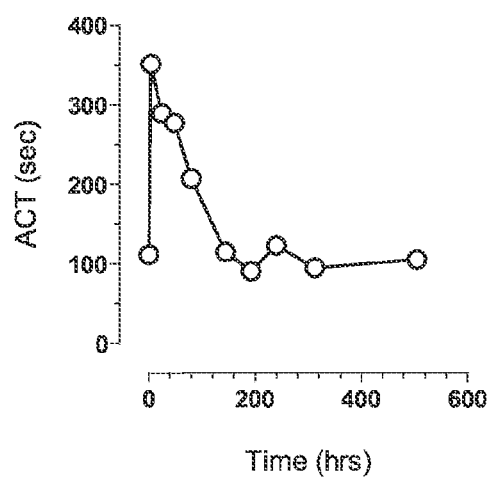
FIG. 5C ACT
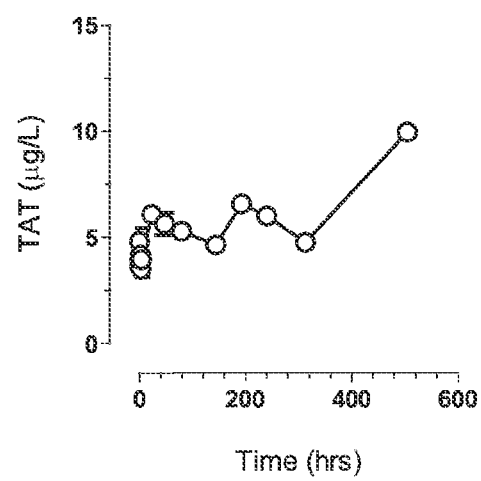
FIG. 5D TAT

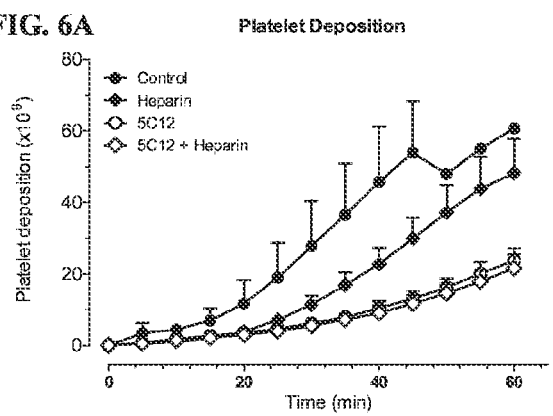
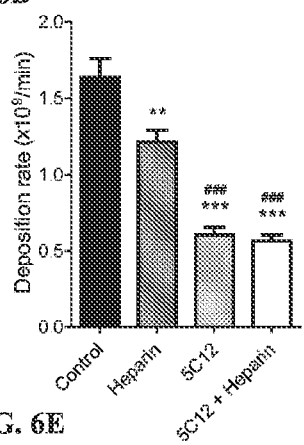
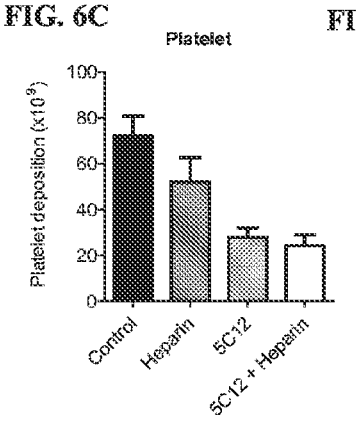
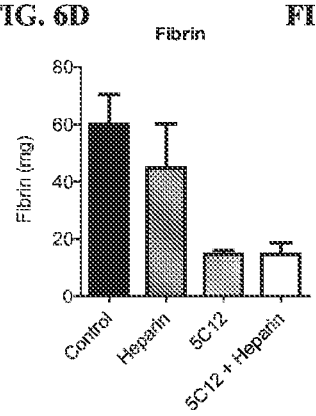
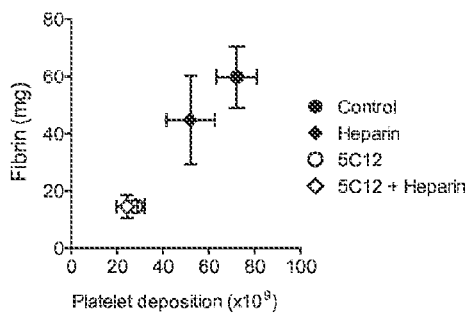

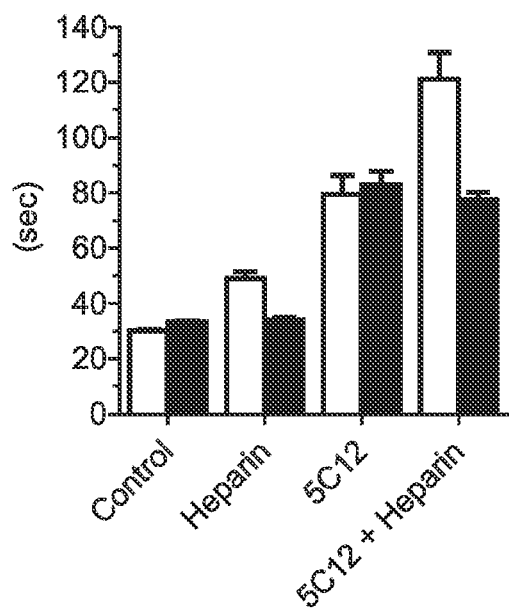
FIG. 7A aPTT
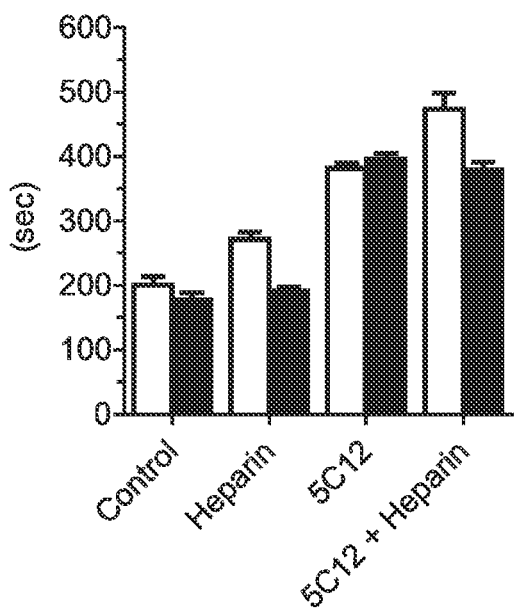
FIG. 7B ACT
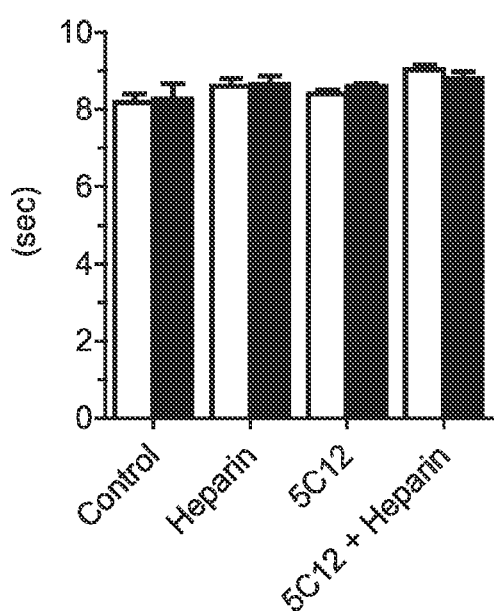
FIG. 7C PT

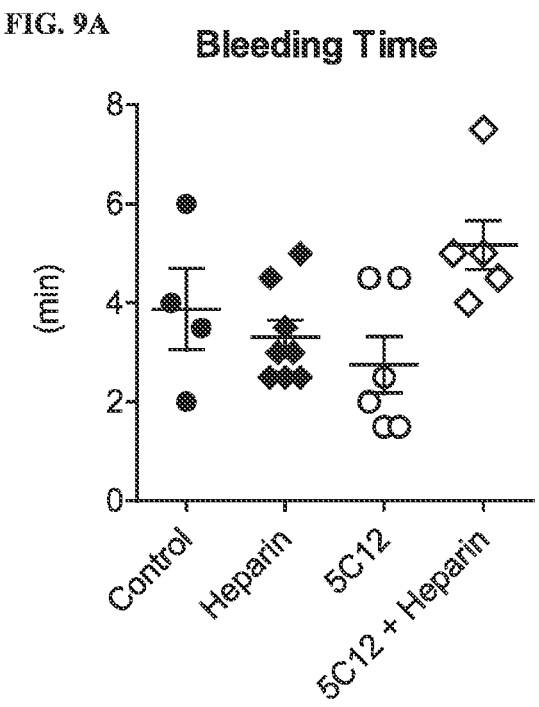
FIG. 9A Bleeding Time
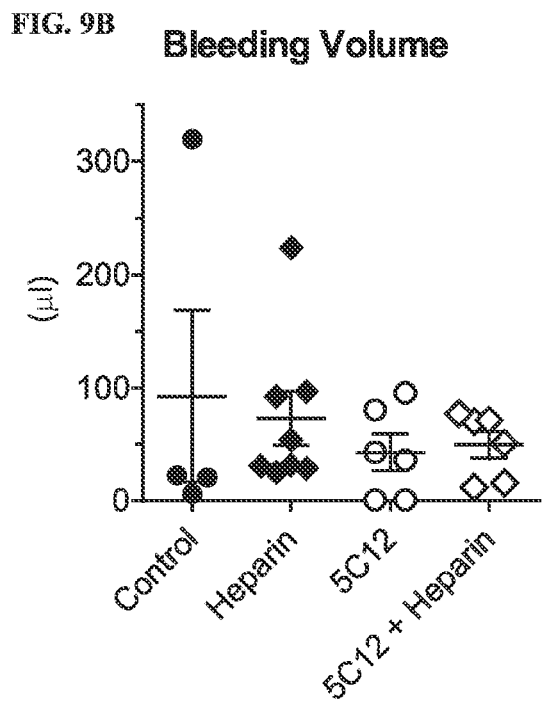
FIG. 9B Bleeding Volume
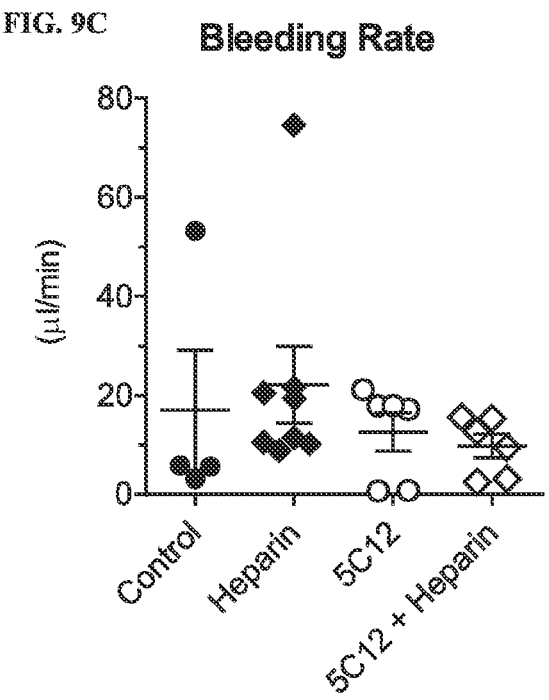
FIG. 9C Bleeding Rate

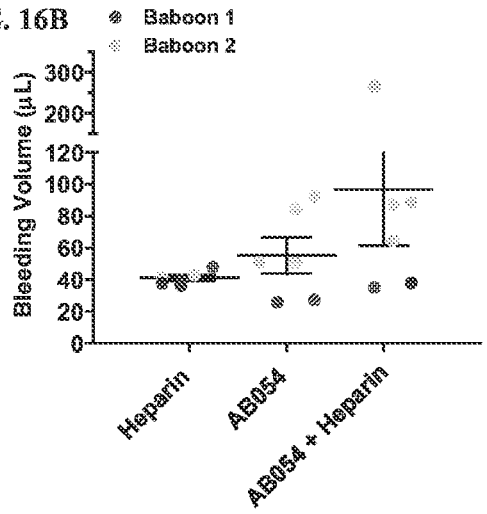
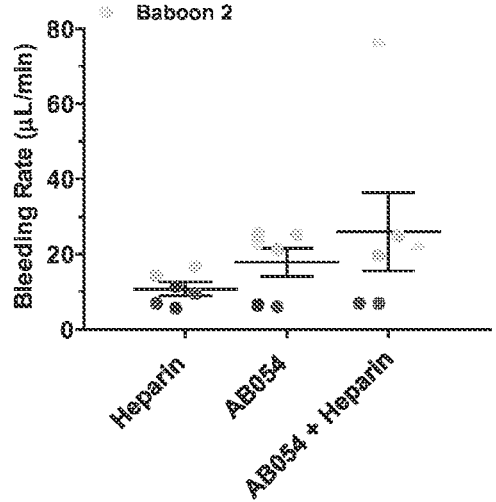
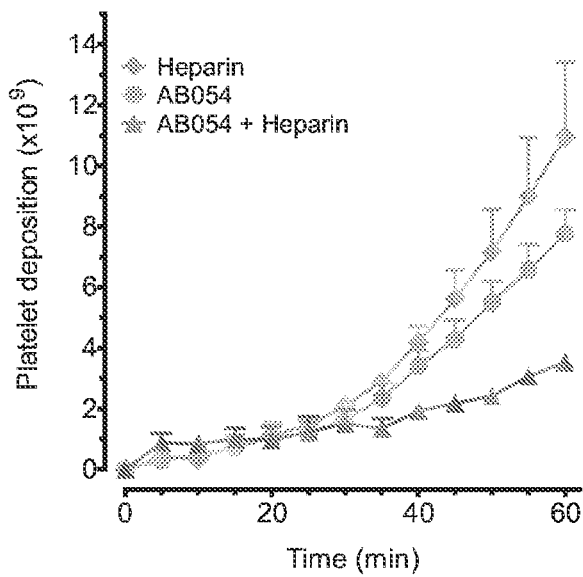
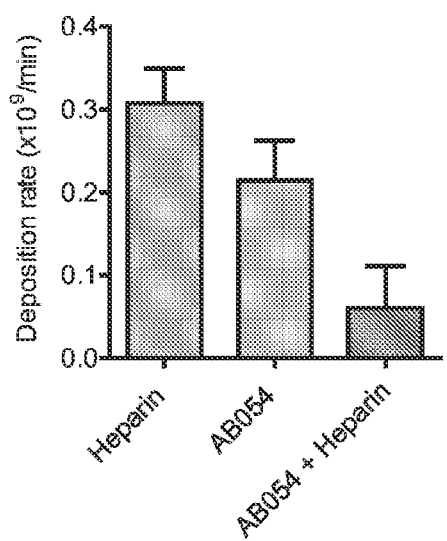

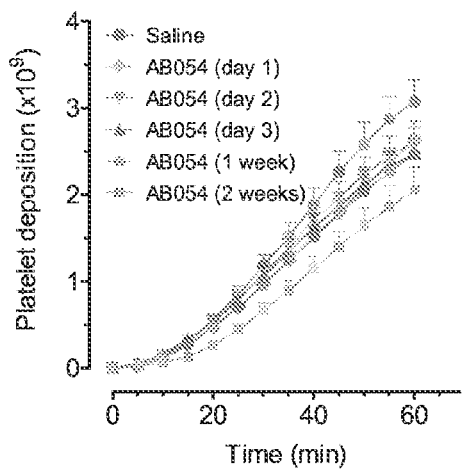
FIG. 23A  Collagen Graft
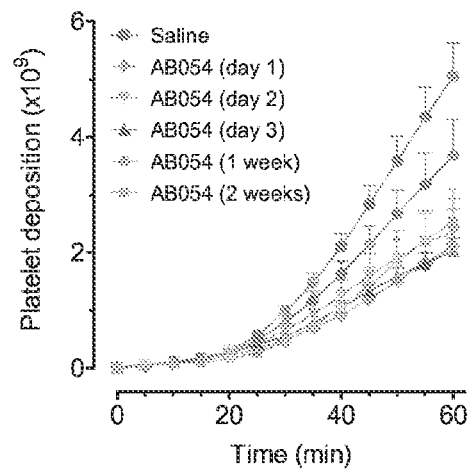
FIG. 23B  Collagen Tail
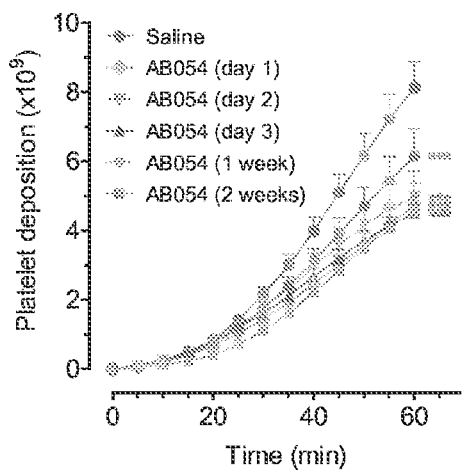
FIG. 23C  Collagen Thrombus
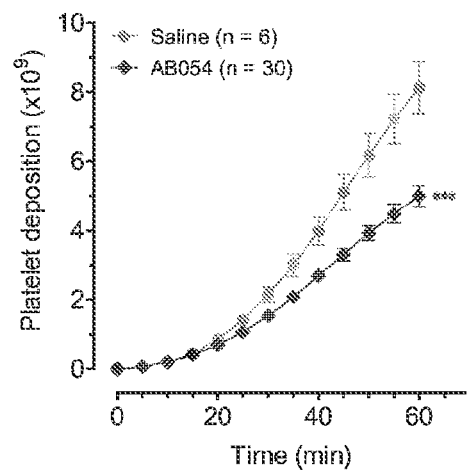
FIG. 23D  Collagen Thrombus

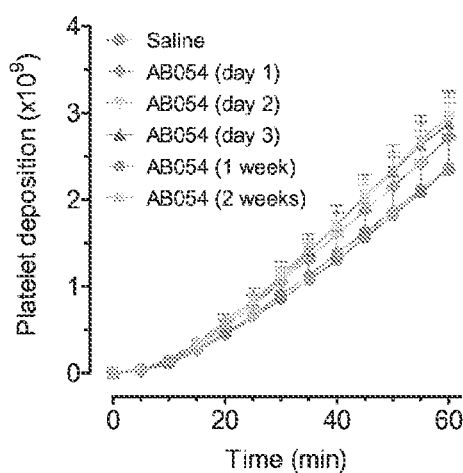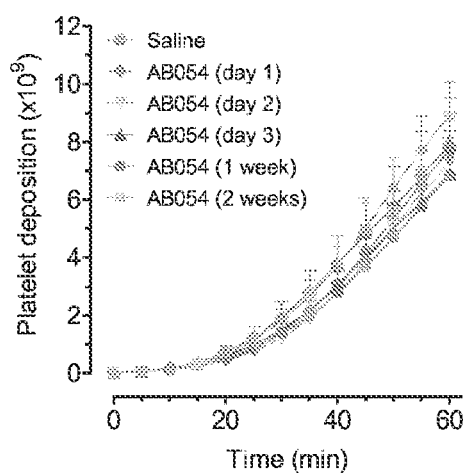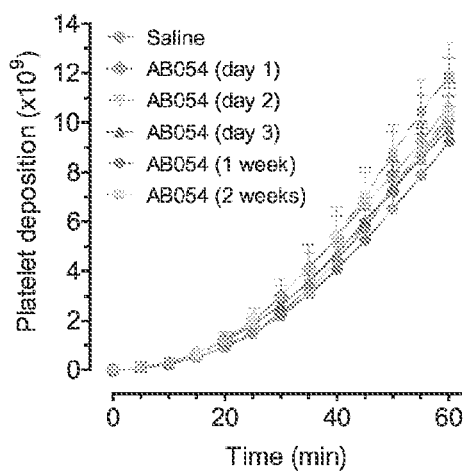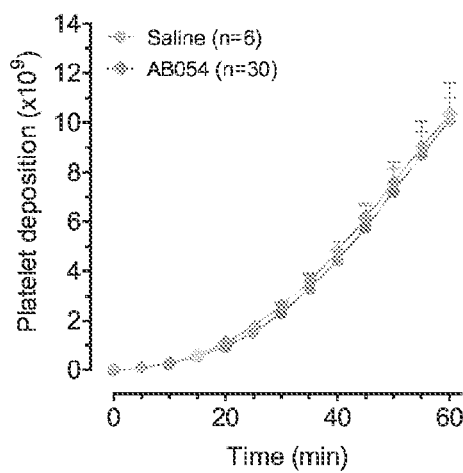
FIG. 24A Tissue Factor Graft
FIG. 24B Tissue Factor Tail
FIG. 24C Tissue Factor Thrombus
FIG. 24D Tissue Factor Thrombus

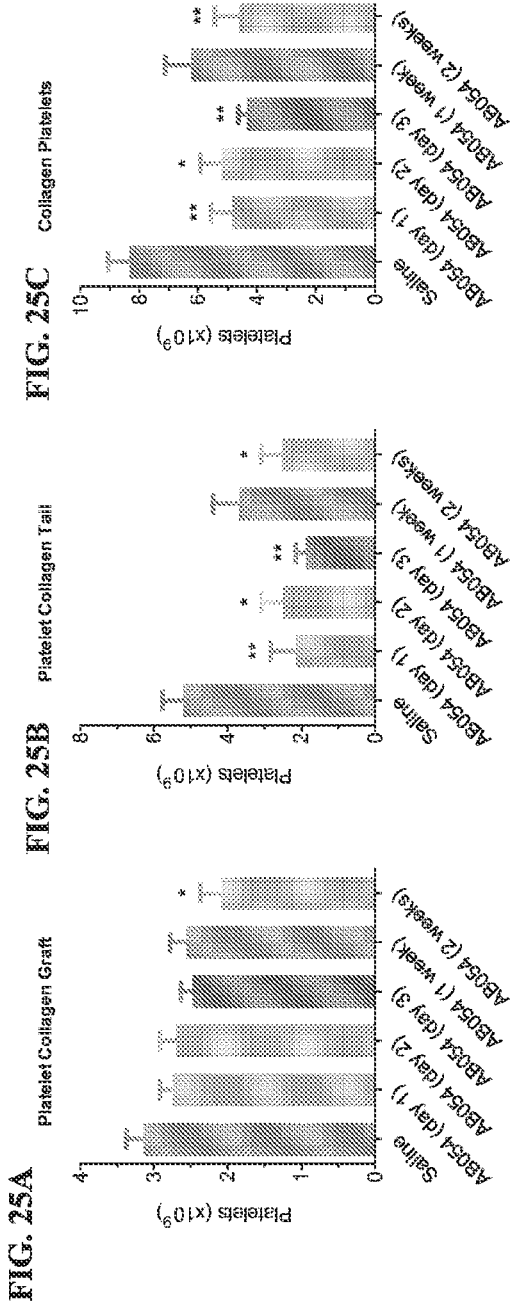
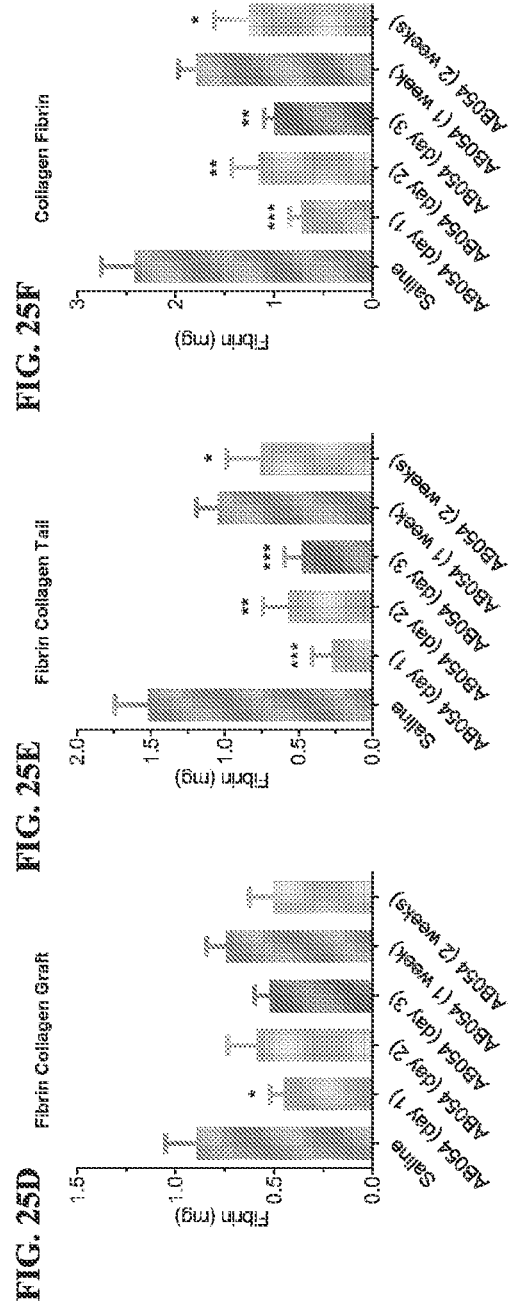

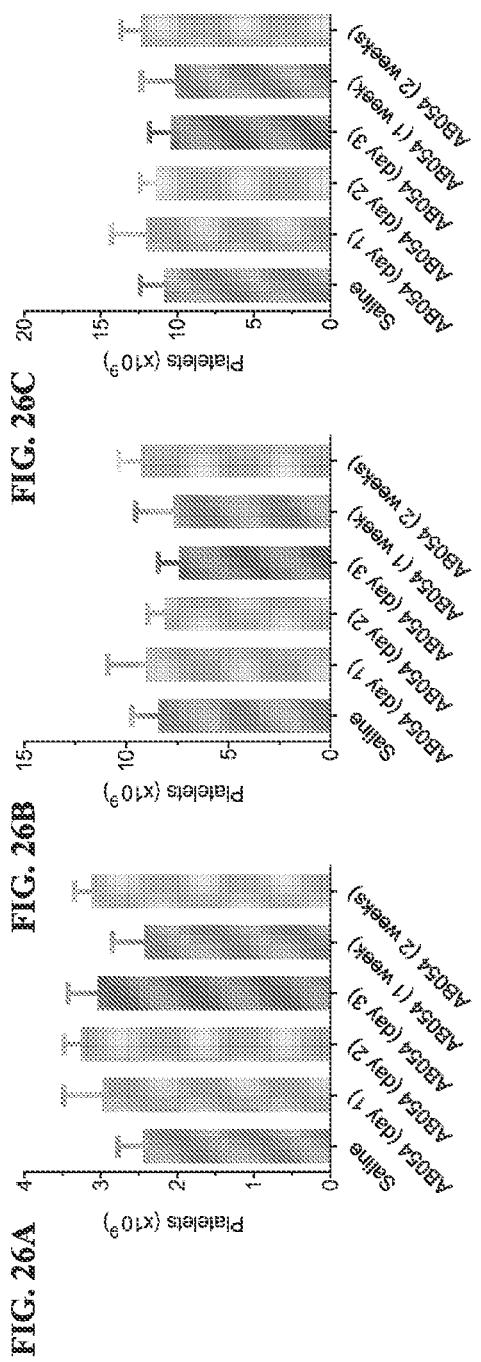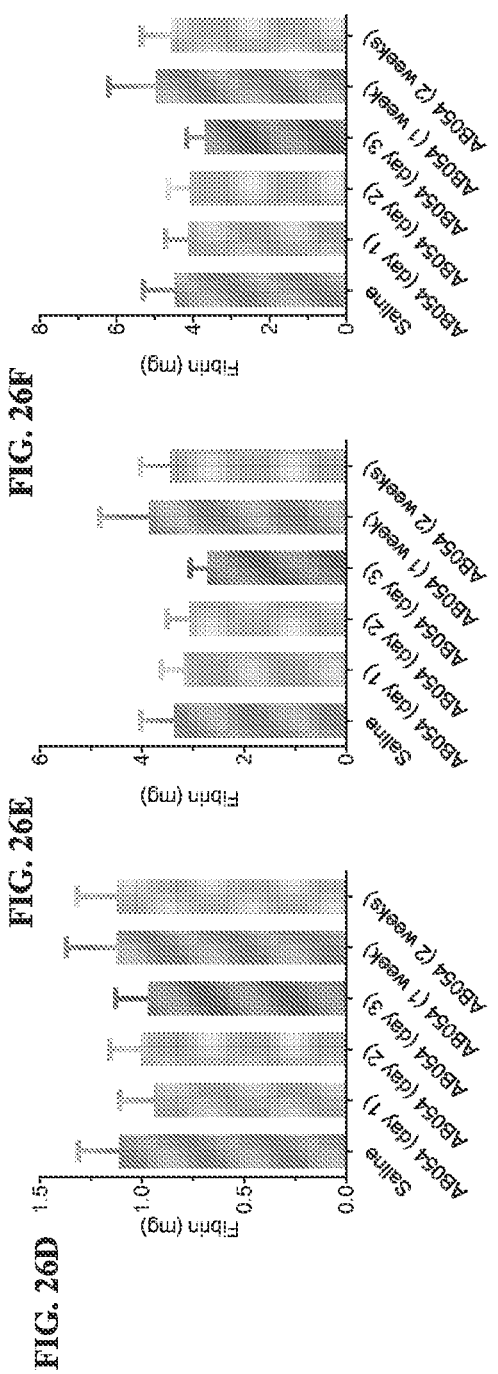

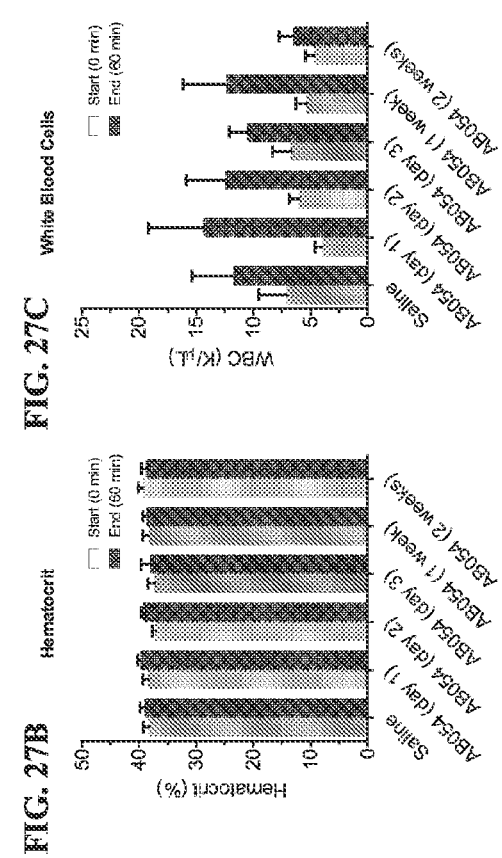
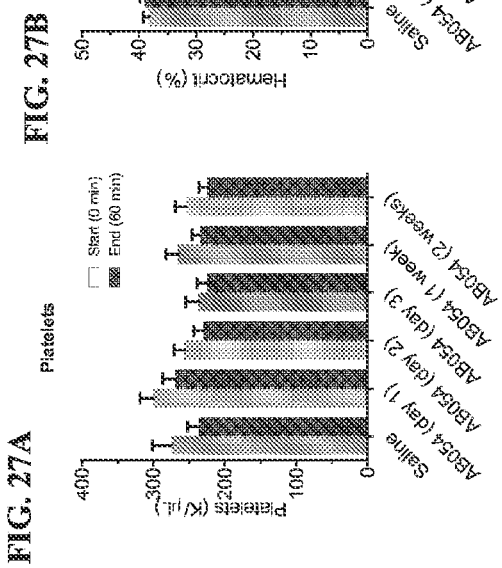
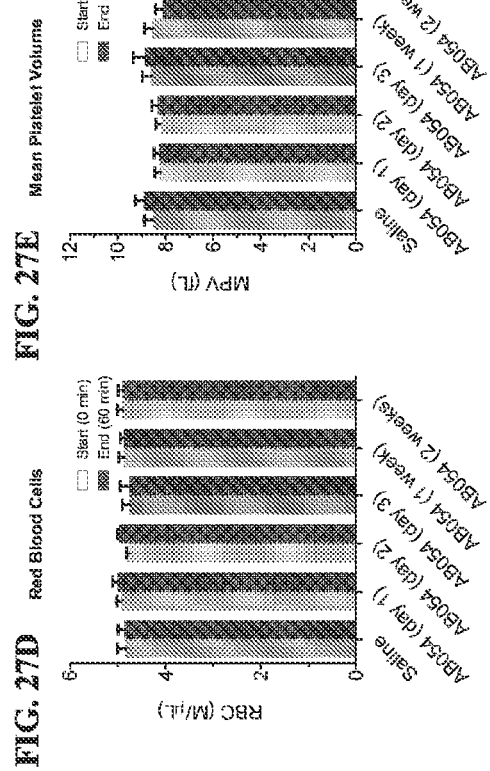

THERAPEUTIC FACTOR XII ANTIBODY

CROSS REFERENCE TO RELATED APPLICATIONS

This application is the U.S. National Stage of International Application No. PCT/US2019/063729, filed Nov. 27, 2019, which was published in English under PCT Article 21(2), which claims the benefit of U.S. Provisional Application No. 62/772,235, filed Nov. 28, 2018, which is herein incorporated by reference in its entirety.

STATEMENT OF GOVERNMENT SUPPORT

This invention was made with government support under AI088937 and HL126235 awarded by the National Institutes of Health. The government has certain rights in the invention.

FIELD

This disclosure concerns a potent therapeutic antibody specific for blood protein factor XII (FXII) and its use in methods of medical treatment, including the treatment of thrombosis and the management of hemostasis.

BACKGROUND

Blood-contacting medical devices, including catheters, stents, grafts, filters, and extracorporeal organ support systems (ECOS) often cause device-associated thromboembolism, even with medical thromboprophylaxis via administration of anticoagulants, because existing anticoagulants are not administered at their maximally effective doses due to adverse bleeding side effects (Lavery et al., *Adv Drug Deliv Rev* 2017; 112:2-11). To maintain patency, perfused devices require prophylactic anticoagulation that can increase the incidence and/or severity of bleeding. Inhibiting contact activation of blood, including FXII inhibition, has been proposed as a safe alternate approach to therapeutic anticoagulation (PCT Publication No. WO 2013/013423; Gruber and Hanson, *Blood* 2003; 102:953-955; Yau et al., *Blood* 2014; 123:2102-2107; Tillman and Gailani, *Semin Thromb Hemost* 2018; 44:60-69). Extracorporeal membrane oxygenation (ECMO) is used for short-term management of respiratory failure; however, its benefits are reduced by anticoagulation-associated bleeding (Oliver, *Semin Cardiothorac Vasc Anesth* 2009; 13:154-175; Murphy et al., *Transfus Med Rev* 2015; 29:90-101; Barbaro et al., *Am J Respir Crit Care Med* 2015; 191:894-901). ECOS systems, such as ECMO, cardiopulmonary bypass, left ventricular assist device (LVAD), total artificial heart (TAH), or hemodialysis, have several components that promote contact and platelet activation (Sniecinski and Chandler, *Anesth Analg* 2011; 113:1319-1333).

Activation of coagulation factors factors other than FXII, plasma kallikrein (PK), or high molecular weight kininogen (HK), in vivo leads to thrombin generation, and subsequent platelet activation and fibrin formation to support hemostasis (Smith et al., *Crit Rev Biochem Mol Biol* 2015; 50:326-336). Pathological blood coagulation inside the vessel lumen may, however also involve FXII, PK, and HK and may cause vaso-occlusive thrombosis/thromboembolism. Pharmacological treatment of thrombosis or thromboprophylaxis is achieved with antithrombotics, such as heparin, that may cause bleeding because they inhibit key hemostatic plasma proteins such as thrombin or factor Xa (Abraham et al., *BMJ* 2015; 350:h1857; Ruff et al., *Lancet* 2014; 383:955-962). Accordingly, these drugs cannot be dosed to full efficacy due to dose-limiting antihemostatic toxicity, and thrombotic vessel occlusion remains the leading cause of mortality in developed countries. To address the issue of antithrombotic safety, it was proposed that inhibiting contact activation would be a safer alternative to current antithrombotic therapy (PCT Publication No. WO 2013/013423; Gruber and Hanson, *Blood* 2003; 102:953-955). Steadily increasing efforts are underway in both industry and academia to develop inhibitors to contact activation complex components to improve the safety of anticoagulation (Tillman et al., *Blood Rev* 2018; 32:433-448).

The plasma contact activation complex promotes pathological thrombus formation. It involves FXI, plasma prekallikrein (PK), and the cofactor high-molecular-weight kininogen (HK) that are activated following exposure of blood to negatively-charged surfaces, which include a variety of biological molecules and artificial materials (Schmaier, *Thromb Res* 2014; 133:S41-S44; Schmaier, *J Thromb Haemost* 2016; 14:28-39; Tillman and Gailani, *Semin Thromb Hemost* 2018; 44:60-69). FXII has a plasma concentration of 30-40 µg/ml (375-500 nM) (Hanson and Tucker, Chapter II.2.6—Blood Coagulation and Blood-Materials Interactions. In: Ratner B D, Hoffman A S, Schoen F J, et al., editor(s). Biomaterials Science (Third Edition). Academic Press; 2013. p. 551-557). Surface-catalyzed cleavage of FXII, an 80 kDa single-chain zymogen, after Arg353 generates the protease α-FXIIa. Cleavage of α-FXIIa after Arg334 generates β-FXIIa, which contains the FXIIa catalytic domain. α-FXIIa activates FXI to FXIa ultimately leading to thrombin (FIIa) generation, and reciprocal activation of FXII. Concomitantly, α-FXIIa activates the zymogen PK to α-kallikrein, which converts additional FXII to α-FXIIa. β-FXIIa activates components of the complement system and as part of the kallikrein-kinin system cleaves the cofactor HK to liberate bradykinin, which leads to the generation of NO, and activation of complement and other systems, such as the renin-angiotensin system (Ivanov et al., *Curr Opin Hematol* 2017; 24:411-418). Thus, contact activation initiates prothrombotic, vasoregulatory, and proinflammatory processes (Renné, *Semin Immunopathol* 2012; 34:31-41).

Contact activation drives thrombin formation in the activated partial thromboplastin time (aPTT) clotting assay, and plasma or blood from mammals lacking a contact protein have prolonged aPTTs (Turi and Peerschke, *Am J Clin Pathol* 1986; 85:43-49). While hereditary FXI deficiency may cause a mild bleeding disorder in humans (hemophilia C), deficiency of FXII, PK, or HK are asymptomatic (Tagariello et al., *Blood Transfus* 2017; 15:557-561; Kitchens, *J Thromb Haemost* 2005; 3:2607-2611; Renne et al., *Blood* 2012; 120:4296-4303). Importantly, while playing a minor to no role in hemostasis, these proteins appear to contribute to thrombosis in some experimental animal models (Renné et al., *J Exp Med* 2005; 202:271-281; Kleinschnitz et al., *J Exp Med* 2006; 203:513-518; Crosby et al., *Arter Thromb Vasc Biol* 2013; 33:1670-1678). FXIIa inhibition using the anti-FXIIa antibody 3F7 reduced fibrin deposition within a membrane oxygenator cartridge in a rabbit ECMO model, whereby venous blood was extracted from a vein of the animal and pumped through the device using a roller pump, without an apparent increase in experimental injury-provoked bleeding (Kenne and Renne, *Drug Discov Today*

2014; 19:1459-1464; Larsson et al., *Sci Transl Med* 2014; 6:222ra17; Worm et al., *Ann Transl Med* 2015; 3:247).

SUMMARY

Monoclonal antibodies that bind, such as specifically bind, blood protein factor XII (FXII) are described. The monoclonal antibodies (including antigen-binding fragments thereof) are capable of forming immune complexes with human FXII and inhibiting FXII activity, resulting in anti-inflammatory and anti-thrombotic effects.

Provided herein are monoclonal antibodies, or antigen-binding fragments thereof, that bind to the catalytic domain and block the catalytic activity of FXII. The monoclonal antibodies or antigen-binding fragments include a variable heavy (VH) domain and a variable light (VL) domain. In some embodiments, the VH domain of the monoclonal antibody or antigen-binding fragment includes the complementarity determining region (CDR) sequences of SEQ ID NO: 2 and/or the VL domain of the monoclonal antibody or antigen-binding fragment includes the CDR sequences of SEQ ID NO: 4.

Also provided are fusion proteins, antibody conjugates and compositions that include a FXII-specific monoclonal antibody, or an antigen-binding fragment thereof, as disclosed herein.

Further provided are nucleic acid molecules and vectors that encode a disclosed monoclonal antibody or antigen-binding fragment. Isolated cells that include a nucleic acid molecule or vector disclosed herein are also provided.

Also provided are methods of detecting FXII in a sample by contacting the sample with a monoclonal antibody or antigen-binding fragment disclosed herein, and detecting binding of the antibody to the sample.

Further provided is an in vitro method of inhibiting activation and/or activity of FXII (such as activity of FXIIa) in a sample that includes FXII, by contacting the sample with a FXII-specific antibody or antigen-binding fragment disclosed herein.

Also provided are methods of inhibiting activation and/or activity of FXII in a subject, methods of treating pathologic hypercoagulation involving activation and/or activity of FXII in a subject, and methods of inhibiting thrombosis or inflammation involving activation and/or activity of FXII in a subject, by administering to the subject an effective amount of an antibody or antigen-binding fragment disclosed herein. In some examples, the methods involve inhibiting activity of activated FXII (FXIIa).

Kits that include a disclosed monoclonal antibody, antigen-binding fragment, fusion protein, antibody conjugate, composition, nucleic acid molecule, vector or isolated cell are further provided by the present disclosure.

The foregoing and other objects, features, and advantages of the disclosure will become more apparent from the following detailed description, which proceeds with reference to the accompanying figures.

BRIEF DESCRIPTION OF THE DRAWINGS

FIGS. 1A-1C: Effects of anti-factor XII antibody 5C12 on plasma coagulation. A standard activated partial thromboplastin time (aPTT) assay using a synthetic lipid reagent was performed. (FIGS. 1A-1B) Increasing concentrations of 5C12 (○) and a control non-inhibiting anti-FXII antibody (●) were incubated for 5 minutes with human (FIG. 1A) or baboon (FIG. 1B) platelet-poor plasma prior to performing the aPTT assay. Data are averages of 2-6 clotting times. (FIG. 1C) Dose-dependent aPTT prolongation by corn trypsin inhibitor (CTI) (♦), a known FXII inhibitor, is compared to aPTT prolongation after inhibition of FXII by 5C12 (○).

FIGS. 2A-2F: Effects of FXII concentration on plasma coagulation. Normal platelet-poor plasma from different species was serially diluted into FXII-deficient human plasma, resulting in platelet-poor plasma with 0.006-100% of FXII. Plasmas were incubated with buffer only (●) or 20 µg/ml 5C12 (○) for 5 min prior to aPTT measurement. The following species were tested for cross-reactivity of 5C12 with FXII of that species: human (FIG. 2A), baboon (FIG. 2B), cynomolgus monkey (FIG. 2C), rhesus macaque (FIG. 2D), mouse (FIG. 2E), and rat (FIG. 2F). A right shift of the curve indicates cross-reactivity of 5C12 with the species tested.

(FIG. 3A) Western blots of platelet poor plasmas from different species (indicated above each lane) size fractionated by SDS-PAGE chromatography. Species included in alphabetical order: African green monkey, baboon, beagle, cat, cattle, chicken, cynomolgus monkey, dog, elephant, giant anteater, horse, human, human deficient in FXII, llama, marmoset, pig, rabbit, raccoon, rat, red kangaroo, rhesus macaque and tiger. Human plasma and human deficient in FXII plasma were used in all gels as a positive and negative control, respectively. The antibody 5C12 recognizes both recombinant and plasma-derived FXII in their non-reduced state on an SDS-PAGE gel, but does not recognize the reduced form of either the recombinant or plasma FXII (FIG. 3B). 5C12 also recognizes both the alpha (comprising both the light and heavy chain of FXII) and the beta (comprising only the light chain and a nonapeptide fragment of the heavy chain) form of activated FXII (FXIIa) (FIG. 3C). The primary antibody for all Western blots was murine 5C12, the secondary antibody was goat-anti-mouse polyclonal.

(FIGS. 4A-4B) 5C12 or a control non-inhibiting FXII antibody were pre-incubated with FXII for 10 minutes at room temperature (RT) and were then added to a solution of short polyphosphates (FIG. 4A) or long polyphosphates (FIG. 4B), high molecular weight kininogen (HK), and prekallikrein (PK) for a final concentration of 50 nM FXII, 10 µM polyphosphates, 12.5 nM PK, and 12.5 nM HK, and varying concentrations of antibody (0-100 nM). The samples were incubated at 37° C. for 60 minutes. PK was then inhibited by soybean trypsin inhibitor (50 µg/ml) and polyphosphates were neutralized by polybrene (6 µg/ml) and FXIIa was measured by addition of the chromogenic substrate, Spectrozyme FXIIa (final concentration of 0.5 mM). (FIG. 4C) 5C12 or the control antibody (0-80 nM) were pre-incubated with FXII (40 nM) for 10 minutes at RT. Dextran sulfate was then added to each sample at a final concentration of 1 µg/ml and the samples were incubated for 20 minutes at 37° C. FXIIa was measured by addition of the chromogenic substrate, Spectrozyme FXIIa (final concentration of 0.5 mM). (FIG. 4D) 5C12 or the control antibody (0-40 nM) were pre-incubated with FXIIa (20 nM) for 10 minutes. FXIIa activity was then measured by addition of the chromogenic substrate, Spectrozyme FXIIa (final concentration of 0.5 mM). Symbols are (○) 5C12, (●) control antibody. (FIG. 4E) Human FXII (100 nM) was incubated with 5 nM human kallikrein and 10 µg/ml dextran sulfate for 0, 15, 30 and 60 minutes at 37° C. in the presence or absence of 100 nM 5C12. 40 µg/ml CTI was added to each sample to block the activity of FXIIa. Samples were separated by SDS-PAGE under reducing conditions, transferred to PVDF membrane and immunoblotted with an anti-FXII antibody. Proteins were detected using ECL (GE Healthcare, Piscataway, NJ, USA).

FIGS. 5A-5H: Timecourse of 5C12 antibody activity in vivo. A single baboon (*Papio anubis*) was injected intravenously with six doses of 1 mg/kg 5C12 given 40 minutes apart, for a combined dose of 6 mg/kg. Blood samples were drawn into 1/10th volume of 3.2% sodium citrate at indicated time points and processed to platelet-poor plasma. A second blood sample was drawn into EDTA-K2-coated tubes for measurement of complete blood count. Measurement of plasma coagulation was performed using aPTT (FIG. 5A), prothrombin time (PT) (FIG. 5B), and activated clotting time (ACT) (FIG. 5C). Thrombin-anti-thrombin time (TAT) (FIG. 5D) was measured using the Enzygnost TAT micro ELISA kit (Siemens Healthcare Diagnostics Products GmbH). A complete blood count (CBC) was performed on every day a blood sample was taken. Platelet count (FIG. 5E), hematocrit (FIG. 5F), white blood cell count (FIG. 5G), and red blood cell count (FIG. 5H) are shown. All measurements stay within normal range for baboons. The normal range of these parameters is indicated by dotted lines in each panel.

FIGS. 6A-6E: Baboon model of surface-initiated thrombosis. (FIG. 6A) A baby extracorporeal membrane oxygenator (ECMO, Capriox Baby RX05, Terumo Corporation) was inserted into a chronic AV shunt of a juvenile male baboon (*Papio anubis*) and positioned in the center of a GE-Brivo NM 615 Nuclear Medicine imaging system. Blood flow through the ECMO device was regulated by a distal clamp to a flow of 100 ml/min and experiments ran for 60 minutes. Platelets were labeled using $^{111}$In to enable real-time monitoring of platelet deposition in the ECMO device. Treatments were given prior to each experiment, except for control studies (●). Heparin (♦) was administered as a bolus i.v. injection of 20 U/kg 15 minutes prior to the experiment. 5C12 (○), 5 mg/kg i.v. bolus, was given 30 minutes prior to the experiment. The combination study of 5C12 and heparin (◇) was performed 48 hours post the initial 5C12 administration and a second "top off" dose of 2 mg/kg of 5C12, as well as a fresh dose of 20 U/kg heparin were given. FIG. 6B displays the platelet deposition rate (billion platelets deposited per minute) during the second half (minutes 30-60) of the study. FIGS. 6C-6D display the terminal platelet count and fibrin content, respectively, of the thrombus formed in the ECMO device, while FIG. 6E shows the correlation between these two parameters.

FIGS. 7A-7C: Plasma coagulation measurements during ECMO shunt studies. Blood samples were drawn at the beginning (white bars) and end (black bars) of the ECMO thrombosis study into 1/10th volume of 3.2% sodium citrate. ACT (FIG. 7B) was measured directly in whole blood. Measurement of aPTT (FIG. 7A) and PT (FIG. 7C) was done using platelet-poor plasma.

FIGS. 9A-9C: Hemostasis assessment during AV shunt studies. During each shunt thrombosis study, two hemostasis measurements were taken 15 minutes into the study. Bleeding time (FIG. 9A) was measured using a standard template skin bleeding time test (Surgicutt®, International Technidyne Corp, Piscataway, NJ) and recorded using a manual stopwatch. Blood drops emerging from the wound were collected every 30 s using a Whatman blotting paper (FIG. 9B). Bleeding volume was assessed using this blotting paper and Drabkin's reagent (Sigma), a quantitative, colorimetric chemical that allows for the determination of hemoglobin concentration in whole blood. The dried blood sample on the blotting paper was soaked in 2.5 mL Drabkin's reagent until completely dissolved. Absorbance was measured at 540 nm and compared to a standard curve using blood of the tested animal. Bleeding rate was calculated as the ratio of bleeding volume over time (FIG. 9C). Each data point represents a single measurement.

(FIG. 10A) Platelet-poor plasma was generated and spiked with either vehicle (●) or 40 µg/ml 5C12 (○) and incubated for 5 minutes prior to measurement of aPTT. (FIG. 10B) Whole blood was spiked with either vehicle (●) or 40 µg/ml 5C12 (○) and incubated for 15 minutes before centrifugation to obtain platelet-poor plasma and aPTT measurement. (FIGS. 10C-10F) Thromboelastometry was measured using a ROTEM® delta whole blood analyzer (Tem Systems, Inc. Research Triangle Park, NC). Whole blood was spiked with either vehicle (●) or 40 µg/ml 5C12 (○) and incubated for 5 minutes. In the special ROTEM® cuvettes, 20 µl 200 mM $CaCl_2$ and 300 µl blood were mixed and measurement was started using the automatic pipetting system and timing of the ROTEM® delta analyzer. Parameters shown are: (FIG. 10C) clotting time (CT), the time till the clot starts forming; (FIG. 10D) clot formation time (CFT), the time between the start of the clot and the time the clot reached the firmness of 20 mm force; (FIG. 10E) maximum clot firmness (MCF), the maximum strength of the clot; and (FIG. 10F) Alpha angle, a measurement of the time to maximum velocity of clot formation.

15B) and PT (FIG. 15C) were evaluated for each treatment group at the start of perfusion (0 min) and at the end of perfusion (60 min). If heparin was given, a measurement was taken before heparin administration (Pre Heparin). Data are expressed as means±SEM.

Figure 16A:
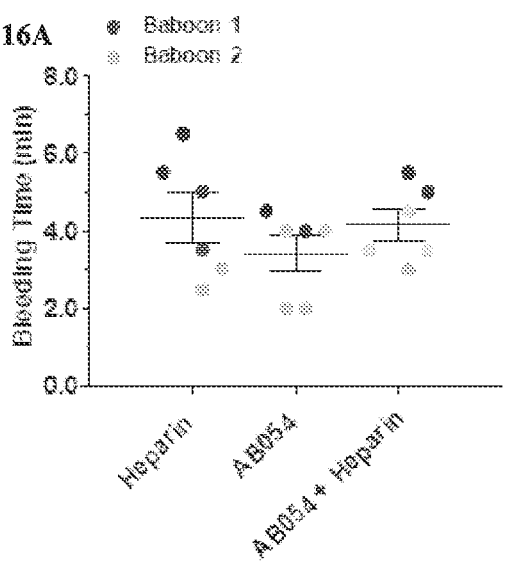

FIGS. 16A-16C: Primary hemostasis measurements during membrane oxygenator perfusion experiments. The effect of AB054 on bleeding time (FIG. 16A), bleeding volume (FIG. 16B) and bleeding rate (FIG. 16C) was assessed approximately 15 minutes following the start of perfusion. Two measurements were performed during each perfusion experiment and averages are shown in black lines.

FIGS. 17A-17B: Platelet accumulation within the membrane oxygenator. Real-time platelet accumulation within the membrane oxygenator was measured during the 60-minute perfusion experiment. (FIG. 17A) The oxygenator was placed on top of the gamma camera and the emitted radioactivity was recorded in five-minute frames. (FIG. 17B) The average deposition rate per minute during the second half of the experiment (30 to 60 minutes), when the thrombus was growing. Data are expressed as means±SEM.

Figure 18A:
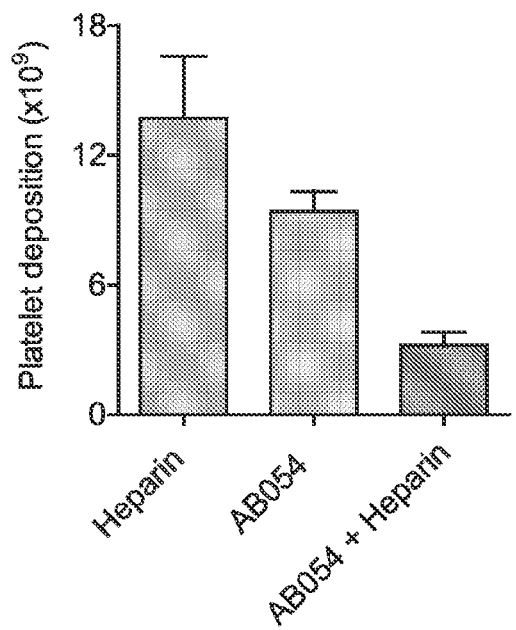
Figure 18B:
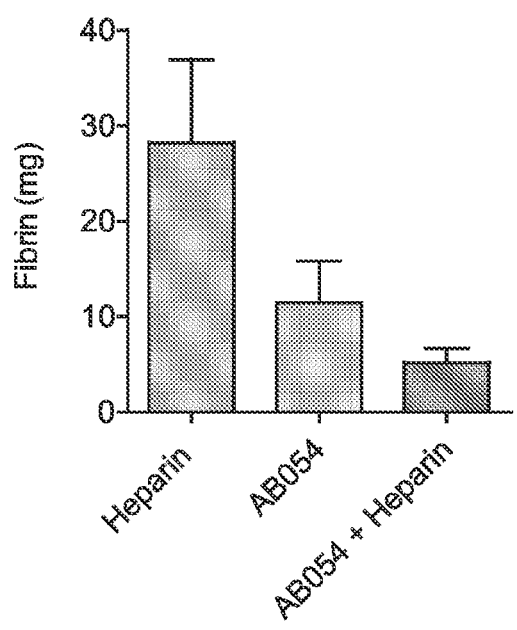

FIGS. 18A-18B: Measurements of terminal platelets and fibrin within the membrane oxygenator. (FIG. 18A) Final platelet deposition after 60 minutes of membrane oxygenator perfusion was measured in the rinsed, saline-filled device. (FIG. 18B) Iodine-125 labeled fibrin content was measured after the radioactivity of Indium-111 had decayed. Data are expressed as means±SEM.

Figure 19:
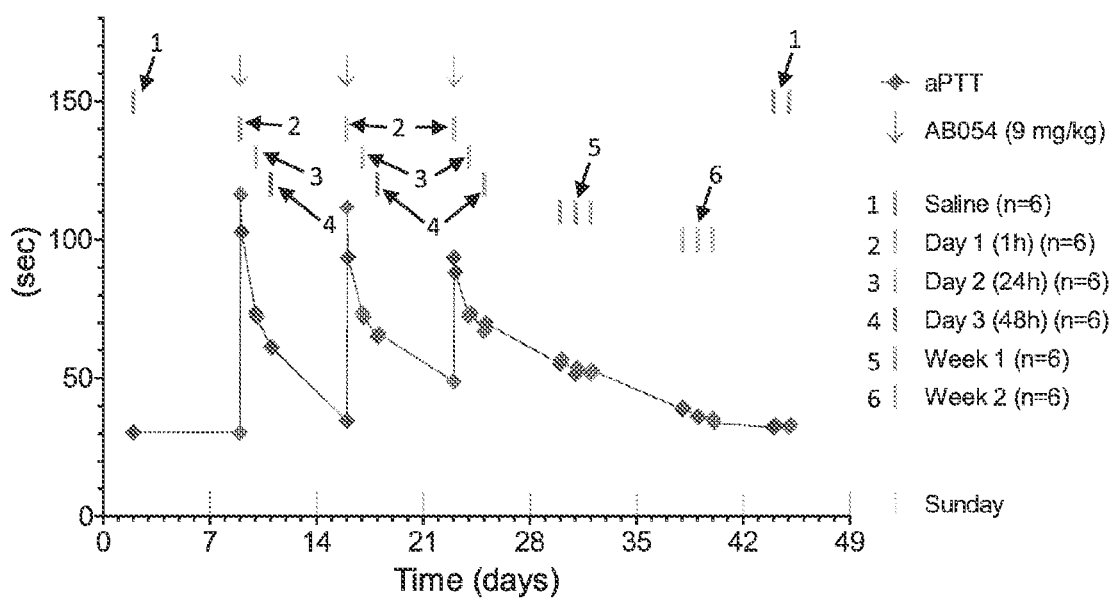

FIG. 19: Timeline of experiments. Seventy-two thrombosis experiments were performed over a 7-week period in a single baboon. On each study day, two perfusion experiments were performed utilizing one collagen-coated and one tissue factor-coated graft connected in series (i.e. 4 graft experiments each day). The baboon received one dose of AB054 (9 mg/kg) each week (arrows), and experiments were executed the same day, as well as on the two following days. Experimental days and treatment groups are indicated by vertical lines. After the final dose of AB054, experiments were performed at one week and two weeks post dose. Saline controls were performed in week 1, and in week 7 after clearance of the antibody. N=6 for all groups.

Figure 20A:
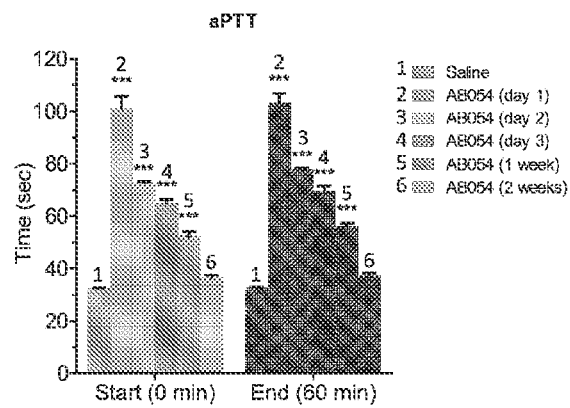
Figure 20B:
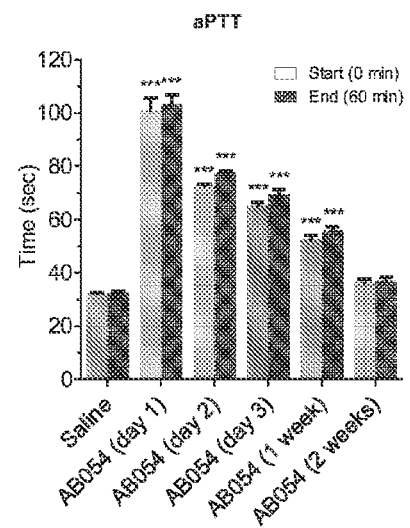
Figure 20C:
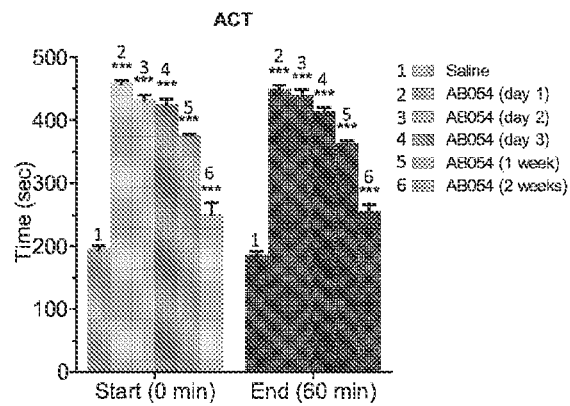
Figure 20D:
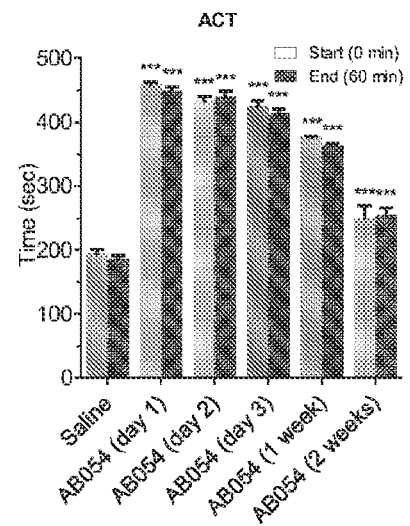

FIGS. 20A-20D: aPTT and ACT measurements during graft perfusion experiments. Coagulation parameters including aPTT (FIGS. 20A, 20B) and ACT (FIGS. 20C, 20D) were measured for each treatment group at start of perfusion (0 min) and at the end of perfusion (60 min). Data is grouped either by time (FIGS. 20A, 20C) or treatment group (FIGS. 20B, 20D). N=6 for all groups. Data are expressed as the means±SEM. ***$p<0.001$ vs. saline.

Figure 21A:
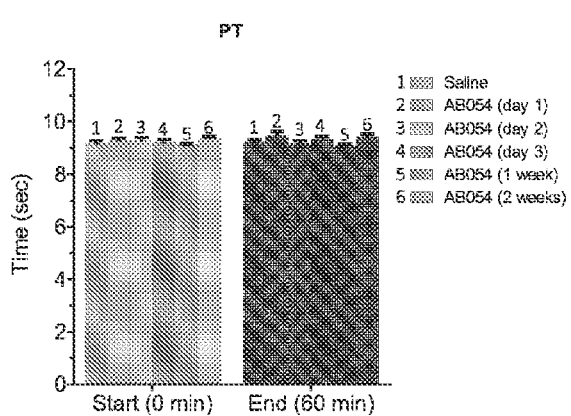
Figure 21B:
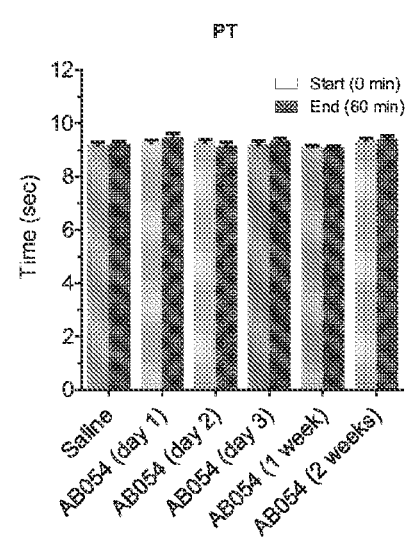

FIGS. 21A-21B: PT measurements during graft perfusion experiments. Hemostasis assessment using PT was measured for each treatment group at start of perfusion (0 min) and at the end of perfusion (60 min). Data is grouped either by time (FIG. 21A) or treatment group (FIG. 21B). N=6 for all groups. Data are expressed as the means±SEM.

Figure 22:
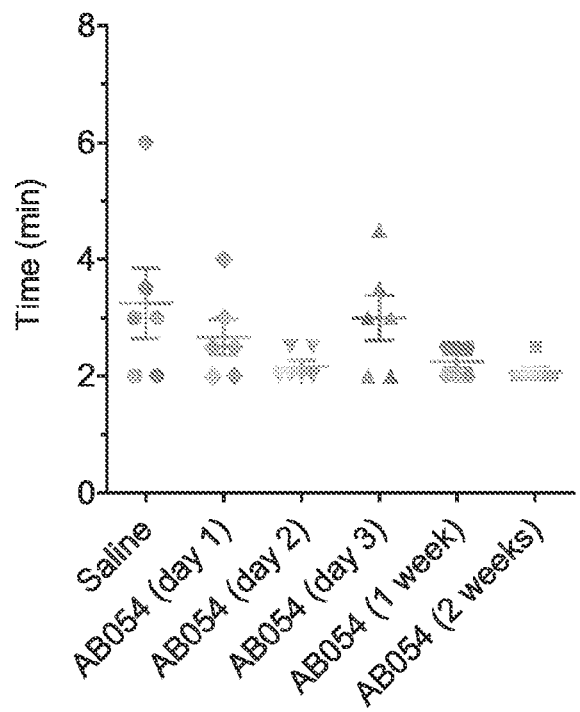

FIG. 22: Bleeding measurements during graft perfusion experiments. The effect of AB054 on bleeding time was assessed approximately 15 minutes following start of perfusion. One measurement was performed during each perfusion experiment. Data are shown as a scatter plot with means±SEM.

FIGS. 23A-23D: Platelet accumulation in the collagen-coated graft. Real time platelet accumulation in the collagen-coated graft during the 60-minute perfusion experiment. (FIG. 23A) Graft thrombus within the graft itself. (FIG. 23B) Tail thrombus distal to the graft. (FIG. 23C) Total platelet accumulation in the graft and tail combined. N=6 for each group (FIG. 23D) Total platelet accumulation of all experiments post AB054 administration combined (N=30 for post AB054). Data are expressed as the means±SEM. Statistical analysis was only performed for the complete thrombus (FIGS. 23C and 23D); ***$p<0.001$ vs. saline.

FIGS. 24A-24D: Platelet accumulation in the tissue factor-coated graft. Real time platelet accumulation in the tissue factor-coated graft during the 60-minute perfusion experiment. (FIG. 24A) Graft thrombus within the graft itself (FIG. 24B) Tail thrombus distal to the graft. (FIG. 24C) Total platelet accumulation in the graft and tail combined. N=6 for each group. (FIG. 24D) Total platelet accumulation of all experiments post AB054 administration combined (N=30 for post AB054). Data are expressed as the means±SEM.

FIGS. 25A-25F: Measurements of terminal platelet accumulation and fibrin content in the collagen-coated graft. Final platelet deposition in the collagen-coated graft and distal tail after 60 minutes of perfusion was measured in the rinsed, saline-filled shunt loop (FIGS. 25A-25C). $^{125}$I-labeled fibrin content was measured after the radioactivity of $^{111}$In had decayed (FIGS. 25D-25F). Data are expressed as the means±SEM; *$p<0.05$, $p<0.01$, *$p<0.001$ vs. saline.

FIGS. 26A-26F: Measurements of terminal platelet accumulation and fibrin content in the tissue factor-coated graft. Final platelet deposition in the tissue factor-coated graft and distal tail after 60 minutes of perfusion was measured in the rinsed, saline-filled shunt loop (FIGS. 26A-26C). $^{125}$I-labeled fibrin content was measured after the radioactivity of $^{111}$In had decayed (FIGS. 26D-26F). Data are expressed as the means±SEM.

FIGS. 27A-27E: Complete blood count. Complete blood counts were measured for each treatment group at the start of perfusion (0 min) and at the end of perfusion (60 min). Parameters measured included platelet count (FIG. 27A), hematocrit (FIG. 27B), white blood cell count (FIG. 27C), red blood cell counts (FIG. 27D), and mean platelet volume (FIG. 27E). White blood cell count increased and platelet count decreased during active thrombus formation, while other parameters remain unchanged. Repeat dosing of AB054 had no effect on the complete blood count of the baboon. Data are expressed as the means±SEM.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on May 24, 2021, 42.4 KB, which is incorporated by reference herein. In the accompanying sequence listing:

SEQ ID NO: 1 is the amino acid sequence of the 5C12 heavy chain.

SEQ ID NO: 2 is the amino acid sequence of the 5C12 VH domain.

SEQ ID NO: 3 is the amino acid sequence of the 5C12 light chain.

SEQ ID NO: 4 is the amino acid sequence of the 5C12 VL domain.

SEQ ID NO: 5 is the cDNA sequence of the 5C12 heavy chain.

SEQ ID NO: 6 is the cDNA sequence of the 5C12 light chain.

SEQ ID NO: 7 is the amino acid sequence of a humanized HC1 heavy chain.

SEQ ID NO: 8 is the amino acid sequence of the humanized HC1 VH domain.

SEQ ID NO: 9 is the amino acid sequence of a humanized LC1 light chain.

SEQ ID NO: 10 is the amino acid sequence of the humanized LC1 VL domain.

SEQ ID NO: 11 is the cDNA sequence of the humanized HC1 heavy chain.

SEQ ID NO: 12 is the cDNA sequence of the humanized LC1 light chain.

SEQ ID NO: 13 is the amino acid sequence of a humanized HC2 heavy chain.

SEQ ID NO: 14 is the amino acid sequence of the HC2 VH domain.

SEQ ID NO: 15 is the amino acid sequence of a humanized HC3 heavy chain.

SEQ ID NO: 16 is the amino acid sequence of the HC3 VH domain.

SEQ ID NO: 17 is the amino acid sequence of a humanized LC2 light chain.

SEQ ID NO: 18 is the amino acid sequence of the LC2 VL domain.

SEQ ID NO: 19 is the amino acid sequence of a humanized LC3 light chain.

SEQ ID NO: 20 is the amino acid sequence of the LC3 VL domain.

SEQ ID NO: 21 is the cDNA sequence of the humanized HC2 heavy chain.

SEQ ID NO: 22 is the cDNA sequence of the humanized LC2 light chain.

SEQ ID NO: 23 is the cDNA sequence of the humanized HC3 heavy chain.

SEQ ID NO: 24 is the cDNA sequence of the humanized LC3 light chain.

DETAILED DESCRIPTION

I. Abbreviations
ACT activated clotting time
aPTT activated partial thromboplastin time
AV arteriovenous
bpm billion per min
BT bleeding time
CBC complete blood count
CTI corn trypsin inhibitor
ECMO extracorporeal membrane oxygenation
ECOS extracorporeal organ support systems
FXII blood protein factor XII
FXIIa activated FXII
HK high-molecular-weight kininogen
i.v. intravenous
MAb monoclonal antibody
PF4 platelet factor 4
PK prekallikrein
PT prothrombin time
TAT thrombin-antithrombin complex II. Terms and Methods Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

In order to facilitate review of the various embodiments of the disclosure, the following explanations of specific terms are provided:

Administration: The introduction of a composition into a subject by a chosen route. For example, if the chosen route is intravenous, the composition is administered by introducing the composition into a vein of the subject.

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and is functionally similar to mammalian IgG and IgE. IgW and IgNAR antibodies are produced by cartilaginous fish, while IgX antibodies are found in amphibians.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online.

A "single-domain antibody" refers to an antibody having a single domain (a variable domain) that is capable of specifically binding an antigen, or an epitope of an antigen, in the absence of an additional antibody domain. Single-domain antibodies include, for example, $V_H$ domain antibodies, $V_{NAR}$ antibodies, camelid $V_H$H antibodies, and $V_L$ domain antibodies. $V_{NAR}$ antibodies are produced by cartilaginous fish, such as nurse sharks, wobbegong sharks, spiny dogfish and bamboo sharks. Camelid $V_H$H antibodies are produced by several species including camel, llama, alpaca, dromedary, and guanaco, which produce heavy chain antibodies that are naturally devoid of light chains.

A "monoclonal antibody" is an antibody produced by a single clone of lymphocytes or by a cell into which the coding sequence of a single antibody has been transfected. Monoclonal antibodies are produced by methods known to those of skill in the art. Monoclonal antibodies include humanized monoclonal antibodies.

A "chimeric antibody" has framework residues from one species, such as human, and CDRs (which generally confer antigen binding) from another species.

A "humanized" antibody is an immunoglobulin including a human framework region and one or more CDRs from a non-human (for example a mouse, rabbit, rat, shark or synthetic) immunoglobulin. The non-human immunoglobulin providing the CDRs is termed a "donor," and the human immunoglobulin providing the framework is termed an "acceptor." In one embodiment, all CDRs are from the donor immunoglobulin in a humanized immunoglobulin. Constant regions need not be present, but if they are, they must be substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions.

Anticoagulant: A compound (such as a pharmaceutical agent or molecule) that prevents or inhibits the clotting of blood. Pharmaceutical anticoagulants can be used to treat thrombotic disorders, such as deep vein thrombosis, pulmonary embolism, myocardial infarction and stroke.

Antigen-binding fragment: A portion of a monoclonal antibody that retains its ability to specifically bind the antigen against which the monoclonal antibody was raised. Antigen-binding fragments include but are not limited to Fab fragments, Fab' fragments, F(ab)'$_2$ fragments, single chain Fv proteins (scFv), and disulfide stabilized Fv proteins.

Antithrombotic: Any compound (such as a pharmaceutical agent or molecule) that prevents or inhibits the formation of a thrombus. Antithrombotic agents include anticoagulants (which limit the ability of platelets to clot), antiplatelet drugs (which limit the migration and aggregation of platelets) and thrombolytic drugs (which dissolve clots after they have formed).

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In another embodiment, antibody affinity is measured by flow cytometry. An antibody that "specifically binds" an antigen (such as FXII) is an antibody that binds the antigen with high affinity and does not significantly bind other unrelated antigens.

Coagulation: The process of polymerization of fibrin monomers, resulting in the transformation of blood or plasma from a liquid to a gel phase. Coagulation of liquid blood may occur in vitro, intravascularly or at an exposed and injured tissue surface. In vitro blood coagulation results in a gelled blood that maintains the cellular and other blood components in essentially the same relative proportions as found in non-coagulated blood, except for a reduction in fibrinogen content and a corresponding increase in fibrin.

Complementarity determining region (CDR): A region of hypervariable amino acid sequence that defines the binding affinity and specificity of an antibody.

Complement System: A part of the immune system (specifically the innate immune system) that plays a major role in the lysis of infectious organisms, activation of inflammation, opsonization, and immune clearance.

Conjugate: An antibody or antibody fragment (such as an antigen-binding fragment) covalently linked to an effector molecule (such as a detectable label) or a second protein (such as a second antibody). The effector molecule can be, for example, a drug, toxin, therapeutic agent, detectable label, protein, nucleic acid, lipid, nanoparticle, or carbohydrate. An antibody conjugate is often referred to as an "immunoconjugate."

Conservative variant: "Conservative" amino acid substitutions are those substitutions that do not substantially affect or decrease the affinity of a protein, such as an antibody to FXII. For example, a monoclonal antibody that specifically binds FXII can include at most about 1, at most about 2, at most about 5, at most about 10, or at most about 15 conservative substitutions and specifically bind FXII. The term "conservative variant" also includes the use of a substituted amino acid in place of an unsubstituted parent amino acid, provided that antibody specifically binds FXII. Non-conservative substitutions are those that reduce an activity or binding to FXII.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form.

Detectable label: A detectable compound or composition that is conjugated directly or indirectly to another molecule, such as an antibody or a protein, to facilitate detection of that molecule. Specific, non-limiting examples of detectable labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinylated moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinylated groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Epitope: An antigenic determinant. These are particular chemical groups or peptide sequences on a molecule that are antigenic (that elicit a specific immune response). An antibody specifically binds a particular antigenic epitope on a polypeptide, such as FXII.

Factor XII (FXII or fXII): Any variant, isoform, and/or species homolog of human coagulation factor XII, also known as Hageman factor, naturally expressed by cells and present in plasma. FXII is a plasma glycoprotein that participates in the initiation of blood coagulation, fibrinolysis, and the generation of bradykinin and angiotensin. Prekallikrein is cleaved by FXII to form kallikrein, which then cleaves FXII to form α-FXIIa, which is then cleaved by trypsin to form β-FXIIa. α-FXIIa is composed of the $NH_2$-terminal heavy chain (coagulation factor XIIa heavy chain) and the COOH-terminal light chain (coagulation factor XIIa light chain), connected by a disulfide bond. α-FXIIa activates FXI to FXIa. It also drives selective cleavage of Arg-l-Ile bonds in FVII to form FVIIa. β-FXIIa is composed of two chains linked by a disulfide bond, a light chain (β-FXIIa part 2), corresponding to the COOH-terminal light chain (coagulation FXIIa light chain) and a nonapeptide (β-FXIIa part 1). FXII interacts with histidine-rich glycoprotein (HRG); the interaction, which is enhanced in the presence of zinc ions and inhibited by heparin-binding, inhibits fXII autoactivation and contact-initiated coagulation.

Defects in FXII are the cause of FXII deficiency (FA12D), also known as Hageman factor deficiency. This trait is an asymptomatic anomaly of in vitro blood coagulation. Its diagnosis is based on finding a low plasma activity of the factor in coagulating assays. It is usually only accidentally discovered through pre-operative blood tests. FXII deficiency is divided into two categories, a cross-reacting material (CRM)-negative group (negative FXII antigen detection) and a CRM-positive group (positive FXII antigen detection).

Framework region: Amino acid sequences interposed between CDRs. Framework regions include variable light and variable heavy framework regions. The framework regions serve to hold the CDRs in an appropriate orientation for antigen binding.

Fusion protein: A protein comprising at least a portion of two different (heterologous) proteins.

Hemostasis: The physiologic process whereby bleeding is halted. Hemostatic agents are those that prevent, treat or ameliorate abnormal bleeding, such as abnormal bleeding caused by a bleeding disorder or bleeding episode. Disorders of hemostasis include, for example, platelet disorders, such as idiopathic thrombocytopenic purpura, and disorders of coagulation, such as hemophilia. Hemostasis can also refer to the complex interaction between vessels, platelets, coagulation factors, coagulation inhibitors and fibrinolytic proteins to maintain the blood within the vascular compartment in a fluid state. The objective of the hemostatic system is to preserve intravascular integrity by achieving a balance between hemorrhage and thrombosis. As used herein, "promoting hemostasis" refers to the process of contributing to or improving hemostasis in a subject. For example, an agent that promotes hemostasis can be an agent that reduces abnormal bleeding, such as by halting bleeding more rapidly, or by reducing the amount of blood loss.

Heterologous: Originating from a separate genetic source or species.

Increased bleeding tendency: Bleeding that is spontaneous, excessive, and/or delayed in onset following tissue injury.

Inflammation: Part of the biological defense response of body tissue to harmful stimuli, such as pathogens, damaged cells, or irritants. This protective response involves immune cells, blood vessels, and molecular mediators. The function of inflammation is to help eliminate the initial cause of cell injury, clear out necrotic cells that were damaged from the original insult or from the inflammatory process, and then to prime the tissue repair pathways.

Inhibitory amount or inhibitory dose: The quantity of a specific substance sufficient to achieve inhibition of the activity of a particular molecule or inhibition of the activation of a particular molecule. For instance, this can be the amount necessary to inhibit activation and/or activity of FXII in a subject or a sample (such as a plasma or serum sample). In some embodiments, the inhibitory amount of a monoclonal antibody specific for FXII, or an antigen-binding fragment thereof, is the amount necessary to inhibit activation of FXII by at least 50%. In some examples, the inhibitor amount is the amount necessary to inhibit activation of FXII by 90-100%.

Ischemic organ disease: A disease, condition, state, or disorder in which blood supply to an organ is curtailed, limited, or obstructed, including arteriosclerosis obliterans, Buerger disease, Raynaud disease, myocardial infarction, angina pectoris, diabetic neuropathy, spinal canal stenosis, cerebrovascular accidents, cerebral infarction, pulmonary hypertension, bone fracture, and Alzheimer's disease.

Isolated: An "isolated" biological component, such as a nucleic acid, protein (including antibodies) or organelle, has been substantially separated or purified away from other biological components in the environment (such as a cell) in which the component naturally occurs, such as other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a detectable label.

The terms "conjugating," "joining," "bonding" or "linking" refer to making two polypeptides into one contiguous polypeptide molecule, or to covalently attaching a radionuclide or other molecule to a polypeptide, such as a scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Parenteral: Refers to administration other than through the alimentary canal (the digestive tract), such as by subcutaneous, intramuscular, intrasternal or intravenous administration.

Pathologic hypercoagulation: A hereditary or acquired condition, disorder, or state comprising pathologically fast or excessive blood clotting or increased tendency for clotting, such as that seen in disseminated intravascular coagulation, heart attacks, stroke, coronary artery disease, deep vein thrombosis, thromboembolic disease, pulmonary embolisms, vascular disease, surgery, trauma, malignancy, presence of vascular prosthetic devices, general anesthesia, pregnancy, use of oral contraceptives, systemic lupus erythematosus, infections, sepsis, diabetes, autoimmune disease, pancreatitis, cirrhosis, diverticulitis, antiphospholipid antibody syndrome, activated protein C resistance, protein C deficiency, protein S deficiency, elevated coagulation factor VIII levels, sticky platelet syndrome, homocystindemia, antithrombin deficiency, dysfibrinolysis, a prothrombin G20210A mutation, and thrombomodulin mutations.

Pharmaceutically acceptable carriers: The pharmaceutically acceptable carriers of use are conventional. *Remington: The Science and Practice of Pharmacy*, The University of the Sciences in Philadelphia, Editor, Lippincott, Williams, & Wilkins, Philadelphia, PA, 21$^{st}$ Edition (2005), describes compositions and formulations suitable for pharmaceutical delivery of the antibodies disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a $V_H$ of an antibody that specifically binds a FXII polypeptide are typically characterized by possession of at least about 75%, for example at least about 80%, 90%, 95%, 96%, 97%, 98% or 99% sequence identity counted over the full-length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Solid tumor cancer: A type of cancer that forms an abnormal mass of tissues, usually without cysts or liquid areas, including sarcomas, carcinomas, and lymphomas. Solid tumor cancers may include cancers of the pancreas, breast, ovary, prostate, bone, bladder, cervix, colon & rectum, endometrium, kidney, lips & oral cavity, brain, kidney, liver, skin, mesothelium, lung, and thyroid, or metastasis thereof.

Subject: Living multi-cellular vertebrate organisms, a category that includes both human and veterinary subjects, including human and non-human mammals. In some embodiments, a subject is any mammal, such as a human, non-human primate or veterinary subject such as a dog.

Synthetic: Produced by artificial means in a laboratory, for example, a synthetic nucleic acid or protein (for example, an antibody) can be chemically synthesized in a laboratory.

Therapeutically effective amount (or pharmaceutically effective amount): Quantity of a specific substance sufficient to achieve the desired effect in a subject being treated. For instance, this can be the amount necessary to inhibit activation of factor XII. The terms may also indicate an amount of an anti-FMII monoclonal antibody or of a combination of such antibody with another anticoagulant or antithrombotic agent that is needed to effectively inhibit thrombosis in vivo or otherwise cause a measurable benefit in vivo to a patient in need. When administered to a subject, a dosage will generally be used that will achieve target tissue concentrations that have been shown to achieve a desired in vitro effect. The precise amount will depend upon numerous factors, including, but not limited to the components and physical characteristics of the therapeutic composition, intended patient population, individual patient considerations, and the like, and can readily be determined by one skilled in the art.

Thrombosis: The formation or presence of a clot (also called a "thrombus") inside a blood vessel, obstructing the flow of blood through the circulatory system. Thrombosis is usually caused by abnormalities in blood composition, quality of the vessel wall, and/or nature of the blood flow. The formation of a clot is often caused by an injury to the vessel wall (such as from trauma or infection) and by the slowing or stagnation of blood flow past the point of injury. In some cases, abnormalities in coagulation cause thrombosis. A clot that breaks free and begins to travel around the body is known as an embolus. When a thrombus occupies more than 75% of the cross-sectional area of the lumen of an artery, blood flow to the tissue supplied is reduced enough to cause symptoms because of decreased oxygen (hypoxia) and accumulation of metabolic products like lactic acid. More than 90% obstruction can result in anoxia, the complete deprivation of oxygen, and infarction, a mode of cell death. Thromboembolism is the combination of thrombosis and its main complication, embolism.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. FXII-Specific Monoclonal Antibodies

Disclosed herein are monoclonal antibodies, such as mouse monoclonal antibody 5C12 (also referred to herein as "AB053"), or humanized versions thereof (referred to as "humanized 5C12," "h5C12" or "AB054"), that bind human blood protein factor XII (FXII). The antibodies (or antigen-binding fragments thereof) are capable of forming immune complexes with FXII and inhibit activity of FXII. Administration of the disclosed antibodies inhibits inflammation and thrombosis, and thus can be used to treat diseases and disorders characterized by pathologic activation of FXII.

The amino acid sequence of the 5C12 heavy chain, the 5C12 VH domain, the 5C12 light chain and the 5C12 VL domain are provided below. In the VH and VL domain sequences, the location of each CDR according to IMGT is indicated by underline. One of skill in the art could readily determine the CDR boundaries using any other numbering scheme, such as the Kabat or Chothia numbering schemes. Underlined residues in the heavy chain and light chain sequences indicate constant domains. cDNA sequences of the heavy and light chain are also provided.

```
5C12 Heavy Chain (SEQ ID NO: 1):
DVQLQESGPDLVKPSQSLSLTCTVTGYSITSGYSWHWIRQFPGNNLEWMG

YIQYSGNTNSNPSLKSRISITRDTSKNQFFLHLNSVTTEDTATYYCARWG

SFDYWGQGTTLTVSSAKTTPPSVYPLAPGSAAQTNSMVTLGCLVKGYFPE

PVTVTWNSGSLSSGVHTFPAVLQSDLYTLSSSVTVPSSTWPSETVTCNVA

HPASSTKVDKKIVPRDCGCKPCICTVPEVSSVFIFPPKPKDVLTITLTPK

VTCVVVDISKDDPEVQFSWFVDDVEVHTAQTQPREEQFNSTFRSVSELPI

MHQDWLNGKEFKCRVNSAAFPAPIEKTISKTKGRPKAPQVYTIPPPKEQM

AKDKVSLTCMITDFFPEDITVEWQWNGQPAENYKNTQPIMDTDGSYFVYS

KLNVQKSNWEAGNTFTCSVLHEGLHNHHTEKSLSHSPGK

5C12 VH Domain (SEQ ID NO: 2):
DVQLQESGPDLVKPSQSLSLTCTVTGYSITSGYSWHWIRQFPGNNLEWMG

YIQYSGNTNSNPSLKSRISITRDTSKNQFFLHLNSVTTEDTATYYCARWG

SFDYWGQGTTLTVSS

CDR1:
(residues 26-34 of SEQ ID NO: 2)
GYSITSGYS

CDR2:
(residues 52-58 of SEQ ID NO: 2)
IQYSGNT

CDR3:
(residues 97-104 of SEQ ID NO: 2)
ARWGSFDY

5C12 Light Chain(SEQ ID NO: 3):
QIVLTQSPAIMSASPGEKVTMTCSASSSVNYMEIWYQQKSGTSPKRWIYD

TSKLASGVPARFSGSGSGTSYSLTISSMEAGDAATYYCQQWSGNPPTFGG
```

-continued

GTILEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC

5C12 VL Domain (SEQ ID NO: 4):
QIVLTQSPAIMSASPGEKVTMTCSASSSVNYMHWYQQKSGTSPKRWIYDT

SKLASGVPARFSGSGSGTSYSLTISSMEAGDAATYYCQQWSGNPPTFGGG

TILEIK

CDR1:
(residues 27-31 of SEQ ID NO: 4)
SSVNY

CDR2:
(residues 49-51 of SEQ ID NO: 4)
DTS

CDR3:
(residues 88-96 of SEQ ID NO: 4)
QQWSGNPPT

5C12 heavy chain cDNA sequence (SEQ ID NO: 5)
GATGTGCAGCTTCAGGAGTCAGGACCTGACCTGGTGAAACCTTCTCAGTC

ACTTTCACTCACCTGCACTGTCACTGGCTACTCCATCACCAGTGGTTATA

GCTGGCACTGGATCCGGCAGTTTCCAGGAAACAATCTGGAATGGATGGGC

TACATACAGTACAGTGGTAACACTAATTCCAACCCATCTCTCAAAAGTCG

AATCTCTATCACTCGAGACACATCCAAGAACCAGTTCTTCCTGCATTTGA

ATTCTGTGACTACTGAGGACACAGCCACATATTATTGTGCAAGATGGGGG

TCCTTTGACTACTGGGGCCAAGGCACCACTCTCACAGTCTCCTCAGCCAA

AACGACACCCCCATCTGTCTATCCACTGGCCCCTGGATCTGCTGCCCAAA

CTAACTCCATGGTGACCCTGGGATGCCTGGTCAAGGGCTATTTCCCTGAG

CCAGTGACAGTGACCTGGAACTCTGGATCCCTGTCCAGCGGTGTGCACAC

CTTCCCAGCTGTCCTGCAGTCTGACCTCTACACTCTGAGCAGCTCAGTGA

CTGTCCCCTCCAGCACCTGGCCCAGCGAGACCGTCACCTGCAACGTTGCC

CACCCGGCCAGCAGCACCAAGGTGGACAAGAAAATTGTGCCCAGGGATTG

TGGTTGTAAGCCTTGCATATGTACAGTCCCAGAGGTATCATCTGTCTTCA

TCTTCCCCCCAAAGCCCAAGGATGTGCTCACCATTACTCTGACTCCTAAG

GTCACGTGTGTTGTGGTAGACATCAGCAAGGATGATCCCGAGGTCCAGTT

CAGCTGGTTTGTAGATGATGTGGAGGTGCACACAGCTCAGACGCAACCCC

GGGAGGAGCAGTTCAACAGCACTTTCCGCTCAGTCAGTGAACTTCCCATC

ATGCACCAGGACTGGCTCAATGGCAAGGAGTTCAAATGCAGGGTCAACAG

TGCAGCTTTCCCTGCCCCCATCGAGAAAACCATCTCCAAAACCAAAGGCA

GACCGAAGGCTCCACAGGTGTACACCATTCCACCTCCCAAGGAGCAGATG

GCCAAGGATAAAGTCAGTCTGACCTGCATGATAACAGACTTCTTCCCTGA

AGACATTACTGTGGAGTGGCAGTGGAATGGGCAGCCAGCGGAGAACTACA

AGAACACTCAGCCCATCATGGACACAGATGGCTCTTACTTCGTCTACAGC

AAGCTCAATGTGCAGAAGAGCAACTGGGAGGCAGGAAATACTTTCACCTG

CTCTGTGTTACATGAGGGCCTGCACAACCACCATACTGAGAAGAGCCTCT

CCCACTCTCCTGGTAAA

5C12 light chain cDNA sequence (SEQ ID NO: 6)
CAAATTGTTCTCACCCAGTCTCCAGCTATCATGTCTGCATCTCCAGGGGA

GAAGGTCACCATGACCTGCAGTGCCAGCTCAAGTGTAAATTACATGCACT

GGTACCAGCAGAAGTCAGGCACCTCCCCCAAAAGATGGATTTATGACACA

TCCAAACTGGCTTCTGGAGTCCCTGCTCGCTTCAGTGGCAGTGGGTCTGG

GACCTCTTACTCTCTCACAATCAGCAGCATGGAGGCTGGAGATGCTGCCA

CTTATTACTGCCAGCAGTGGAGTGGTAACCCACCGACGTTCGGTGGAGGC

ACCATACTGGAAATCAAACGGGCTGATGCTGCACCAACTGTATCCATCTT

CCCACCATCCAGTGAGCAGTTAACATCTGGAGGTGCCTCAGTCGTGTGCT

TCTTGAACAACTTCTACCCCAAAGACATCAATGTCAAGTGGAAGATTGAT

GGCAGTGAACGACAAAATGGCGTCCTGAACAGTTGGACTGATCAGGACAG

CAAAGACAGCACCTACAGCATGAGCAGCACCCTCACGTTGACCAAGGACG

AGTATGAACGACATAACAGCTATACCTGTGAGGCCACTCACAAGACATCA

ACTTCACCCATTGTCAAGAGCTTCAACAGGAATGAGTGT

Humanized heavy chain and light chain sequences were generated for antibody 5C12. h5C12 heavy chain, light chain, VH domain and VL domain sequences are shown below.

Humanized 5C12 Heavy Chain
("HC1" SEQ ID NO: 7)
QVQLQESGPGLVKPSQTLSLTCTVSGYSITSGYSWHWIRQHPGKGLEWIG

YIQYSGNTNSNPSLKSRVTISRDTSKNQFSLKLSSVTAADTAVYYCARWG

SFDYWGQGTLVTVSSASTKGPSVFPLAPCSRSTSESTAALGCLVKDYFPE

PVTVSWNSGALTSGVHTFPAVLQSSGLYSLSSVVTVPSSSLGTKTYTCNV

DHKPSNTKVDKRVESKYGPPCPPCPAPEFLGGPSVFLFPPKPKDTLMISR

TPEVTCVVVDVSQEDPEVQFNWYVDGVEVHNAKTKPREEQFNSTYRVVSV

LTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFF

LYSRLTVDKSRWQEGNVFSCSVMHEALHNHYTQKSLSLSLG

Humanized 5C12 (HC1) VH Domain
(SEQ ID NO: 8)
QVQLQESGPGLVKPSQTLSLTCTVSGYSITSGYSWHWIRQHPGKGLEWIG

YIQYSGNTNSNPSLKSRVTISRDTSKNQFSLKLSSVTAADTAVYYCARWG

SFDYWGQGTLVTVSS

CDR1:
(residues 26-34 of SEQ ID NO: 8)
GYSITSGYS

CDR2:
(residues 52-58 of SEQ ID NO: 8)
IQYSGNT

CDR3:
(residues 97-104 of SEQ ID NO: 8)
ARWGSFDY

Humanized 5C12 Light Chain
("LC1" SEQ ID NO: 9)
EIVLTQSPATLSLSPGERATLSCRASSSVNYLHWYQQKPGQAPRRLIYDT

SKLATGIPARFSGSGSGTDYTLTISSLEPEDFAVYYCQQWSGNPPTFGGG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL
SSPVTKSFNRGEC

Humanized 5C12 (LC1) VL domain (SEQ ID NO: 10)
EIVLTQSPATLSLSPGERATLSCRASSSVNYLHWYQQKPGQAPRRLIYDT
SKLATGIPARFSGSGSGTDYTLTISSLEPEDFAVYYCQQWSGNPPTFGGG
TKVEIK CDR1:
(residues 27-31 of SEQ ID NO: 10)
SSVNY CDR2:
(residues 49-51 of SEQ ID NO: 10)
DTS CDR3:
(residues 88-96 of SEQ ID NO: 10)
QQWSGNPPT Humanized 5C12 heavy chain (HC1) cDNA sequence
(SEQ ID NO: 11)
CAGGTGCAGCTCCAGGAGAGCGGACCCGGTCTGGTGAAGCCCAGCCAGAC
CCTGAGCCTGACCTGCACCGTGAGCGGCTACTCAATCACCTCTGGCTACA
GCTGGCACTGGATCAGGCAGCACCCCGGCAAGGGCCTGGAGTGGATTGGC
TATATCCAGTACAGCGGCAACACCAACAGCAACCCCAGCCTCAAGAGCAG
GGTGACCATCAGCAGGGATACAAGCAAGAACCAGTTCAGCCTGAAGCTGA
GCAGCGTGACCGCCGCTGACACCGCCGTGTACTACTGCGCCAGGTGGGGC
AGCTTCGACTACTGGGGCCAGGGCACCCTGGTGACCGTGTCTTCTGCTAG
CACCAAGGGCCCCAGCGTGTTTCCTCTCGCTCCCTGCAGCCGGAGCACAT
CCGAGAGCACCGCTGCTCTGGGCTGTCTCGTGAAGGACTACTTCCCTGAA
CCCGTCACCGTCAGCTGGAATAGCGGCGCCCTGACATCCGGCGTCCACAC
ATTCCCCGCTGTCCTGCAGAGCAGCGGCCTGTACAGCCTGAGCTCCGTGG
TCACCGTGCCTAGCAGCAGCCTGGGAACAAAGACCTACACCTGCAACGTG
GACCATAAGCCCTCCAACACCAAGGTGGACAAGCGGGTGGAATCCAAGTA
TGGACCCCCCTGTCCTCCTTGCCCTGCTCCTGAATTTCTCGGAGGCCCCT
CCGTCTTCCTGTTTCCCCCCAAGCCCAAGGACACCCTGATGATCTCCCGG ACACCCGAAGTCACCTGCGTCGTGGTGGATGTCAGCCAGGAAGATCCCGA
GGTGCAGTTCAACTGGTACGTGGACGGAGTGGAGGTGCATAACGCCAAAA
CCAAGCCCAGGGAAGAGCAGTTCAACAGCACCTATCGGGTCGTGTCCGTG
CTCACCGTCCTGCATCAGGATTGGCTCAACGGCAAGGAGTACAAGTGCAA
GGTGTCCAACAAGGGCCTGCCCTCCTCCATCGAGAAGACCATCTCCAAGG
CTAAGGGCCAACCTCGGGAGCCCCAAGTGTATACCCTCCCTCCCAGCCAG
GAGGAGATGACCAAGAATCAAGTGAGCCTGACCTGCCTCGTGAAGGGATT
TTACCCCTCCGACATCGCTGTGGAATGGGAAAGCAATGGCCAACCTGAGA
ACAACTACAAGACCACACCCCCGTGCTGGACTCCGATGGCTCCTTCTTC
CTGTACAGCAGGCTGACCGTGGACAAATCCCGGTGGCAAGAGGGAAACGT
GTTCAGCTGCTCCGTGATGCACGAGGCTCTCCACAACCACTACACCCAGA
AGAGCCTCTCCCTGAGCCTCGGCTAGTAA Humanized 5C12 light chain (LC1) cDNA sequence
(SEQ ID NO: 12)
GAGATCGTGCTGACCCAGAGCCCAGCAACCCTGAGCTTGAGCCCCGGTGA
GAGGGCCACCCTGTCATGCAGGGCCAGCAGCAGCGTGAACTACCTGCACT
GGTATCAGCAGAAGCCCGGTCAAGCCCCAGGAGGCTGATCTACGACACC
AGCAAGCTGGCCACCGGCATCCCCGCCAGGTTTTCCGGCAGCGGGTCAGG
CACCGACTACACCCTCACCATAAGCAGCCTGGAGCCCGAGGACTTCGCCG
TGTACTACTGTCAGCAGTGGAGCGGCAACCCACCTACCTTTGGCGGAGGC
ACTAAGGTGGAGATCAAGCGGACCGTGGCCGCCCCCAGCGTGTTCATCTT
CCCTCCCAGCGACGAGCAGCTGAAGTCTGGCACCGCCAGCGTGGTGTGCC
TGCTGAACAACTTCTACCCCCGCGAGGCCAAGGTGCAGTGGAAGGTGGAC
AACGCCCTGCAGAGCGGCAACAGCCAGGAGAGCGTGACCGAGCAGGACTC
CAAGGACAGCACCTACAGCCTGAGCAGCACCCTGACCCTGAGCAAGGCCG
ACTACGAGAAGCACAAGGTGTACGCCTGCGAGGTGACCCACCAGGGACTG
TCTAGCCCCGTGACCAAGAGCTTCAACCGGGGCGAGTGCTAA An alignment of the mouse ("Murine") and humanized ("Human") 5C12 heavy chain and light chain amino acid sequences are shown below. Amino acid residues shared between the mouse and humanized versions are indicated by a star.

Heavy Chain Alignment
CLUSTAL O(1.2.4) multiple sequence alignment

```
Murine  DVQLQESGPDLVKPSQSLSLTCTVTGYSITSGYSWHWIRQFPGNNLEWMGYIQYSGNTNS  60
Human   QVQLQESGPGLVKPSQTLSLTCTVSGYSITSGYSWHWIRQHPGKGLEWIGYIQYSGNTNS  60
        :*******.******:*******:************:**::***:***********

Murine  NPSLKSRISITRDTSKNQFFLHLNSVTTEDTATYYCARWGSFDYWGQGTTLTVSSAKTTP  120
Human   NPSLKSRVTISRDTSKNQFSLKLSSVTAADTAVYYCARWGSFDYWGQGTLVTVSSASTKG  120
        *******::*:******* *:*.***::***.*******************.:*****.*.

Murine  PSVYPLAPGSAAQTNSMVTLGCLVKGYFPEPVTVTWNSGSLSSGVHTFPAVLQS-DLYTL  179
Human   PSVFPLAPCSRSTSESTAALGCLVMDYFPEPVTVSWNSGALTSGVHTFPAVLQSSGLYSL  180
        ***:**** *  :: :*  .:******* ********:*.*:************ .**:*

Murine  SSSVTVPSSTWPSETVTCNVAHPASSTKVDKKIVPRD-CGCKPCICT-VPDVSSVFIFPP  237
Human   SSVVTVPSSSLGTKTYTCNVDHMPSNTKVDKRVESKYGPPCPPCPAPEFLGGPSVFLFDP  240
        **.******:   ::.* **** *.*.*****::   *  * **     *   ***:*:*
```

```
Murine  KPKDVLTITLTPKVTCVVVDISKDDPEVQFSWFVDDVEVHTAQTQPREEQFNSTERSVSE  297
Human   KPKDTLMISRTPEVTCVVVDVSQEDPEVQFNWYVDGVEVHNAKTKPREEQFNSTYRVVSV  300
        ****.*  *: **.*******.*:.******.*.**.****.*.*:*********.*  **

Murine  LPIMHQDWLNGKEFMCRVMSAAFPAPIEKTISKTMGRPKAPQVYTIPPPKEQMAKDKVSL  357
Human   LTVLHQDWLNGKEYMCKVSNKSLPSSIEKTISKAMGQPREPQVYTLPPSQEEMTKNQVSL  360
        * :;*********:**:*.. ..:*: *******:**:*: *****.** :*:*:*::***

Murine  TCMITDFFPEDITVEWQWNGQPAENYKNTQPIMDTDGSYFVYSKLNVQKSNWEAGNTFTC  417
Human   TCLVKGFYPSDIAVEWESNGQPENNYKTTPEVLDSDGSFFLYSRLTVDMSRWQEGNVFSC  420
        **::..*:*.** .***. **** .***.* *::*** :*:**.*.*.**.*: **.*:*

Murine  SVLHEGLHNHHTEKSLSHSPGK                                       439  (SEQ ID NO: 1)
Human   SVMHEALHNHYTQKSLSLSLG-                                       441  (SEQ ID NO: 7)
        **:**.****:*:**** * *
```

Light Chain Alignment

```
Murine  QIVLTQSPAIMSASPGEKVTMTCSASSSVNYMHWYQQKSGTSPKRWIYDTSKLASGVPAR  60
Human   EIVITQSPATLSLSPGERATLSCRASSSVNYLHWYQQKPGQAPPRLIYDTSKLATGIPAR  60
        :********  :* ****:.*::.* *******:****** *  :*.* ********:*:.***

Murine  FSGSGSGTSYSLTISSMEAGDAATYYCQQWSGNPPTEGGGTILEIKRADAAPTVSIFPPS  120
Human   FSGSGSGTDYTLTISSLEPEDFAVYYCQQWSGNPPTEGGGTKVEIKRTVAAPSVFIFPPS  120
        ********.*:*****:* * *.*******************  :****: ***.* *****

Murine  SEQLTSGGASVVCFLNNEYPKDINVKWKIDGSERQNGVLNSWTDQDSKDSTYSMSSTLTL  180
Human   DEQLKSGTASVVCLLNNEYPREAKVQWKVDNALQSGNSQESVTEQDSKDSTYSLSSTLTL  180
        .***.**.*****.*******:: .*:**.*:. :.... :* *:*********:******

Murine  TKDEYERHNSYTCEATHKTSTSPIVKSFNRNEC                            213  (SEQ ID NO: 3)
Human   SKADYEKHKVYACEVTHQGLSSPVTKSFNRGEC                            213  (SEQ ID NO: 9)
        :*  :**:*: *:**.**:   :**:.*****.**
```

Alternative Humanized Heavy Chain and Light Chain Sequences

During the humanization process, a total of three humanized heavy chain (HC1, HC2, HC3) and three humanized light chain (LC1, LC2, LC3) sequences were developed. Humanized antibodies comprising all nine possible combinations of the humanized heavy and light chains were generated and tested: (1) HC1+LC1; (2) HC1+LC2; (3) HC1+LC3; (4) HC2+LC1; (5) HC2+LC2; (6) HC2+LC3; (7) HC3+LC1; (8) HC3+LC2; and (9) HC3+LC3. All tested antibodies exhibited similar binding affinity for FXII and had similar FXII inhibitory activity (as determined by aPTT assay).

The humanized 5C12 antibody (also referred to as "AB054") is comprised of HC1+LC1 (SEQ ID NOs: 8 and 10). The heavy chain, VH domain, light chain, VL domain and cDNA sequences for HC2, HC3, LC2 and LC3 are shown below. The CDR sequences of murine 5C12 HC, humanized 5C12 HC, HC2 and HC3 are identical, and the CDR sequences of murine 5C12 LC, humanized 5C12 LC, LC2 and LC3 are identical; only framework residues vary amongst the different heavy and light chain sequences.

```
HC2 heavy chain
                                                  (SEQ ID NO: 13)
DVQLQESGPGLVKPSQTLSLTCTVTGYSITSGYSWHWIRQHPGKGLEWMGYIQYSGNTNSNP

SLKSRVTISRDTSKNQFSLKLSSVTAADTAVYYCARWGSFDYWGQGTLVTVSSASTKGPSVF

PLAPCSRSTSESTAALGCLVKDYFPEPVTVSWNSGALTSGVHTFPAVLQSSGLYSLSSVVTV

PSSSLGTKTYTCNVDHKPSNTKVDKRVESKYGPPCPPCPAPEFLGGPSVFLFPPKPKDTLMI

SRTPEVTCVVVDVSQEDPEVQFNWYVDGVEVHNAKTKPREEQFNSTYRVVSVLTVLHQDWLN

GKEYKCKVSNKGLPSSIEKTISKAKGQPREPQVYTLPPSQEEMTKNQVSLTCLVKGFYPSDI

AVEWESNGQPENNYKTTPPVLDSDGSFFLYSRLTVDKSRWQEGNVFSCSVMHEALHNHYTQK

SLSLSLG

HC2 VH domain
                                                  (SEQ ID NO: 14)
DVQLQESGPGLVKPSQTLSLTCTVTGYSITSGYSWHWIRQHPGKGLEWMGYIQYSGNTNSNP

SLKSRVTISRDTSKNQFSLKLSSVTAADTAVYYCARWGSFDYWGQGTLVTVSS

CDR1:
                                        (residues 26-34 of SEQ ID NO: 14)
GYSITSGYS
```

-continued

CDR2:
(residues 52-58 of SEQ ID NO: 14)
IQYSGNT

CDR3:
(residues 97-104 of SEQ ID NO: 14)
ARWGSFDY

HC3 heavy chain
(SEQ ID NO: 15)
DVQLQESGPGLVKPSETLSLTCTVSGYSITSGYSWHWIRQPPGKGLEWIGYIQYSGNTNSNP

SLKSRVTISRDTSKNQFSLRLSSVTAADTAVYYCARWGSFDYWGQGTMVTVSSASTKGPSVF

PLAPCSRSTSESTAALGCLVKDYFPEPVTVSWNSGALTSGVHTFPAVLQSSGLYSLSSVVTV

PSSSLGTKTYTCNVDHKPSNTKVDKRVESKYGPPCPPCPAPEFLGGPSVFLFPPKPKDTLMI

SRTPEVTCVVVDVSQEDPEVQFNWYVDGVEVHNAKTKPREEQFNSTYRVVSVLTVLHQDWLN

GKEYKCKVSNKGLPSSIEKTISKAKGQPREPQVYTLPPSQEEMTKNQVSLTCLVKGFYPSDI

AVEWESNGQPENNYKTTPPVLDSDGSFFLYSRLTVDKSRWQEGNVFSCSVMHEALHNHYTQK

SLSLSLG

HC3 VH domain
(SEQ ID NO: 16)
DVQLQESGPGLVKPSETLSLTCTVSGYSITSGYSWHWIRQPPGKGLEWIGYIQYSGNTNSNP

SLKSRVTISRDTSKNQFSLRLSSVTAADTAVYYCARWGSFDYWGQGTMVTVSS

CDR1:
(residues 26-34 of SEQ ID NO: 16)
GYSITSGYS

CDR2:
(residues 52-58 of SEQ ID NO: 16)
IQYSGNT

CDR3:
(residues 97-104 of SEQ ID NO: 16)
ARWGSFDY

LC2 light chain
(SEQ ID NO: 17)
EIVLTQSPATLSLSPGERATLSCRASSSVNYLHWYQQKPGQAPKRWIYDTSKLATGIPARFS

GSGSGTDYTLTISSLEPEDFAVYYCQQWSGNPPTFGGGTKVEIKRTVAAPSVFIFPPSDEQL

KSGTASVVCLLNNFYPREAKVQWKVDNALQSGNSQESVTEQDSKDSTYSLSSTLTLSKADYE

KHKVYACEVTHQGLSSPVTKSFNRGEC

LC2 VL domain
(SEQ ID NO: 18)
EIVLTQSPATLSLSPGERATLSCRASSSVNYLHWYQQKPGQAPKRWIYDTSKLATGIPARFS

GSGSGTDYTLTISSLEPEDFAVYYCQQWSGNPPTFGGGTKVEIK

CDR1:
(residues 27-31 of SEQ ID NO: 18)
SSVNY

CDR2:
(residues 49-51 of SEQ ID NO: 18)
DTS

CDR3:
(residues 88-96 of SEQ ID NO: 18)
QQWSGNPPT

LC3 light chain
(SEQ ID NO: 19)
DIVLTQTPATLSLSPGERATLSCRASSSVNYLHWYQQKPGQAPKRLIYDTSKLATGIPARFS

GSGSGTDYTLTISSLEPEDFAVYYCQQWSGNPPTFGQGTRLEIKRTVAAPSVFIFPPSDEQL

KSGTASVVCLLNNFYPREAKVQWKVDNALQSGNSQESVTEQDSKDSTYSLSSTLTLSKADYE

KHKVYACEVTHQGLSSPVTKSFNRGEC

-continued

LC3 VL domain
(SEQ ID NO: 20)
DIVLTQTPATLSLSPGERATLSCRASSSVNYLHWYQQKPGQAPKRLIYDTSKLATGIPARFS

GSGSGTDYTLTISSLEPEDFAVYYCQQWSGNPPTFGQGTRLEIK

CDR1:
(residues 27-31 of SEQ ID NO: 20)
SSVNY

CDR2:
(residues 49-51 of SEQ ID NO: 20)
DTS

CDR3:
(residues 88-96 of SEQ ID NO: 20)
QQWSGNPPT

HC2 heavy chain cDNA sequence
(SEQ ID NO: 21)
GACGTGCAGCTCCAGGAGAGCGGACCCGGTCTGGTGAAGCCCAGCCAGACCCTGAGCCTGAC

CTGCACCGTGACCGGCTACTCAATCACCTCTGGCTACAGCTGGCACTGGATCAGGCAGCACC

CCGGCAAGGGCCTGGAGTGGATGGGCTATATCCAGTACAGCGGCAACACCAACAGCAACCCC

AGCCTCAAGAGCAGGGTGACCATCAGCAGGGATACAAGCAAGAACCAGTTCAGCCTGAAGCT

GAGCAGCGTGACCGCCGCTGACACCGCCGTGTACTACTGCGCCAGGTGGGGCAGCTTCGACT

ACTGGGGCCAGGGCACCCTGGTGACCGTGTCTTCTGCTAGCACCAAGGGCCCCAGCGTGTTT

CCTCTCGCTCCCTGCAGCCGGAGCACATCCGAGAGCACCGCTGCTCTGGGCTGTCTCGTGAA

GGACTACTTCCCTGAACCCGTCACCGTCAGCTGGAATAGCGGCGCCCTGACATCCGGCGTCC

ACACATTCCCCGCTGTCCTGCAGAGCAGCGGCCTGTACAGCCTGAGCTCCGTGGTCACCGTG

CCTAGCAGCAGCCTGGGAACAAAGACCTACACCTGCAACGTGGACCATAAGCCCTCCAACAC

CAAGGTGGACAAGCGGGTGGAATCCAAGTATGGACCCCCCTGTCCTCCTTGCCCTGCTCCTG

AATTTCTCGGAGGCCCCTCCGTCTTCCTGTTTCCCCCCAAGCCCAAGGACACCCTGATGATC

TCCCGGACACCCGAAGTCACCTGCGTCGTGGTGGATGTCAGCCAGGAAGATCCCGAGGTGCA

GTTCAACTGGTACGTGGACGGAGTGGAGGTGCATAACGCCAAAACCAAGCCCAGGGAAGAGC

AGTTCAACAGCACCTATCGGGTCGTGTCCGTGCTCACCGTCCTGCATCAGGATTGGCTCAAC

GGCAAGGAGTACAAGTGCAAGGTGTCCAACAAGGGCCTGCCCTCCTCCATCGAGAAGACCAT

CTCCAAGGCTAAGGGCCAACCTCGGGAGCCCCAAGTGTATACCCTCCCTCCCAGCCAGGAGG

AGATGACCAAGAATCAAGTGAGCCTGACCTGCCTCGTGAAGGGATTTTACCCCTCCGACATC

GCTGTGGAATGGGAAAGCAATGGCCAACCTGAGAACAACTACAAGACCACACCCCCCGTGCT

GGACTCCGATGGCTCCTTCTTCCTGTACAGCAGGCTGACCGTGGACAAATCCCGGTGGCAAG

AGGGAAACGTGTTCAGCTGCTCCGTGATGCACGAGGCTCTCCACAACCACTACACCCAGAAG

AGCCTCTCCCTGAGCCTCGGCTAGTAA

LC2 light chain cDNA sequence
(SEQ ID NO: 22)
GAGATCGTGCTGACCCAGAGCCCAGCAACCCTGAGCTTGAGCCCCGGTGAGAGGGCCACCCT

GTCATGCAGGGCCAGCAGCAGCGTGAACTACCTGCACTGGTATCAGCAGAAGCCCGGTCAAG

CCCCCAAGAGGTGGATCTACGACACCAGCAAGCTGGCCACCGGCATCCCCGCCAGGTTTTCC

GGCAGCGGGTCAGGCACCGACTACACCCTCACCATAAGCAGCCTGGAGCCCGAGGACTTCGC

CGTGTACTACTGTCAGCAGTGGAGCGGCAACCCACCTACCTTTGGCGGAGGCACTAAGGTGG

AGATCAAGCGGACCGTGGCCGCCCCCAGCGTGTTCATCTTCCCTCCCAGCGACGAGCAGCTG

AAGTCTGGCACCGCCAGCGTGGTGTGCCTGCTGAACAACTTCTACCCCCGCGAGGCCAAGGT

-continued

```
GCAGTGGAAGGTGGACAACGCCCTGCAGAGCGGCAACAGCCAGGAGAGCGTGACCGAGCAGG

ACTCCAAGGACAGCACCTACAGCCTGAGCAGCACCCTGACCCTGAGCAAGGCCGACTACGAG

AAGCACAAGGTGTACGCCTGCGAGGTGACCCACCAGGGACTGTCTAGCCCCGTGACCAAGAG

CTTCAACCGGGGCGAGTGCTAA
```

HC3 heavy chain cDNA sequence (SEQ ID NO: 23)
```
GACGTGCAGCTCCAGGAGAGCGGACCCGGTCTGGTGAAGCCCAGCGAGACCCTGAGCCTGAC

CTGCACCGTGAGCGGCTACTCAATCACCTCTGGCTACAGCTGGCACTGGATCAGGCAGCCAC

CCGGCAAGGGCCTGGAGTGGATTGGCTATATCCAGTACAGCGGCAACACCAACAGCAACCCC

AGCCTCAAGAGCAGGGTGACCATCAGCAGGGATACAAGCAAGAACCAGTTCAGCCTGAGGCT

GAGCAGCGTGACCGCCGCTGACACCGCCGTGTACTACTGCGCCAGGTGGGGCAGCTTCGACT

ACTGGGGCCAGGGCACCATGGTGACCGTGTCTTCTGCTAGCACCAAGGGCCCCAGCGTGTTT

CCTCTCGCTCCCTGCAGCCGGAGCACATCCGAGAGCACCGCTGCTCTGGGCTGTCTCGTGAA

GGACTACTTCCCTGAACCCGTCACCGTCAGCTGGAATAGCGGCGCCCTGACATCCGGCGTCC

ACACATTCCCCGCTGTCCTGCAGAGCAGCGGCCTGTACAGCCTGAGCTCCGTGGTCACCGTG

CCTAGCAGCAGCCTGGGAACAAAGACCTACACCTGCAACGTGGACCATAAGCCCTCCAACAC

CAAGGTGGACAAGCGGGTGGAATCCAAGTATGGACCCCCCTGTCCTCCTTGCCCTGCTCCTG

AATTTCTCGGAGGCCCCTCCGTCTTCCTGTTTCCCCCCAAGCCCAAGGACACCCTGATGATC

TCCCGGACACCCGAAGTCACCTGCGTCGTGGTGGATGTCAGCCAGGAAGATCCCGAGGTGCA

GTTCAACTGGTACGTGGACGGAGTGGAGGTGCATAACGCCAAAACCAAGCCCAGGGAAGAGC

AGTTCAACAGCACCTATCGGGTCGTGTCCGTGCTCACCGTCCTGCATCAGGATTGGCTCAAC

GGCAAGGAGTACAAGTGCAAGGTGTCCAACAAGGGCCTGCCCTCCTCCATCGAGAAGACCAT

CTCCAAGGCTAAGGGCCAACCTCGGGAGCCCCAAGTGTATACCCTCCCTCCCAGCCAGGAGG

AGATGACCAAGAATCAAGTGAGCCTGACCTGCCTCGTGAAGGGATTTTACCCCTCCGACATC

GCTGTGGAATGGGAAAGCAATGGCCAACCTGAGAACAACTACAAGACCACACCCCCCGTGCT

GGACTCCGATGGCTCCTTCTTCCTGTACAGCAGGCTGACCGTGGACAAATCCCGGTGGCAAG

AGGGAAACGTGTTCAGCTGCTCCGTGATGCACGAGGCTCTCCACAACCACTACACCCAGAAG

AGCCTCTCCCTGAGCCTCGGCTAGTAA
```

LC3 light chain cDNA sequence (SEQ ID NO: 24)
```
GACATCGTGCTGACCCAGACCCCAGCAACCCTGAGCTTGAGCCCCGGTGAGAGGGCCACCCT

GTCATGCAGGGCCAGCAGCAGCGTGAACTACCTGCACTGGTATCAGCAGAAGCCCGGTCAAG

CCCCCAAGAGGCTGATCTACGACACCAGCAAGCTGGCCACCGGCATCCCCGCCAGGTTTTCC

GGCAGCGGGTCAGGCACCGACTACACCCTCACCATAAGCAGCCTGGAGCCCGAGGACTTCGC

CGTGTACTACTGTCAGCAGTGGAGCGGCAACCCACCTACCTTTGGCCAGGGCACTAGGTTGG

AGATCAAGCGGACCGTGGCCGCCCCCAGCGTGTTCATCTTCCCTCCCAGCGACGAGCAGCTG

AAGTCTGGCACCGCCAGCGTGGTGTGCCTGCTGAACAACTTCTACCCCCGCGAGGCCAAGGT

GCAGTGGAAGGTGGACAACGCCCTGCAGAGCGGCAACAGCCAGGAGAGCGTGACCGAGCAGG

ACTCCAAGGACAGCACCTACAGCCTGAGCAGCACCCTGACCCTGAGCAAGGCCGACTACGAG

AAGCACAAGGTGTACGCCTGCGAGGTGACCCACCAGGGACTGTCTAGCCCCGTGACCAAGAG

CTTCAACCGGGGCGAGTGCTAA
```

Provided herein are monoclonal antibodies or antigen-binding fragments that bind (such as specifically bind) FXII. In some embodiments, the monoclonal antibody or antigen-binding fragment includes both a VH domain and a VL domain.

In some embodiments, the monoclonal antibody or antigen-binding fragment that binds FXII includes at least one CDR sequence from antibody 5C12. In some embodiments, the CDR sequences are determined using the IMGT, Kabat or Chothia numbering scheme.

In some embodiments, the FXII-specific monoclonal antibody or antigen-binding fragment includes a VH domain and a VL domain, and the VH domain of the antibody includes one, two or all three CDR sequences of SEQ ID NO: 2 and/or the VL domain of the antibody includes one, two or all three CDR sequences of SEQ ID NO: 4. In some examples, the VH domain comprises residues 26-34, 52-58 and 97-104 of SEQ ID NO: 2 and the VL domain comprises residues 27-31, 49-51 and 88-96 of SEQ ID NO: 4.

In particular examples, the VH domain comprises the CDR sequences of SEQ ID NO: 2 and the amino acid sequence of the VH domain is at least 80%, at least 85%, at least 90%, at least 95%, at least 96%, at least 97%, at least 98% or at least 99% identical to SEQ ID NO: 2, SEQ ID NO: 8, SEQ ID NO: 14 or SEQ ID NO: 16; and the VL domain comprises the CDR sequences of SEQ ID NO: 4 and the amino acid sequence of the VL domain is at least 80%, at least 85%, at least 90%, at least 95%, at least 96%, at least 97%, at least 98% or at least 99% identical to SEQ ID NO: 4, SEQ ID NO: 10, SEQ ID NO: 18 or SEQ ID NO: 20. In specific non-limiting examples, the amino acid sequence of the VH domain comprises or consists of SEQ ID NO: 2, SEQ ID NO: 8, SEQ ID NO: 14 or SEQ ID NO: 16 and the amino acid sequence of the VL domain comprises or consists of SEQ ID NO: 4, SEQ ID NO: 10, SEQ ID NO: 18 or SEQ ID NO: 20. In one non-limiting example, the amino acid sequence of the VH domain comprises or consists of SEQ ID NO: 8 and the amino acid sequence of the VL domain comprises or consists of SEQ ID NO: 10.

In some embodiments, the monoclonal antibody or antigen-binding fragment includes a complete heavy chain and/or a complete light chain. In some examples, the heavy chain comprises the CDR sequences of SEQ ID NO: 2 and the amino acid sequence of the heavy chain is at least 80%, at least 85%, at least 90%, at least 95%, at least 96%, at least 97%, at least 98% or at least 99% identical to SEQ ID NO: 1, SEQ ID NO: 7, SEQ ID NO: 13 or SEQ ID NO: 15; and/or the light chain comprises the CDR sequence of SEQ ID NO: 4 and amino acid sequence of the light chain is at least 80%, at least 85%, at least 90%, at least 95%, at least 96%, at least 97%, at least 98% or at least 99% identical to SEQ ID NO: 3, SEQ ID NO: 9, SEQ ID NO: 17 or SEQ ID NO: 19. In specific non-limiting examples, the amino acid sequence of the heavy chain comprises or consists of SEQ ID NO: 1, SEQ ID NO: 7, SEQ ID NO: 13 or SEQ ID NO: 15; and/or the amino acid sequence of the light chain comprises or consists of SEQ ID NO: 3, SEQ ID NO: 9, SEQ ID NO: 17 or SEQ ID NO: 19. In one non-limiting example, the amino acid sequence of the heavy chain comprises or consists of SEQ ID NO: 7 and the amino acid sequence of the light chain comprises or consists of SEQ ID NO: 9.

The FXII-specific antigen-binding fragments can be, for example, a Fab fragment, an Fab' fragment, an F(ab)'$_2$ fragment, a single chain variable fragment (scFv) or a disulfide stabilized variable fragment (dsFv). In some embodiments, the antigen-binding fragment is a scFv.

FXII-specific monoclonal antibodies can be of any isotype, such as IgG, IgM, IgA, IgD or IgE. In some embodiments, the monoclonal antibody is an IgG.

In some embodiments, the monoclonal antibody or antigen-binding fragment is a humanized antibody or antigen-binding fragment. In some examples, the amino acid sequence of the VH domain of the humanized antibody comprises the CDR sequences of SEQ ID NO: 2 and is at least 80%, at least 85%, at least 90%, at least 95%, at least 96%, at least 97%, at least 98% or at least 99% identical to SEQ ID NO: 8; and/or the amino acid sequence of VL domain of the humanized antibody comprises the CDR sequence of SEQ ID NO: 4 and is at least 80%, at least 85%, at least 90%, at least 95%, at least 96%, at least 97%, at least 98% or at least 99% identical to SEQ ID NO: 10. In specific non-limiting examples, the amino acid sequence of the VH domain comprises or consists of SEQ ID NO: 8; and/or the amino acid sequence of the VL domain comprises or consists of SEQ ID NO: 10.

In some embodiments, the humanized monoclonal antibody or antigen-binding fragment includes a complete heavy chain and/or a complete light chain. In some examples, the heavy chain comprises the CDR sequence of SEQ ID NO: 2 and the amino acid sequence of the heavy chain is at least 80%, at least 85%, at least 90%, at least 95%, at least 96%, at least 97%, at least 98% or at least 99% identical to SEQ ID NO: 7; and/or the light chain comprises the CDR sequence of SEQ ID NO: 4 and the amino acid sequence of the light chain is at least 80%, at least 85%, at least 90%, at least 95%, at least 96%, at least 97%, at least 98% or at least 99% identical to SEQ ID NO: 9. In specific non-limiting examples, the amino acid sequence of the heavy chain comprises or consist of SEQ ID NO: 7; and/or the amino acid sequence of the light chain comprises or consists of SEQ ID NO: 9.

In some embodiments, the monoclonal antibody or antigen-binding fragment is a chimeric or synthetic antibody or antigen-binding fragment.

Also provided herein are fusion proteins that include a monoclonal antibody or antigen-binding fragment disclosed herein and a heterologous protein or peptide. In some embodiments, the heterologous protein is an Fc protein. In some examples, the Fc protein is a mouse Fc or a human Fc protein.

Further provided are antibody conjugates including a monoclonal antibody or antigen-binding fragment disclosed herein and a detectable label, such as, but not limited to, a fluorophore, an enzyme or a radioisotope.

Compositions that include a pharmaceutically acceptable carrier and a monoclonal antibody or antigen-binding fragment disclosed herein are also provided.

Also provided are nucleic acid molecules encoding a monoclonal antibody or antigen-binding fragment disclosed herein. In some embodiments, the nucleic acid molecule is at least 80%, at least 85%, at least 90%, at least 95%, at least 96%, at least 97%, at least 98% or at least 99% identical to SEQ ID NO: 5, SEQ ID NO: 6, SEQ ID NO: 11, SEQ ID NO: 12, SEQ ID NO: 21, SEQ ID NO: 22, SEQ ID NO: 23 or SEQ ID NO: 24. In some examples, the nucleic acid molecule comprises the nucleotide sequence of SEQ ID NO: 5, SEQ ID NO: 6, SEQ ID NO: 11, SEQ ID NO: 12, SEQ ID NO: 21, SEQ ID NO: 22, SEQ ID NO: 23 and/or SEQ ID NO: 24. In specific non-limiting examples, the nucleic acid molecule comprises SEQ ID NO: 11 and/or SEQ ID NO: 12. In some embodiments, the nucleic acid molecule is operably linked to a promoter. Vectors that include a described nucleic acid molecule are further provided. Cells comprising a nucleic acid molecule or vector disclosed herein are also provided.

Further provided are methods of detecting FXII in a sample. In some embodiments, the method includes contacting the sample with a monoclonal antibody or antigen-binding fragment disclosed herein; and detecting binding of the antibody to the sample. In some examples, the monoclonal antibody or antigen-binding fragment is directly labeled. In other examples, the method further includes contacting the monoclonal antibody or antigen-binding fragment with a second antibody, and detecting the binding of the second antibody to the monoclonal antibody or antigen-binding fragment.

Also provided is an in vitro method of inhibiting activation and/or activity of FXII in a sample that includes FXII. In some embodiments, the method includes contacting the sample with a FXII-specific antibody or antigen-binding fragment disclosed herein. In particular examples, the sample includes a blood or plasma sample. In some examples, the method is a method of inhibiting activity of FXIIa.

Further provided are methods of inhibiting activation and/or activity of FXII in a subject. In some embodiments, the method includes administering to the subject an effective amount of an antibody or antigen-binding fragment disclosed herein. Also provided are methods of treating pathologic processes involving activity and/or activation of FXII in a subject. In some embodiments, the method includes administering to the subject an effective amount of an antibody or antigen-binding fragment disclosed herein. Further provided are methods of inhibiting thrombosis involving activation and/or activity of FXII in a subject. In some embodiments, the method includes administering to the subject an effective amount of an antibody or antigen-binding fragment disclosed herein. In some examples, the method comprises inhibiting activity of FXIIa.

In some embodiments of the methods, the subject suffers from or is at risk of developing a bacterial infection, a fungal infection, a viral infection, a parasitic infection, an ischemic organ disease, microvascular thrombosis, macrovascular thrombosis, thromboembolism, disseminated intravascular coagulation, severe systemic inflammatory response syndrome, allergic or inflammatory reactions involving FXIIa activity, acute respiratory distress syndrome, cancer, amniotic fluid embolism, trauma, transplant rejection, sickle cell disease, autoimmune disease, or has received a medical device implantation. In some examples, the ischemic organ disease is myocardial infarction or ischemic stroke. In some examples, the cancer is a non-metastatic solid tumor cancer, a metastatic solid tumor cancer or a leukemia. In some examples, the medical device implantation is implantation of a catheter, a heart valve, a stent or a graft. In some examples, the methods further include administering to the subject an effective amount of a second anti-coagulant therapy, or an antithrombotic or thrombolytic therapy.

In some embodiments of the disclosed methods, the monoclonal antibody or antigen-binding fragment is administered by parenteral administration. In some embodiments, the monoclonal antibody or antigen-binding fragment is administered at a dose of about 0.1 mg/kg to about 2 g/kg, or about 0.1 mg/kg to about 20 mg/kg, such as about 0.5 mg/kg to about 10 mg/kg, or about 1 mg/kg to about 5 mg/kg. In some examples, the monoclonal antibody or antigen-binding fragment is administered at a dose of about 0.1, about 0.25, about 0.5, about 0.75, about 1.0, about 2.5, about 5.0, about 7.5, about 10, about 12.5, about 15, about 17.5, about 20 mg/kg, about 50 mg/kg, about 75 mg/kg, about 100 mg/kg, about 200 mg/kg, about 500 mg/kg, about 1000 mg/kg or about 2 g/kg.

Kits that include a disclosed monoclonal antibody, antigen-binding fragment, fusion protein, antibody conjugate, composition, nucleic acid molecule, vector or isolated cell are further provided by the present disclosure. The kits can further include, for example, instructional materials, buffers, cell culture media, pharmaceutically acceptable carriers or diluents, and the like.

IV. Antibody Conjugates

Provided herein are antibody conjugates that include a monoclonal antibody or antigen-binding fragment disclosed herein conjugated to an agent, such as a detectable label. For both diagnostic and therapeutic purposes, an agent can be linked or covalently bound to an antibody or antigen-binding fragment disclosed herein. Such a molecule or moiety can be, but is not limited to, an effector or reporter molecule. A reporter molecule is defined as any moiety which can be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. Detectable labels are compounds and/or elements that can be detected due to their specific functional properties and/or chemical characteristics, the use of which allows the antibody to which they are attached to be detected and/or further quantified if desired.

Antibody conjugates can be used as diagnostic agents. Antibody diagnostics generally fall within two classes, those for use in in vitro diagnostics, such as in a variety of immunoassays, and/or those for use in vivo diagnostic protocols, generally known as "antibody-directed imaging."

Many appropriate imaging agents are known in the art, as are methods for their attachment to antibodies (see, for example, U.S. Pat. Nos. 5,021,236; 4,938,948; and 4,472,509, each incorporated herein by reference). The imaging moieties can be, for example, paramagnetic ions; radioactive isotopes; fluorochromes; or NMR-detectable substances.

Exemplary paramagnetic ions include, but are not limited to, chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III). Ions useful in other contexts, such as X-ray imaging, include but are not limited to lanthanum (III), gold (III), lead (II), and bismuth (III).

Exemplary radioactive isotopes for therapeutic and/or diagnostic application include but are not limited to $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$. Radioactively labeled monoclonal antibodies can be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies can be labeled with $^{99m}Tc$ by ligand exchange process, for example, by reducing pertechnate with stannous solution, chelating the reduced technetium onto a SEPHADEX™ column and applying the antibody to this column. Alternatively, direct labeling techniques can be used, for example, by incubating pertechnate, a reducing agent such as $SNCl_2$, a buffer solution such as sodium-potassium phthalate solution, and the antibody. Intermediary functional groups which are often used to bind radioisotopes which exist as metallic ions to an antibody are diethylenetriaminepentaacetic acid (DTPA) or ethylene diaminetetracetic acid (EDTA).

Among the fluorescent labels contemplated for use as conjugates include (but are not limited to) Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Other types of antibody conjugates contemplated are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, horseradish peroxidase or glucose oxidase. Secondary binding ligands include biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Molecules containing azido groups can also be used to form covalent bonds to proteins through reactive nitrene intermediates that are generated by low-intensity ultraviolet light (Potter & Haley, 1983). In particular, 2- and 8-azido analogs of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989 and Dholakia et al., 1989) and can be used as antibody binding agents.

Several methods are known in the art for the attachment or conjugation of an antibody to its conjugate moiety. Some attachment methods involve the use of a metal chelate complex employing, for example, an organic chelating agent such as described in U.S. Pat. Nos. 4,472,509 and 4,938,948 (each incorporated herein by reference). Monoclonal antibodies can also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature. This approach has been reported to produce diagnostically and therapeutically promising antibodies which are currently in clinical evaluation.

In another embodiment, one may choose to modify the immunoglobulins to improve their stability and half-life in vivo. PEGylation is one such process that involves covalent attachment of polyethylene glycol (PEG) polymer chains to the antibody. PEGylation is routinely achieved by incubation of a reactive derivative of PEG with the target molecule. The covalent attachment of PEG can "mask" the antibody from the host's immune system (reduced immunogenicity and antigenicity), and increase the hydrodynamic size (size in solution) of the agent which prolongs its circulatory time by reducing renal clearance. PEGylation can also provide water solubility. Other polymers used to modify antibodies include polyethylene imine and polylysine, often linked through succinic acid groups.

V. Immunodetection Methods

In still further embodiments, provided are immunodetection methods for binding, purifying, removing, quantifying and/or otherwise generally detecting biological components using antibodies that react immunologically with such components. Some immunodetection methods include enzymelinked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods are well-known in the art and can readily be carried out by one of ordinary skill the art.

In general, the immunobinding methods include obtaining a sample containing a target of interest, and contacting the sample with a first antibody that reacts immunologically with the target under conditions effective to allow the formation of immunocomplexes. The binding of the antibody to the target can then be assessed using a variety of different formats.

In one format, the antibody can be linked to a solid support, such as in the form of a column matrix, and the sample suspected of containing the target will be applied to the immobilized antibody. The unwanted components will be washed from the column, leaving the target immunocomplexed to the immobilized antibody to be eluted.

The immunobinding methods also include methods for detecting and quantifying the amount of a target in a sample and the detection and quantification of any immune complexes formed during the binding process. Here, one would obtain a sample suspected of containing a target, and contact the sample with an antibody against the target, and then detect and quantify the number of immune complexes formed under the specific conditions.

In terms of antigen detection, the biological sample analyzed can be any sample that is suspected of containing a target, such as, for example, a body fluid like blood, serum, plasma, mucus, urine, saliva, tears or semen. Alternatively, a tissue can be used. Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with (to bind to targets that react immunologically with) antibodies present. After this time, the sample-antibody composition, such as a tissue section, ELISA plate, dot blot or western blot, will generally be washed to remove any non-specifically bound species, allowing only those molecules specifically bound within the primary immune complexes to be detected.

In general, the detection of immunocomplex formation is well-known in the art and can be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. However, a secondary binding ligand, such as a second antibody and/or a biotin/avidin ligand binding arrangement, can also be used, as is known in the art.

The antibody employed in the detection can itself be linked to a detectable label, wherein one would then simply detect this label, thereby allowing the amount of the primary immune complexes in the composition to be determined Alternatively, the first antibody that becomes bound within the primary immune complexes can be detected by means of a second binding ligand that has binding affinity for the antibody. In these cases, the second binding ligand can be linked to a detectable label. The second binding ligand is itself often an antibody, which can thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system can provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. The enormous amplification capability and specificity of PCR can be utilized to detect a single antigen molecule.

Another ELISA in which the antigens are immobilized involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

ELISAs generally have certain features in common, such as coating, incubating and binding, washing to remove non-specifically bound species, and detecting the bound immune complexes. In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a non-specific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In many ELISAs, a secondary or tertiary detection is used rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions can include diluting the antigens and/or antibodies with solutions such as BSA, bovine gamma globulin (BGG) or phosphate buffered saline (PBS)/Tween. These added agents also tend to assist in the reduction of nonspecific background.

A "suitable" condition also means that the incubation is at a temperature or for a period of time sufficient to allow effective binding. In some examples, the incubation steps are from about 1 to about 4 hours, and at temperatures of about 25° C. to about 27° C., or overnight at about 4° C.

VI. Antibody Purification

In certain embodiments, the antibodies against FXII can be purified. The term "purified," as used herein, is intended to refer to a composition, isolatable from other components, wherein the protein is purified to any degree relative to its naturally-obtainable state. A purified protein therefore also refers to a protein, free from the environment in which it can naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest can be further purified using chromatographic and electrophoretic techniques to achieve partial or complete purification (or purification to homogeneity).

Analytical methods particularly suited to the preparation of a pure peptide are ion-exchange chromatography, exclusion chromatography; polyacrylamide gel electrophoresis; isoelectric focusing. Other methods for protein purification include precipitation with ammonium sulfate, PEG, antibodies and the like or by heat denaturation, followed by centrifugation, gel filtration, reverse phase, hydroxylapatite and affinity chromatography; and combinations of such and other techniques.

In purifying an antibody against FXII, it can be desirable to express the polypeptide in a prokaryotic or eukaryotic expression system and extract the protein using denaturing conditions. The polypeptide can be purified from other cellular components using an affinity column, which binds to a tagged portion of the polypeptide. As is generally known in the art, it is believed that the order of conducting the various purification steps can be changed, or that certain steps can be omitted, and still result in a suitable method for the preparation of a substantially purified protein or peptide.

Commonly, complete antibodies are fractionated utilizing agents (such as protein A) that bind the Fc portion of the antibody. Alternatively, antigens can be used to simultaneously purify and select appropriate antibodies. Such methods often utilize the selection agent bound to a support, such as a column, filter or bead. The antibodies are bound to a support, contaminants removed, and the antibodies released by applying particular conditions (such as salt, heat, etc.).

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity. It is known that the migration of a polypeptide can vary, sometimes significantly, with different conditions of SDS/PAGE. It will therefore be appreciated that under differing electrophoresis conditions, the apparent molecular weights of purified or partially purified expression products can vary.

VII. Pharmaceutical Compositions

Pharmaceutical compositions can comprise an effective amount of one or more antibodies, therapeutic agents or additional agent dissolved or dispersed in a pharmaceutically acceptable carrier. Aqueous compositions comprise an effective amount of the antibody, dissolved or dispersed in a pharmaceutically acceptable carrier or aqueous medium. The terms "pharmaceutically acceptable", "therapeutically acceptable", and the like, refer to molecular entities and compositions that do not produce an adverse, allergic or other untoward reaction when administered to an animal, or a human, as appropriate.

The terms "pharmaceutically acceptable carrier" and "therapeutically acceptable carrier" include any and all solvents, dispersion media, coatings, surfactants, antioxidants, preservatives (for example, antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed, Mack Printing Company, 1990, pp. 1289-1329, incorporated herein by reference). The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, and general safety and purity standards.

The biological material should be extensively dialyzed to remove undesired small molecular weight molecules and/or lyophilized for more ready formulation into a desired vehicle, where appropriate. The active compounds will then generally be formulated for parenteral administration, for example, formulated for injection or other means via the intravenous, intramuscular, subcutaneous, intranasal, intrapulmonary, intrathecal, or intraperitoneal routes. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability or aerosol delivery exists. It can be incorporated into other drug delivery vehicles designed for extended release, or modified to have an extended biological half-life. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropyl cellulose. Dispersions can also be prepared in glycerol, liquid polyethylene glycols, and mixtures thereof and in oils. Under ordinary conditions of storage and use, these preparations contain a preservative to prevent the growth of microorganisms.

The antibodies against FXII can be formulated into a composition in a free base, in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as a lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, isotonic agents can be included, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as a solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intranasal, and intraperitoneal administration. In this connection, sterile aqueous media which can be employed will be known to those of skill in the art in light of the present disclosure. For example, one dosage can be dissolved in 1 ml of isotonic NaCl solution and either added to 1000 ml of hypodermoclysis fluid or injected at the proposed site of infusion, (see, for example, Remington's Pharmaceutical Sciences, $15^{th}$ Ed. Mack Printing Company, pages 1035-1038 and 1570-1580, 1975). Some variation in dosage will necessarily occur depending on the condition of the subject being treated. The person responsible for administration will determine the appropriate dose for the individual subject.

In addition to the compounds formulated for parenteral administration, such as intravenous or intramuscular injection, other pharmaceutically acceptable forms include, for example, tablets or other solids for oral administration; liposomal formulations, time release capsules; and any other form currently used, including creams.

The therapeutic agent can comprise different types of carriers depending on whether it is to be administered in solid, liquid or aerosol form, and whether it needs to be sterile for such routes of administration as injection. The antibodies against FXII can be administered intravenously, intradermally, intraarterially, intraperitoneally, intralesionally, intracranially, intraarticularly, intraprostatically, intrapleurally, intratracheally, intranasally, intravitreally, intravaginally, intrarectally, topically, intramuscularly, subcutaneously, subconjunctival, intravesicularlly, mucosally, intrapericardially, intraumbilically, intraocularally, orally, locally, by inhalation (such as aerosol inhalation), by injection, by infusion, by continuous infusion, localized perfusion, bathing target cells directly, via a catheter, via a lavage, in creams, in lipid compositions (such as liposomes), or by other methods or any combination of the foregoing as would be known to one of ordinary skill in the art (see, for example, Remington's Pharmaceutical Sciences, 18th Ed. Mack Printing Company, 1990, incorporated herein by reference).

The actual dosage amount of a composition administered to an animal or human patient can be determined by physical and physiological factors such as body weight, the severity of the condition, the type of disease being treated, previous or concurrent therapeutic interventions, idiopathy of the patient and the route of administration. The practitioner responsible for administration will determine the concentration of active ingredient(s) in a composition and appropriate dose(s) for the individual subject.

In certain embodiments, pharmaceutical compositions can comprise, for example, at least about 0.1% of an active compound. In other embodiments, an active compound can comprise between about 2% to about 75% of the weight of the unit, or between about 25% to about 60%, for example, and any range derivable therein.

In some embodiments, the composition comprises various antioxidants to retard oxidation of one or more component. In embodiments where the composition is in a liquid form, a carrier can be a solvent or dispersion medium comprising but not limited to, water, ethanol, polyol (for example, glycerol, propylene glycol, liquid polyethylene glycol, etc.), lipids (for example, triglycerides, vegetable oils, liposomes) and combinations thereof. The proper fluidity can be maintained, for example, by the use of a coating, such as lecithin; by the maintenance of the required particle size by dispersion in carriers such as, for example, liquid polyol or lipids; by the use of surfactants such as, for example, hydroxypropyl cellulose; or combinations thereof. In many cases, isotonic agents can be included, such as, for example, sugars, sodium chloride or combinations thereof.

In particular embodiments, prolonged absorption of an injectable composition can be brought about by the use in the compositions of agents delaying absorption, such as, for example, aluminum monostearate, gelatin or combinations thereof.

The antibodies of the present disclosure, which inhibit FXII activity, are inherently safe given that factor XII deficiency is asymptomatic in humans and animals, such as mice. This is a major advance relative to using other anticoagulant antibodies because antibodies other than those discussed here (other than those inhibiting contact activation of FXII) are expected to cause bleeding disorders regardless of their route of administration or dosage. Antibodies like those disclosed here will not have such adverse effects on hemostasis given that factor XII does not participate in vital hemostasis. Indeed, the danger from overdose is theoretically zero because it has no additional effect beyond the saturation of its target. Thus, the antibodies of the present application are safe antithrombotics (anticoagulants, blood-thinners).

The pharmaceutical compositions can be parenterally administered to subjects suffering from diseases in which FXII activation is problematic. The compositions can be administered to patients in need as a bolus or by continuous infusion. For example, a bolus administration of an antibody or antibody fragment can be in an amount of from 0.0025 to 100 mg/kg body weight, 0.025 to 0.25 mg/kg, 0.010 to 0.10 mg/kg or 0.10 to 0.50 mg/kg. For continuous infusion, an inventive antibody present as a Fab fragment can be administered at 0.001 to 100 mg/kg body weight/minute, 0.0125 to 1.25 mg/kg/min., 0.010 to 0.75 mg/kg/min., 0.010 to 1.0 mg/kg/min. or 0.10 to 0.50 mg/kg/min for a period of 1-24 hours, 1-12 hours, 2-12 hours, 6-12 hours, 2-8 hours, or 1-2 hours. Antibodies can be administered by bolus injections, repeated hourly, daily, weekly, or monthly as a function of dose. The frequency and duration of the administration would depend upon the severity of the condition and the need for continued therapeutic activity, without limitation. Frequency could also range from three times per week to once every two weeks to six months.

Additionally, the compositions can be administered to patients via subcutaneous, intravenous, or intramuscular injection. For example, a dose of 10 to 100 mg anti-FXII antibody can be administered to patients via subcutaneous injection daily, weekly, biweekly or monthly.

The antibodies of the present disclosure can be used as monotherapy but may be combined with other therapies. For example, co-administration of one or more additional anti-thrombotic or anti-inflammatory agents, such as nonsteroidal anti-inflammatory drugs (NSAIDs), platelet inhibitors, anticoagulants, or thrombolytic agents believed to be useful for treating certain diseases. These combination therapies are likely to reduce the necessary frequency or dose of anti-clotting or anti-inflammatory drugs. By co-administration or combination therapy is meant administration of the two therapeutic drugs each formulated separately or formulated together in one composition, and, when formulated separately, administered either at approximately the same time or at different times, but over the same therapeutic period.

Antiplatelet drugs for use in combinations include irreversible cyclooxygenase inhibitors (aspirin), adenosine diphosphate (ADP) receptor inhibitors (clopidogrel, prasugrel, ticagrelor, and ticlopidine), phosphodiesterase inhibitors (cilostazol), glycoprotein IIB/IIIA inhibitors (abciximab, eptifibatide, and tirofiban), adenosine reuptake inhibitors (dipyridamole), and thromboxane inhibitors, such as thromboxane synthase inhibitors (ifetroban), thromboxane receptor antagonists (seratrodast, picotamide), and terutroban.

Anticoagulant drugs for use in combinations include vitamin K antagonists (warfarin), unfractionated and low molecular weight heparins (enoxaparin, dalteparin, heparin), thrombin inhibitors (bivalirudin, argatroban, dabigatran, antithrombin III), and factor Xa inhibitors (apixaban, fondaparinux, rivaroxaban, edoxaban).

Fibrinolytic agents for use in combinations include anistreplase, reteplase, streptokinase, kabikinase, alteplase, tenecteplase, urokinase, staphylokinase, plasmin, and rokinase.

Anti-inflammatory drugs for use in combinations include NSAIDs such as celecoxib, piroxicam, indomethacin, meloxicam, ketoprofen, sulindac, aspirin, diflunisal, nabumetone, and corticosteroids such as prednisone, betamethasone, cortisone, dexamethasone, hydrocortisone, methylprednisolone, and prednisolone. These may also include inhibitors of the complement system or the kallikrein kinin system.

VIII. Kits

Any of the compositions described herein can be comprised in a kit. The kits will thus comprise, in a suitable container, an antibody (or antigen-binding fragment) and/or an additional agent. Other components can be included in a kit. Diagnostic and therapeutic kits comprise in suitable containers, a pharmaceutically acceptable formulation of an antibody in a pharmaceutically acceptable formulation. The kit can have a single container, and/or it can have distinct containers for each compound.

When the components of the kit are provided in one and/or more liquid solutions, the liquid solution can be an aqueous solution, with a sterile aqueous solution being one example of a particular embodiment. The antibody can also be formulated into a syringeable composition, in which case, the container can itself be a syringe, pipette, and/or other such like apparatus, from which the formulation can be applied to an infected area of the body, injected into an animal, and/or even applied to aid/or mixed with the other components of the kit.

However, the components of the kit can be provided as dried powder(s). When reagents and/or components are provided as a dry powder, the powder can be reconstituted by the addition of a suitable solvent. It is envisioned that the solvent can also be provided in another container.

The container will generally include at least one vial, test tube, flask, bottle, syringe and/or other containers, into which the antibody/antibody formulation is placed, suitably allocated. The kits can also comprise a second container for containing a sterile, pharmaceutically acceptable buffer and/or another diluent.

The kits can also include a means for containing the vials in close confinement for commercial sale, such as, for example, injection and/or blow-molded plastic containers into which the desired vials are retained.

Irrespective of the number and/or type of containers, the kits can also comprise, and/or be packaged with, an instrument for assisting with the injection/administration and/or placement of the ultimate antibody within the body of an animal. Such an instrument can be a syringe, pipette, forceps, and/or any such medically approved delivery vehicle.

IX. Therapeutic Uses

The antibodies of the present disclosure, which prevent FXII activity, are inherently safe given that FXII deficiency is asymptomatic in humans and mice. This is a major advance relative to using other anticoagulant antibodies because antibodies other than those disclosed herein are expected to cause bleeding disorders regardless of their route of administration or dosage. Antibodies like those disclosed herein do not have such adverse effects on hemostasis given that FXII does not participate in vital hemostasis. Indeed, the danger from overdose is theoretically zero because it has no additional effect beyond the saturation of its target. Thus, the antibodies of the present disclosure are safe antithrombotics (anticoagulant, blood thinner) and safe anti-inflammatory molecules.

A. Thrombosis and Thromboembolism

Thrombosis is the formation of a blood clot inside a blood vessel, obstructing the flow of blood through the circulatory system. When a blood vessel is injured, the body uses platelets (thrombocytes) and fibrin to form a blood clot to prevent blood loss. Even when a blood vessel is not injured, blood clots may form in the body under certain conditions.

A clot that breaks free and begins to travel around the body is known as an embolus. When a thrombus occupies more than 75% of the cross-sectional area of the lumen of an artery, blood flow to the tissue supplied is reduced enough to cause symptoms because of decreased oxygen (hypoxia) and accumulation of metabolic products like lactic acid. More than 90% obstruction can result in anoxia, the complete deprivation of oxygen, and infarction, a mode of cell death. Thromboembolism is the combination of thrombosis and its main complication, embolism.

There are two distinct forms of thrombosis, venous thrombosis and arterial thrombosis, each of which can be presented by several subtypes. Venous thrombosis is the formation of a thrombus (blood clot) within a vein. There are several diseases which can be classified under this category.

Deep vein thrombosis (DVT) is the formation of a blood clot within a deep vein. It most commonly affects leg veins, such as the femoral vein. Three factors are important in the formation of a blood clot within a deep vein: the rate of blood flow, the thickness of the blood and the quality of the vessel wall. Classical signs of DVT include swelling, pain and redness of the affected area.

A portal vein thrombosis is a form of venous thrombosis affecting the hepatic portal vein, which can lead to portal hypertension and reduction of the blood supply to the liver. It usually has a pathological cause such as pancreatitis, cirrhosis, diverticulitis or cholangiocarcinoma.

Renal vein thrombosis is the obstruction of the renal vein by a thrombus. This tends to lead to reduced drainage from the kidney. Anticoagulation therapy is the treatment of choice.

Jugular vein thrombosis is a condition that may occur due to infection, intravenous drug use or malignancy. Jugular vein thrombosis can have a varying list of complications, including: systemic sepsis, pulmonary embolism, and papilledema. Though characterized by a sharp pain at the site of the vein, it can prove difficult to diagnose, because it can occur at random.

Budd-Chiari syndrome is the blockage of the hepatic vein or the inferior vena cava. This form of thrombosis presents with abdominal pain, ascites and hepatomegaly. Treatment varies between therapy and surgical intervention by the use of shunts.

Paget-Schroetter disease is the obstruction of an upper extremity vein (such as the axillary vein or subclavian vein) by a thrombus. The condition usually comes to light after vigorous exercise and usually presents in younger, otherwise healthy people. Men are affected more than women.

Cerebral venous sinus thrombosis (CVST) is a rare form of stroke which results from the blockage of the dural venous sinuses by a thrombus. Symptoms may include headache, abnormal vision, any of the symptoms of stroke such as weakness of the face and limbs on one side of the body and seizures. The diagnosis is usually made with a CT or MRI scan. The majority of persons affected make a full recovery. The mortality rate is 4.3%.

Arterial thrombosis is the formation of a thrombus within an artery. In most cases, arterial thrombosis follows rupture of atheroma, and is therefore referred to as atherothrombosis. Another common cause of arterial thrombosis is atrial fibrillation, which causes disturbed blood flow. In addition, it is well known that the direct current cardioversion of atrial fibrillation carries a great risk of thromboembolism, especially if persisting more than 48 hours. Thromboembolism strikes approximately 5% of cases not receiving anticoagulant therapy. The mechanism and pathogenesis of thromboembolism after cardioversion is not completely understood.

Arterial thrombosis can embolize and is a major cause of arterial embolism, potentially causing infarction of almost any organ in the body.

Hepatic artery thrombosis usually occurs as a devastating complication after liver transplantation. An arterial embolus can also form in the limbs.

Thus, actual bleeding in patients with thrombosis, for example, those that are bleeding due to another drug, or any other cause, inherited or acquired, can be safely treated. Also, foreign body-associated thrombosis, for example, that associated with extracorporeal devices, oxygenators, dialysis membranes, catheters, intravascular objects (such as stents, grafts) may be safely treated, particularly when other drugs are contraindicated.

B. Disseminated Intravascular Coagulation or Consumptive Coagulopathy

Consumptive coagulopathy (CC), also known as disseminated intravascular coagulation (DIC) or disseminated intravascular coagulopathy, is a pathological activation of coagulation (blood clotting) mechanisms that happen in response to a variety of diseases. DIC leads to the formation of small blood clots inside the blood vessels throughout the body. As the small clots consume coagulation proteins and platelets, normal coagulation is disrupted and abnormal bleeding occurs from the skin (for example, from sites where blood samples were taken), the gastrointestinal tract, the respiratory tract and surgical wounds. The small clots also disrupt normal blood flow to organs (such as the kidneys), which may malfunction as a result.

DIC can occur acutely but also on a slower, chronic basis, depending on the underlying problem. It is common in the critically ill, and may participate in the development of multiple organ failure, which may lead to death.

Under homeostatic conditions, the body is maintained in a finely tuned balance of coagulation and fibrinolysis. The activation of the coagulation cascade yields thrombin that converts fibrinogen to fibrin; the stable fibrin clot being the final product of hemostasis. The fibrinolytic system then functions to break down fibrinogen and fibrin. Activation of the fibrinolytic system generates plasmin (in the presence of thrombin), which is responsible for the lysis of fibrin clots. The breakdown of fibrinogen and fibrin results in polypeptides called fibrin degradation products (FDPs) or fibrin split products (FSPs). In a state of homeostasis, the presence of plasmin is critical, as it is the central proteolytic enzyme of coagulation and is also necessary for the breakdown of clots, or fibrinolysis.

In DIC, the processes of coagulation and fibrinolysis are dysregulated, and the result is widespread clotting with resultant bleeding. Regardless of the triggering event of DIC, once initiated, the pathophysiology of DIC is similar in all conditions. One critical mediator of DIC is the release of a transmembrane glycoprotein called tissue factor (TF). TF is present on the surface of many cell types (including endothelial cells, macrophages, and monocytes) and is not normally in contact with the general circulation, but is exposed to the circulation after vascular damage. For example, TF is released in response to exposure to cytokines (particularly interleukin 1), tumor necrosis factor, and endotoxin. This plays a major role in the development of DIC in septic conditions. TF is also abundant in tissues of the lungs, brain, and placenta. This helps to explain why DIC readily develops in patients with extensive trauma. Upon activation, TF binds with coagulation factors which then triggers the extrinsic pathway (via FVII) which subsequently triggers the intrinsic pathway (XII to XI to IX) of coagulation.

The release of endotoxin is the mechanism by which Gram-negative sepsis provokes DIC. In acute promyelocytic leukemia, treatment causes the destruction of leukemic granulocyte precursors, resulting in the release of large amounts of proteolytic enzymes from their storage granules, causing microvascular damage. Other malignancies may enhance the expression of various oncogenes that result in the release of TF and plasminogen activator inhibitor-1 (PAI-1), which prevents fibrinolysis.

Excess thrombin in the circulation results from the excess activation of the coagulation cascade. The excess thrombin cleaves fibrinogen, which ultimately leaves behind multiple fibrin clots in the circulation. These excess clots trap platelets to become larger clots, which leads to microvascular and macrovascular thrombosis. This lodging of clots in the microcirculation, in the large vessels, and in the organs is what leads to the ischemia, inflammation, impaired organ perfusion, and end-organ damage that occurs with DIC.

Coagulation inhibitors are also consumed in this process. Decreased inhibitor levels will permit more clotting so that a feedback system develops in which increased clotting leads to more clotting. At the same time, thrombocytopenia occurs and this has been attributed to the entrapment and consumption of platelets. Clotting factors are consumed in the development of multiple clots, which contributes to the bleeding seen with DIC.

Simultaneously, excess circulating thrombin assists in the conversion of plasminogen to plasmin, resulting in fibrinolysis. The breakdown of clots results in excess amounts of FDPs, which have powerful anticoagulant properties, contributing to hemorrhage. The excess plasmin also activates the complement and kinin systems. Activation of these systems leads to many of the clinical symptoms that patients experiencing DIC exhibit, such as shock, hypotension, and increased vascular permeability. The acute form of DIC is considered an extreme expression of the intravascular coagulation process with a complete breakdown of the normal homeostatic boundaries. DIC is associated with a poor prognosis and a high mortality rate.

There has been a recent challenge however to the basic assumptions and interpretations of the pathophysiology of DIC. A study of sepsis and DIC in animal models has shown that a highly-expressed receptor on the surface of hepatocytes, termed the Ashwell-Morell receptor, is responsible for thrombocytopenia in bacteremia and sepsis due to streptococcal pneumonia (SPN) and possibly other pathogens. The thrombocytopenia observed in SPN sepsis was not due to increased consumption of coagulation factors such as platelets, but instead was the result of this receptor's activity enabling hepatocytes to ingest and rapidly clear platelets from circulation. By removing prothrombotic components before they participate in the coagulopathy of DIC, the Ashwell-Morell receptor lessens the severity of DIC, reducing thrombosis and tissue necrosis, and promoting survival. The hemorrhage observed in DIC and among some tissues lacking this receptor may thereby be secondary to increased thrombosis with loss of the mechanical vascular barrier. This discovery has possible significant clinical implications in devising new approaches to reducing the pathophysiology of DIC.

The only effective treatment is the reversal of the underlying cause. Anticoagulants are given exceedingly rarely, and only when thrombus formation is likely to lead to imminent death (such as in coronary artery thrombosis or cerebrovascular thrombosis). Platelets may be transfused if counts are less than 5,000-10,000/mm$^3$ and massive hemorrhage is occurring, and fresh frozen plasma may be administered in an attempt to replenish coagulation factors and anti-thrombotic factors, although these are only temporizing measures and may result in the increased development of thrombosis.

DIC results in lower fibrinogen levels (as it has all been converted to fibrin), and this can be tested for in the hospital laboratory. This test is for "fibrin split products" (FSPs) or "fibrin degradation products" (FDPs) which are produced when fibrin undergoes degradation when blood clots are dissolved by fibrinolysis. In some situations, infusion with antithrombin may be necessary.

C. Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present disclosure provides for the safe treatment of bleeding in trauma patients, including both pre-treatment (in the case of a medical procedure) and treatment after traumatic injury has occurred.

Surgeons use operative manual and instrumental techniques on a patient to investigate and/or treat a pathological condition such as disease or injury, to help improve bodily function or appearance, or sometimes for some other reason. The present disclosure can safely address trauma resulting from surgeries, including pen-surgical and peri-interventional thromboprophylaxis, especially when the risk of bleeding is high. Two particular areas of concern are surgeries relating to the nervous system and the eye.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as the use of a sterile environment, anesthesia, antiseptic conditions, typical surgical instruments, and suturing or stapling. All forms of surgery are considered invasive procedures; so-called noninvasive surgery usually refers to an excision that does not penetrate the structure being addressed (for example, laser ablation of the cornea) or to a radiosurgical procedure (such as irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classed by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty. By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

Traumatic hemorrhage accounts for much of the wide ranging international impact of injury, causing a large proportion of deaths and creating great morbidity in the injured. Despite differences in pre-hospital care, the acute management of traumatic hemorrhage is similar around the world and follows well accepted published guidelines. A critically injured patient's care occurs as four, often overlapping segments: the resuscitative, operative, and critical care phases. The diagnosis and control of bleeding should be a high priority during all of the phases of trauma care and is especially important in the patient who is in hemorrhagic shock. Early attempts at hemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of hemorrhage, and appropriate transfusion of blood and blood products are provided. In the operative phase, surgical control of the hemorrhage and any other injury, and additional transfusion is provided. Finally, the critical care phase provides for post-operative support and tissue perfusion.

D. Device Implantation

An implant is a medical device manufactured to replace a missing biological structure, support a damaged biological structure, or enhance an existing biological structure. Medical implants are man-made devices, in contrast to a transplant, which is a transplanted biomedical tissue. The surface of implants that contact the body might be made of a biomedical material such as titanium, silicone or apatite depending on what is the most functional. In some cases, implants contain electronics, for example, artificial pacemaker and cochlear implants. Some implants are bioactive, such as subcutaneous drug delivery devices in the form of implantable pills or drug-eluting stents.

Among the most common types of medical implants are the pins, rods, screws and plates used to anchor fractured bones while they heal. More complex implants include artificial joints, such as knee and hip joints, breast implants, artificial heart valves, stents and catheters.

E. Transplant

Organ transplantation an organ from one body to another or from a donor site on the patient's own body, for the purpose of replacing the recipient's damaged or absent organ. The emerging field of regenerative medicine is allowing scientists and engineers to create organs to be re-grown from the patient's own cells (stem cells, or cells extracted from the failing organs). Organs and/or tissues that are transplanted within the same person's body are called autografts. Transplants that are recently performed between two subjects of the same species are called allografts. Allografts can either be from a living or cadaveric source.

Organs that typically can be transplanted are the heart, kidneys, liver, lungs, pancreas, intestine, and thymus. Tissues include bones, tendons (both referred to as musculoskeletal grafts), cornea, skin, heart valves, and veins. Worldwide, the kidneys are the most commonly transplanted organs, followed closely by the liver and then the heart. The cornea and musculoskeletal grafts are the most commonly transplanted tissues; these outnumber organ transplants by more than ten-fold.

Organ donors may be living, or brain dead. Tissue may be recovered from donors who are cardiac dead—up to 24 hours past the cessation of heartbeat. Unlike organs, most tissues (with the exception of corneas) can be preserved and stored for up to five years, meaning they can be "banked." In the United States of America, tissue transplants are regulated by the U.S. Food and Drug Administration (FDA) which sets strict regulations on the safety of the transplants, primarily aimed at the prevention of the spread of communicable disease. Regulations include criteria for donor screening and testing as well as strict regulations on the processing and distribution of tissue grafts. Organ transplants are not regulated by the FDA.

Transplantation medicine is one of the most challenging and complex areas of modern medicine. In addition to the key problem of transplant rejection, thrombosis resulting from clotting at the site of surgery followed by transport of the clot into the vasculature is a major concern.

F. Cancer

A diversity of coagulation disorders in cancer patients arise from tumor-specific growth characteristics, neoangiogenesis with impaired endothelial lining, defective myelopoiesis, hypoproteinemia or metastatic lesions growth with organ dysfunction. Recent investigations have found a clinically relevant correlation between coagulation disorders and tumor growth. These prompted new therapeutic strategies focused on growth factors with the aim to control tumor metastasis, particularly if used for the treatment of micrometastatic disease. However, such treatment may lead to the life-threatening coagulation imbalance.

Indeed, some cancers express more thrombogenic proteins than normal cells. These proteins include tissue factor, collagen, laminin, factors VII, XI, and XII, plasminogen activator inhibitor, antithrombin, vitronectin, fibronectin, and fibrinogen. These proteins may appear on the cancer cell surface or may be secreted, and can trigger cancer-associated thrombosis, which is quite frequent among cancer patients. Safe anticoagulation with antibodies of the present disclosure may assist some cancer patients with compromised hemostasis.

A coagulation homeostasis may become further impaired after nonsurgical cancer therapy, especially after preoperative irradiation, which produces lesions precipitating both bleeding and thrombosis. Anticancer chemotherapy may affect liver function and decrease the synthesis of both procoagulation and anticoagulation factors. Most chemotherapeutic protocols affect platelet synthesis, which arises as a principal dose-limiting side effect. This was observed both during combined systemic chemotherapy and local antitumor therapy. Although the side effects produced by chemotherapy are reversible, endothelial lesions may persist for many years after the anticancer treatment. Furthermore, some patients have low platelet count during chemotherapy, and these patients are at risk of bleeding, but still may need to be treated for thrombosis.

G. Stroke and Myocardial Infarction

A stroke is the rapid decline of brain function due to a disturbance in the supply of blood to the brain. This can be due to ischemia, thrombus, embolus (a lodged particle) or hemorrhage (a bleed). In thrombotic stroke, a thrombus (blood clot) usually forms around atherosclerotic plaques. Since blockage of the artery is gradual, the onset of symptomatic thrombotic strokes is slower. Thrombotic stroke can be divided into two categories: large vessel disease and small vessel disease. The former affects vessels such as the internal carotids, vertebral and the circle of Willis. The latter can affect smaller vessels such as the branches of the circle of Willis.

Myocardial infarction (MI) is caused by an infarct (death of tissue due to ischemia), often due to the obstruction of a coronary artery by a thrombus. MI can quickly become fatal if emergency medical treatment is not received promptly. If diagnosed within 12 hours of the initial episode (attack) then thrombolytic therapy is initiated.

H. Infection

If an infection is present at the site of thrombosis, the thrombus may break down, spreading particles of infected material throughout the circulatory system (pyemia, septic embolus) and setting up metastatic abscesses wherever they come to rest. Without an infection, the thrombus may become detached and enter circulation as an embolus, finally lodging in and completely obstructing a blood vessel, which unless treated very quickly will lead to tissue necrosis (an infarction) in the area past the occlusion. If the occlusion is in the coronary artery, myocardial ischemia is likely to occur, whereby cardiac myocytes cannot function properly due to lack of oxygen. This lack of oxygen is then likely to result in a myocardial infarction.

I. Inflammation

Inhibition of FXIIa is expected to attenuate all pathological reactions that are supported by contact activation. For example, contact activation can promote anaphylaxis, angioedema, pulmonary reactions (such as asthma), skin reactions, intestinal reactions, eye reactions, cardiovascular reactions (shock, edema, etc.), and systemic inflammatory response syndrome. FXIIa produces kallikrein by cleaving plasma prekallikrein, which in turn cleaves kininogen 1 and liberates bradykinin. Bradykinin is one of the most potent known inflammatory mediators. Thus, inhibiting FXIIa attenuates prekallikrein and thereby reduces bradykinin generation and is expected to interfere with the inflammatory and vasoregulatory reactions that involve the bradykinin pathways. Since contact activation also can trigger activation of the complement system, FXII inhibition is reasonably expected to reduce inflammatory reactions that involve the complement system.

J. Combination Therapy

The antibodies of the present disclosure can be used as monotherapy, but also may be combined with other therapies that are used for the treatment of the disease condition that FXII inhibitors would be expected to treat. For example, co-administration of one or more additional anti-inflammatory or antithrombotic agents, such as NSAIDs, platelet inhibitors, anticoagulants, or thrombolytic agents is believed useful for treating certain diseases. These combination therapies are likely to reduce the necessary treatment frequency or dose of the other drugs that target the same pathological condition. By co-administration or combination therapy is meant administration of therapeutic drugs each formulated separately or formulated together in one composition, and, when formulated separately, administered either at approximately the same time or at different times, but over the same therapeutic period.

The following examples are provided to illustrate certain particular features and/or embodiments. These examples should not be construed to limit the disclosure to the particular features or embodiments described.

EXAMPLES

Example 1

Materials and Methods

This example describes the experimental procedures and materials used for the studies described in Example 2.

Generation of Anti-FXII Monoclonal Antibodies (MAb)

FXII-deficient mice were immunized with recombinant human FXII (Ivanov et al., *Blood* 2017; 129:1527-1537) and hybridomas were produced by standard methods. The clone 5C12 produces an antibody that binds to FXII and FXIIa. The hybridoma cells were subcloned and expanded, 5C12 was purified using standard procedures, characterized in vitro and then used in experiments, in vivo.

Characterization of 5C12

FXII (40 nM) (Haematologic Technologies, Inc., Essex Junction, VT) was incubated with 0-80 nM 5C12 (10 minutes) and then with 1 µg/ml dextran sulfate (20 minutes). Spectrozyme FXIIa (0.5 mM) (Sekisui Diagnostics GmbH, Pfungstadt, Germany) was then added to measure hydrolysis by activated FXII (FXIIa). Next, FXII (100 nM) and 5C12 (0-200 nM) were co-incubated (10 minutes) and then diluted 50/50 with kininogen-1 (HK,12.5 nM), prekallikrein (PK, 12.5 nM) (Enzyme Research Laboratories, South Bend, IN), and short or long chain polyphosphate (10 µM) (60 minutes, final concentrations) (Ivanov et al., *Blood* 2017; 129:1527-1537). Amidolytic activity was quantified after addition of polybrene (6 µg/ml) and soybean trypsin inhibitor (50 µg/ml). To test FXIIa inhibition, Spectrozyme FXIIa was added to mixtures of FXIIa (20 nM) and 5C12 (0-40 nM). To test the effect of 5C12 (0-100 nM) on FXII (100 nM) activation, corn trypsin inhibitor (CTI, 40 µg/ml), kallikrein (5 nM) and dextran sulfate (10 µg/ml) were co-incubated (0-60 minutes). Samples were separated by reducing SDS-PAGE and immunoblotted with an anti-FXII polyclonal antibody (Santa Cruz Biotechnology, Inc., Dallas, TX).

Baboon Model of Thrombogenesis in Extracorporeal Membrane Oxygenators

Chronic exteriorized femoral arterio-venous (AV) shunt-bearing baboons (n=3) were used, as described previously (Gruber and Hanson, *Blood* 2003; 102:953-955; Crosby et al., *Arter Thromb Vasc Biol* 2013; 33:1670-1678; Gruber et al., *Thromb Res* 2007; 119:121-127). In brief, baboons received $^{111}$In-labeled autologous platelets and $^{125}$I-labeled homologous fibrinogen and then their AV shunts were extended to incorporate a saline-primed membrane oxygenator cartridge (Terumo-CAPIOX® RX05, Terumo Cardiovascular Group, Ann Arbor, MI) perfused by AV pressure gradient-driven blood at a restricted 0.1 L/min flow rate. Platelet radioactivity within the oxygenator was recorded using gamma camera imaging (GE-Brivo NM 615 interfaced with Xeleris 3.1 software, GE Healthcare, Chicago, IL) and calculated as described for other devices in the chronic AV shunt model (Gruber and Hanson, *Blood* 2003; 102:953-955; Gruber et al., *Thromb Res* 2007; 119:121-127; Hanson et al., *J Clin Invest* 1993; 92:2003-2012; Tucker et al., *Blood* 2009; 113:936-944). At 60 minutes, the cartridge was removed, rinsed, dried, and stored refrigerated for subsequent evaluation of $^{125}$I-fibrin content, as previously described (Gruber and Hanson, *Blood* 2003; 102:953-955; Hanson et al., *J Clin Invest* 1993; 92:2003-2012). In brief, the oxygenators were filled with digest buffer (10 mM Tris-H$_3$PO$_4$ pH 7.0, 35 mM SDS) for 3 days to solubilize the trapped clots, and radioactivity was measured using a gamma counter (Wizard-3, PerkinElmer, Shelton, CT).

Anticoagulation of Baboons

In a dose-finding experiment, six consecutive 5C12 doses of 1 mg/kg were injected IV at 40-min intervals, and aPTT prolongation of plasma samples was measured. It was found that 5 mg/kg of 5C12 produced near saturating effects on coagulation. It was also determined that a low dose of heparin (20 U/kg) 15 minutes before perfusion kept oxygenators patent with some measurable real-time platelet deposition, which allowed for the determination of any change upon supplemental anticoagulation with 5C12. In two oxygenator perfusion experiments, the oxygenator was perfused without heparinization. In definitive experiments, pretreatment with heparin (20 U/kg), 5C12 (5 mg/kg), or their combination were evaluated for their effect on platelet retention in the oxygenator cartridge.

Hemostasis Assessment

Primary skin hemostasis was evaluated using the adult Surgicutt® device (Instrumentation Laboratories, Bedford, MA). Bleeding time (BT) was recorded twice during each experiment. Blood loss during the BT test was measured. The skin wounds were observed for re-bleeding. Since prolongation of the prothrombin time (PT) is the most utilized and clinically important marker of hemostasis impairment, plasma prothrombin time was measured using a KC4 coagulometer.

Blood Analyses

Blood samples were collected into citrate, and plasma aPTT was measured using SynthASil (Instrumentation Laboratory, Bedford, MA) and a KC4™Analyzer (TCoag, Ltd, Ireland). Activated clotting time (ACT) of blood was determined using LupoTek KCT (r$^2$-Diagnostics, South Bend, IN). Plasma thrombin-antithrombin complex (TAT) and platelet factor 4 (PF4) were measured with ELISA kits from Siemens (Marburg, Germany) and RnD Systems (Minneapolis, MN), respectively.

Data Analyses

Numeric values are shown as mean and range in the text, in the figures mean and SEM are shown. Means were compared by one-way ANOVA for treatment using GraphPad Prism 5 (GraphPad Software, San Diego, CA). Comparisons between heparin and heparin+5C12 results on platelet deposition rates over time were performed by repeated measures ANOVA for time and treatment using SigmaPlot 11 (Systat, Inc., Chicago, IL). For differences between means, a probability of <0.05 was considered statistically significant.

Example 2

Antibody Inhibition of Factor XII in Baboons Reduces Platelet Deposition from Blood in Extracorporeal Membrane Oxygenators This example describes the characterization of FXII-specific monoclonal antibody 5C12 and its ability to function as an anticoagulant and reduce platelet accumulation. In addition, using a primate model, these studies show that FXII inhibition reduces platelet activation and deposition within membrane oxygenators in both heparinized and non-heparinized baboons.

5C12 Inhibits FXIIa

Figure 3A:
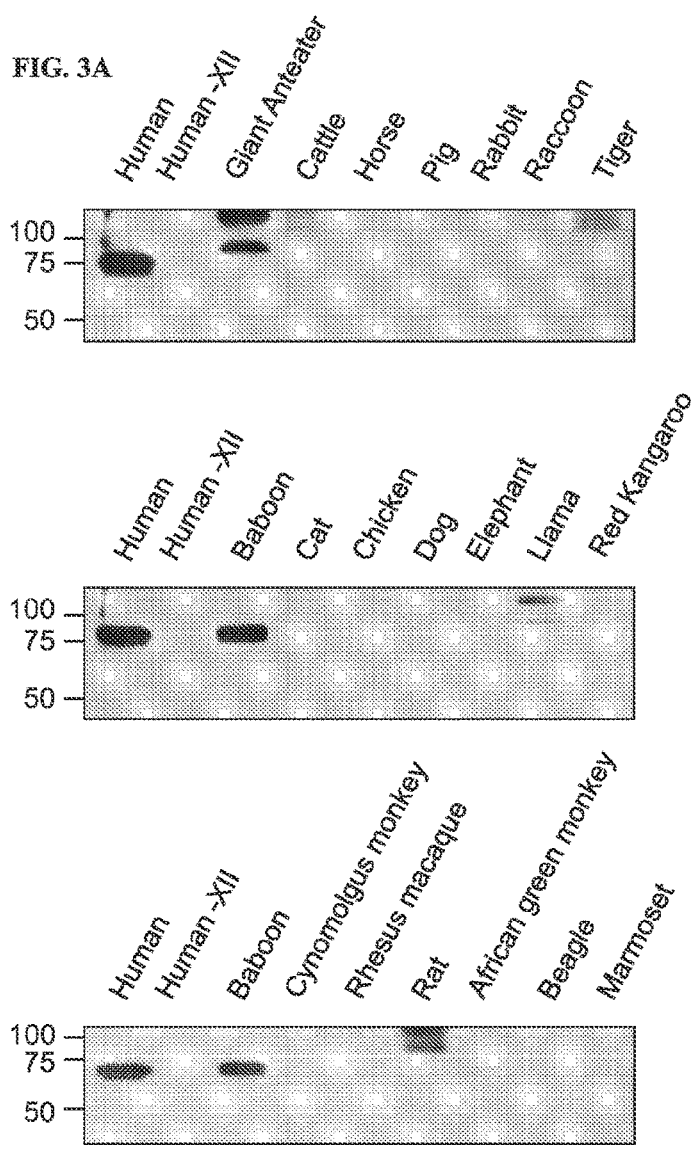
FIG. 3A-3C: Species specificity of 5C12.
Figure 3B:
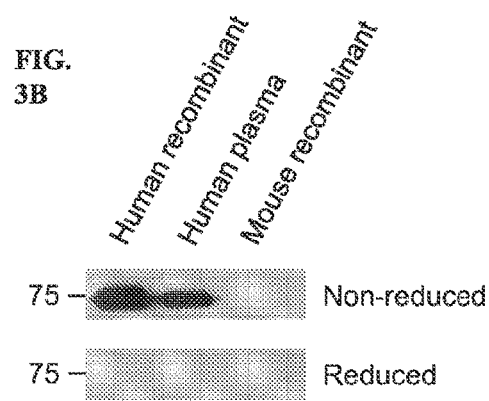
Figure 3C:
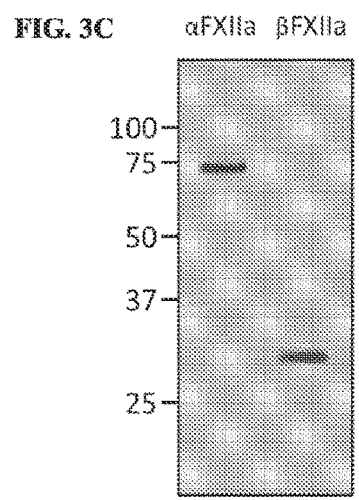
Figure 4A:
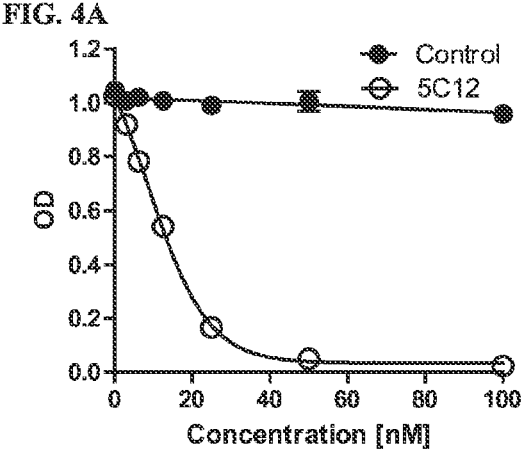
FIGS. 4A-4E: 5C12 inhibits FXII activation and FXIIa activity.
Figure 4B:
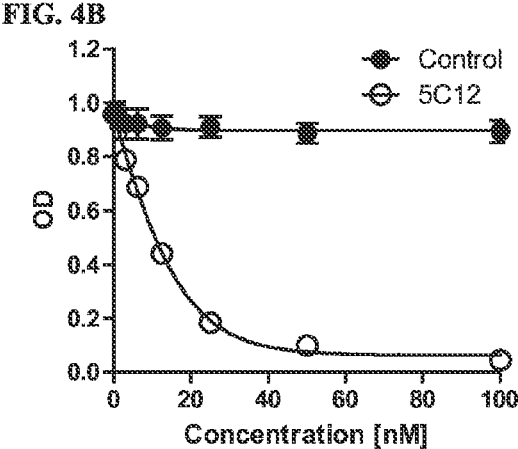
Figure 4C:
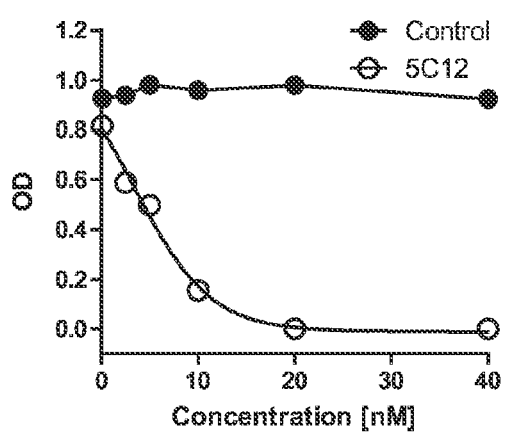
Figure 4D:
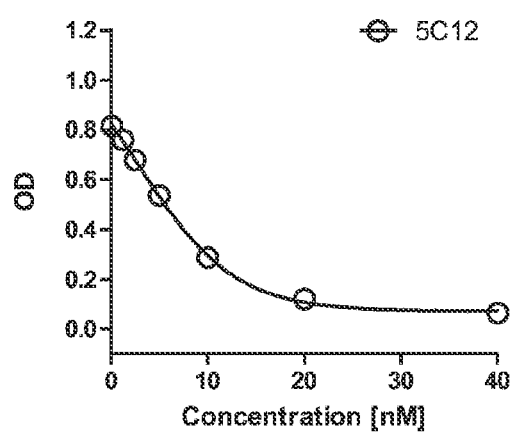
Figure 4E:
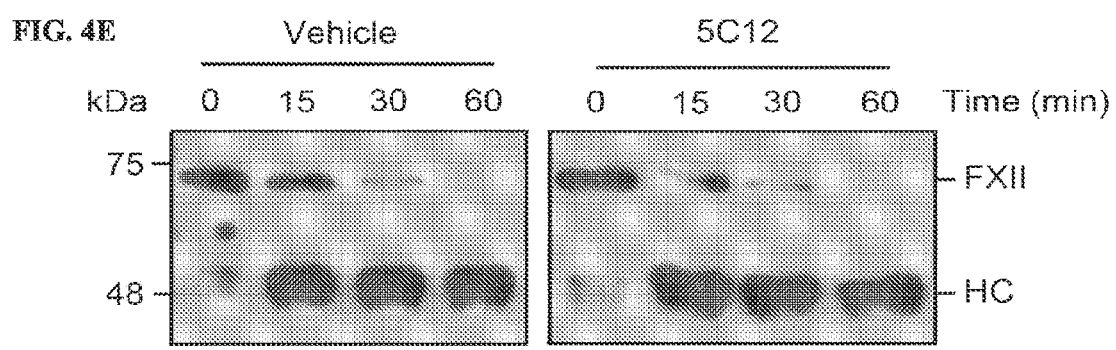

The 5C12 MAb recognized both the alpha and beta forms of human and baboon and African green monkey FXII by binding to the protease domain on Western blots, but did not recognize FXII of other species tested (FIGS. 3A-3C) and prolonged the aPTT of both human and baboon plasma that was mixed with FXII-depleted plasma (FIGS. 2A-2B), but not of other species tested (FIGS. 2C-2F). Increasing concentrations of 5C12 prolonged the clotting time in human and baboon plasma (FIG. 1A-1B), reaching the aPTT of FXII-depleted plasma at around 50 to 60 µg/ml (330-400 nM), and suggesting inhibition of FXII by a 1:1 complex with antibody. In comparison to CTI, a well-characterized FXIIa inhibitor (Hansson et al., *J Thromb Haemost* 2014; 12:1678-1686), 5C12 was more potent, with measurable aPTT prolongation at 200 nM (FIG. 1C). 5C12 prevented generation of amidolytic activity when FXII was exposed to contact activators (FIGS. 4A-4C) and blocked the amidolytic activity of an equimolar amount of FXIIa, consistent with active site inhibition (FIG. 4D). 5C12 did not inhibit activation of FXII by kallikrein in the presence of dextran sulfate (FIG. 4E). These data show that 5C12 inhibits FXIIa by binding to the catalytic domain of FXII.

5C12 is a Potent Anticoagulant In Vivo

Figure 5E:
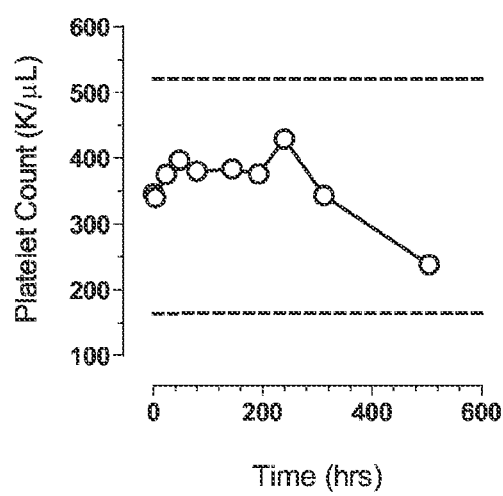
Figure 5F:
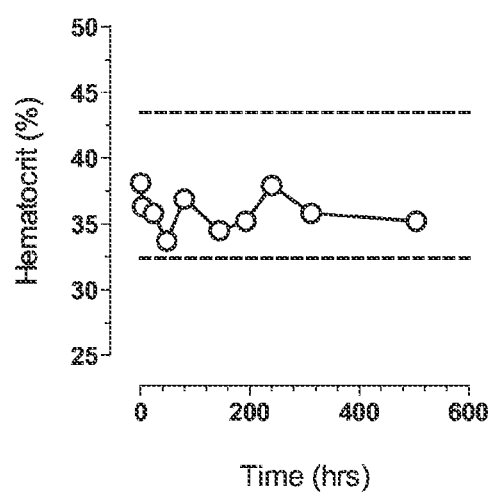
Figure 5G:
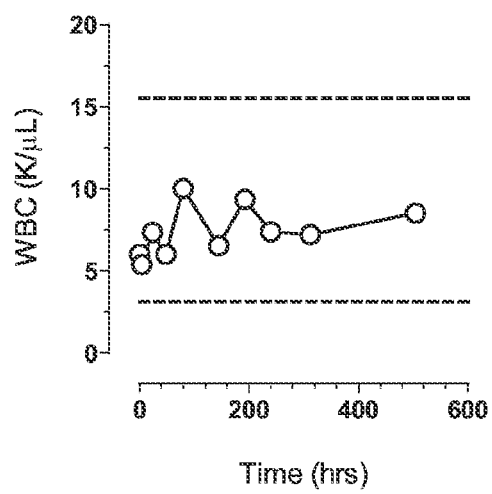
Figure 5H:
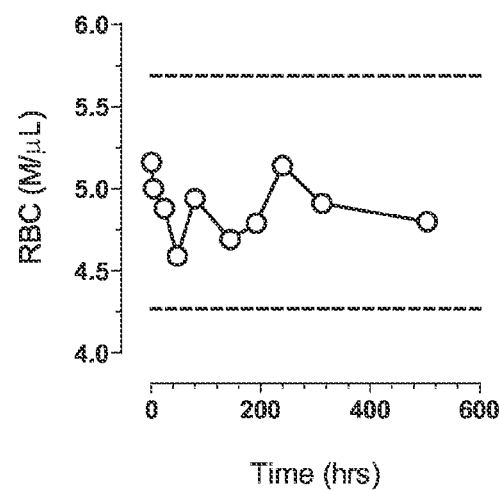

Administration of 5C12 increased the aPTT four-fold and ACT three-fold in the first hours of dose escalation (FIGS. 5A-5B), without affecting prothrombin time or circulating TAT levels (FIGS. 5C-5D). Complete blood count parameters, including platelet count, hematocrit, and white and red blood cell count remained within the normal reference range (FIGS. 5E-5H) (Hainsey et al., *Lab Anim Sci* 1993; 43:236-243).

5C12 Inhibits Platelet Deposition in an Extracorporeal Membrane Oxygenator

Heparin increased the aPTT 1.6-fold (1.5 to 1.7) over baseline and increased ACT 1.3-fold (1.2 to 1.5) over baseline (Table 1) in baboons. Administration of 5 mg/kg of 5C12 increased the aPTT 2.6-fold (2.3 to 3.3) and ACT 1.8-fold (1.7 to 1.9) without increasing the hemostatic impairment marker, PT. The combination of heparin and 5C12 increased aPTT 3.9-fold (3.4 to 4.5) and ACT 2.3-fold (2.1 to 2.3) without increasing the hemostatic impairment marker, PT. The anticoagulant effect of 5C12 in the aPTT assay was measurable for 3 days (FIGS. 5A-5B).

TABLE 1

Changes in coagulation parameters during anticoagulation and extracorporeal membrane oxygenator perfusion. APTT, ACT, and PT values were determined in three baboons before exposure to an anticoagulant, and at the beginning (0 min) and end (60 min) of each experiment.

| | APTT (sec) | | ACT (sec) | | PT (sec) | |
|---|---|---|---|---|---|---|
| | | | Baseline (n = 6) | | | |
| | 30.7 ± 0.5 | | 208.5 ± 11.4 | | 8.3 ± 0.2 | |
| | Start (0 min) | End (60 min) | Start (0 min) | End (60 min) | Start (0 min) | End (60 min) |
| Vehicle (n = 2) | 30.2 ± 0.5 | 33.4 ± 0.2 | 200.5 ± 12.6 | 176.8 ± 11.4 | 8.2 ± 0.2 | 8.3 ± 0.4 |
| Heparin (20 U/kg) (n = 4) | 49.1 ± 2.4 | 34.2 ± 0.8 | 271.5 ± 11.2 | 190.6 ± 5.9 | 8.6 ± 0.2 | 8.7 ± 0.2 |
| 5C12 (5 mg/kg) (n = 3) | 79.5 ± 6.9 | 82.9 ± 4.8 | 381.5 ± 8.3 | 394.8 ± 9.9 | 8.4 ± 0.1 | 8.6 ± 0.1 |
| 5C12 (5 mg/kg) + Heparin (20 U/kg) (n = 3) | 121.0 ± 9.7 | 77.5 ± 2.7 | 472.6 ± 25.6 | 378.7 ± 11.9 | 9.0 ± 0.1 | 8.8 ± 0.2 |

In non-anticoagulated baboons, platelet deposition in the oxygenator was detectable at 5 minutes (FIG. 6A) and platelet retention rates averaged 1.64±0.13 billion per min (bpm) between 30 and 60 minutes from the start of perfusion (FIG. 6B). In heparinized baboons, platelet deposition was measurable at 25 minutes and grew at a rate of 1.21±0.08 bpm between 30 and 60 minutes (FIG. 6B). Pretreatment with 5C12 reduced platelet retention rate to 0.61±0.05 bpm without heparin and to 0.56±0.04 bpm with heparin (FIG. 6B). End-point platelet deposition was reduced from 52±11 to 24±4 billion platelets, and end-point fibrin content of the oxygenator was reduced from 45±15 mg to 15±4 mg by supplementing heparin with 5C12 (FIGS. 6C-6D). Fibrin and platelet contents showed a significant correlation ($R^2$=0.99), suggesting that platelet activation plays a key role in oxygenator thrombus formation (FIG. 6E). Hemostasis parameters (bleeding time, bleeding volume, and bleeding rate remained within the normal range for baboons for all treatment regimens (FIGS. 9A-9C).

Figure 8A:
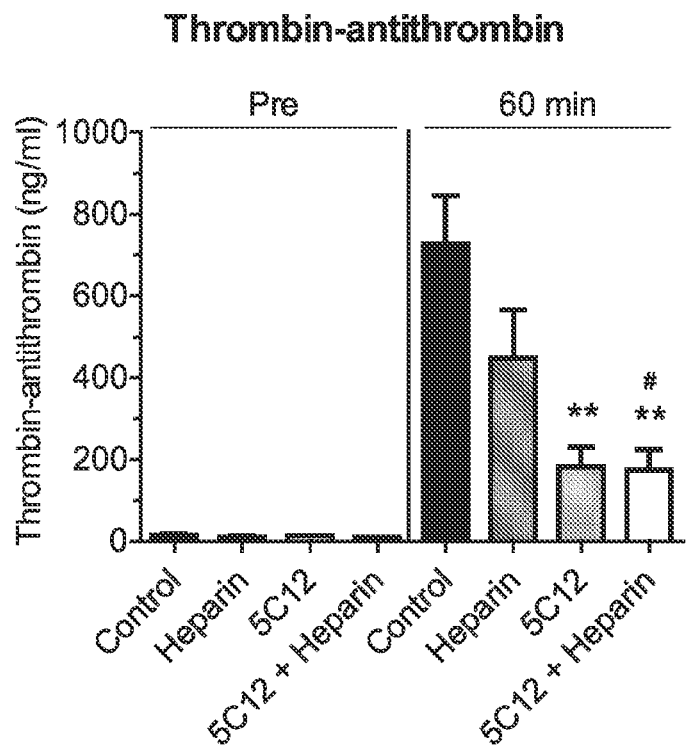
FIGS. 8A-8B: Measurement of thrombosis markers at the end of ECMO shunt studies. Thrombosis markers measured were thrombin-anti-thrombin (TAT) using Enzygnost TAT micro ELISA kit (Siemens Healthcare Diagnostics Products GmbH) (FIG. 8A) and platelet factor 4 using Human CXCL4/PF4 DuoSet ELISA kit (Bio-Techne Corporation, Minneapolis, MN) (FIG. 8B). Data shown are measurements taken at the end of each study. Baseline measurements taken prior to the study were not different from each other and are shown on the left side of each panel.
Figure 8B:
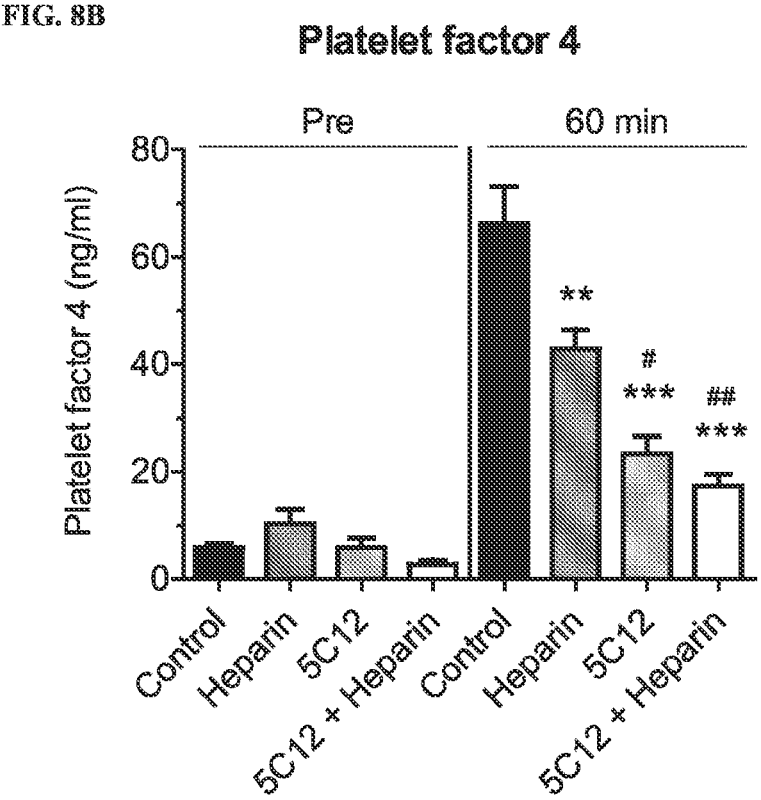
Figure 10A:
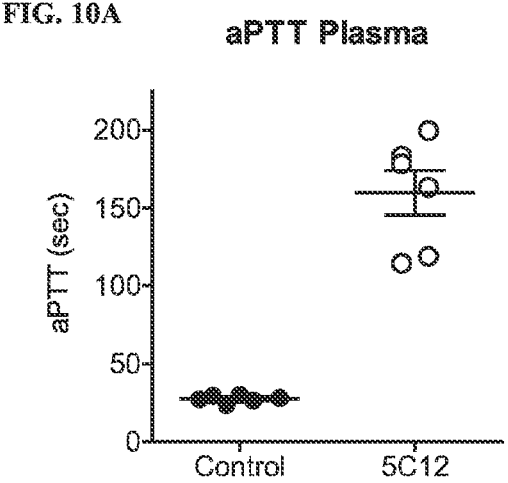
FIGS. 10A-10F: Coagulation assessment in spiked human blood samples. Blood samples were collected into a 1/10th volume of 3.2% sodium citrate from six volunteers.
Figure 10B:
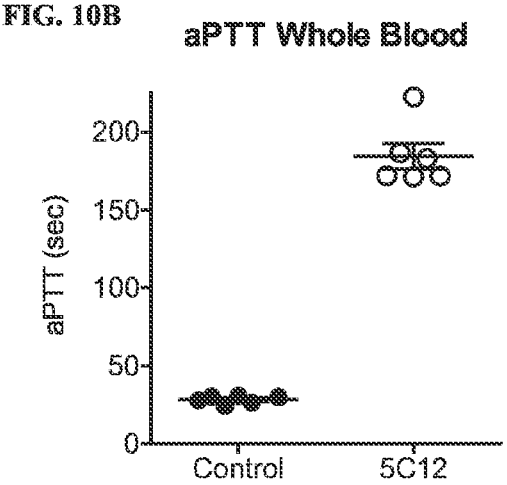
Figure 10C:
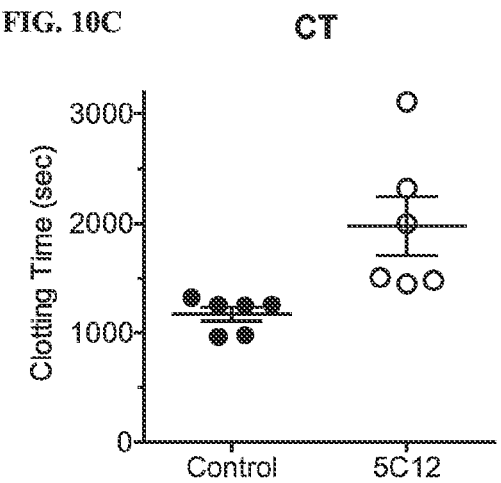
Figure 10D:
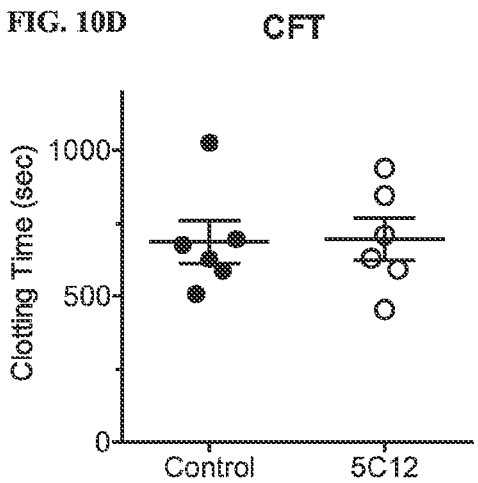
Figure 10E:
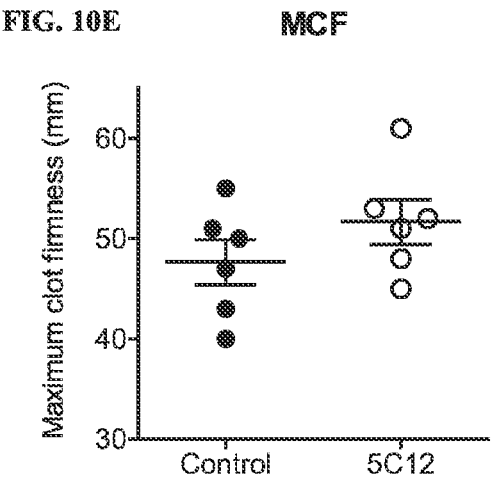
Figure 10F:
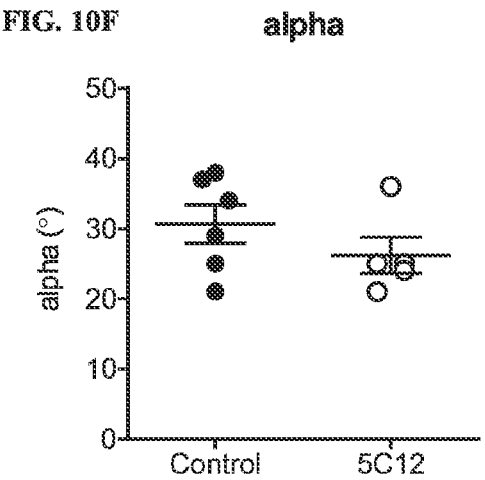

In non-anticoagulated baboons, plasma TAT levels increased 60-fold from the baseline of 12 ng/ml (range 8-20 ng/mL) to 726 ng/mL (range 521-938 ng/mL) after oxygenator perfusion (FIG. 8A). In heparinized baboons, TAT increased 37-fold, while TAT increased 14-fold when 5C12 was combined with heparin. Plasma PF4 levels increased 11-fold in untreated, 7-fold in heparinized, and 3-fold in 5C12+heparin combination-treated baboons after a 60-minute oxygenator perfusion (FIG. 8B).

Therapeutic Applications

The study disclosed herein demonstrates the first time that even though 5C12 is an anticoagulant that targets the contact system, intravenous administration of the anticoagulant anti-FXII MAb, 5C12, significantly reduces platelet accumulation in extracorporeal membrane oxygenators in non-human primates. 5C12 binds to the FXII catalytic domain, where it is in position to block the protease active site upon FXII zymogen conversion to FXIIa by kallikrein. The 5C12 MAb inhibits clotting in contact activation-initiated coagulation tests such as aPTT and ACT, primarily (if not exclusively) by limiting thrombin generation. While inhibition of FXII activity was not expected to have a profound effect on initial platelet adhesion to, and subsequent accumulation on the membrane, the data indicate that platelet activation in the oxygenator is strongly supported by FXIIa activity and likely contributes, in addition to fibrin accumulation, to occlusive device failure despite the calculated initial low average wall shear rates in the membrane oxygenator cartridge.

For the baboon experiments, a low dose of heparin that produced a measurable anticoagulant effect in the aPTT assay but did not completely prevent quantifiable platelet accumulation was used in the membrane oxygenator. This dose prevented occlusion of the cartridge while still allowing for the antithrombotic effect of 5C12 to be demonstrated. High doses of heparin are used during pediatric ECMO, which leads to bleeding complications (ELSO Anticoagulation Guideline. 2015). The findings that 5C12 is demonstrably antithrombotic in the presence of heparin suggests that heparin could be administered at lower doses when used in combination with 5C12, and this could offer a potentially safer approach to anticoagulation during ECOS that involves perfusion of blood through devices, such as ECMO, as FXII has no known role in hemostasis.

The physiological functions of FXII have not been established. The FXII zymogen protein is found in most terrestrial vertebrates but is absent in birds and aquatic-dwelling cetaceans (Ponczek et al., *J Thromb Haemost* 2008; 6:1876-1883). Of the terrestrial vertebrates, mammals alone synthesize FXI, which acts as a bridge between FXII and downstream thrombin generation. However, FXIIa can shorten the contact-initiated clotting time of FXI-deficient plasma, in vitro (Puy et al., *J Thromb Haemost* 2013; 11:1341-1352), possibly because FXIIa could cleave several macromolecular substrates, including some inhibitors of coagulation, such as antithrombin. Non-physiological or pathogenetic roles for FXII have been shown, mostly under experimental conditions, and a few also clinically, by a number of investigators. For example, FXII facilitates experimental embryo implantation (Matsubayashi et al., *Am J Reprod Immunol* 2008; 59:316-322; Kawato et al., *Reprod Fertil Dev* 2009; 21:840-847), promotes tissue repair, angiogenesis, and mitogenesis (LaRusch et al., *Blood* 2010; 115:5111-5120), enhances vasodilation and inflammation through kallikrein activation and bradykinin generation (Björkqvist et al., *Thromb Haemost* 2013; 110:399-407), may contribute to autoimmune disease pathogenesis through dendritic cell interactions (Gobel et al., *Nat Commun* 2016; 7:11626), may contribute to experimental thrombotic processes (U.S. Pat. No. 9,574,013; Larsson et al., *Sci Transl Med* 6:222ra17, 2014; Worm et al., *Ann Transl Med* 3:247, 2015), and FXII produced by neutrophils appears to play a role in normal neutrophil function (Stavrou et al., *J Clin Invest* 2018; 128:944-959). Despite all these data, pathology has not been associated with FXII deficiency, although deficiency of natural FXIIa inhibitors, such as C1Inh can produce localized and systemic reactions that would be consistent with reduced inhibition of contact activation and excessive bradykinin generation, such as seen in angioedema. The data disclosed herein support the premise that FXII inhibition could also be utilized in medical procedures where both thrombus formation and bleeding are immediate risks. This may include ECOS systems, including hemodialysis, ECMO, left ventricular assist devices, or cardiopulmonary bypass (Cheng et al., *Ann Thorac Surg* 2014; 97:610-616).

Based on epidemiological observations showing an association between low-normal FXII levels and cardiovascular disease, some investigators extrapolated from these data to suggest that severely reduced FXII activity (such as FXII deficiency) could be associated with an increased risk of thrombosis (Goodnough et al., *Med* 1983; 62:248-255; Kuhli et al., *Am J Ophthalmol* 2004; 137:459-464). However, the incidence, prognosis, or prevalence of cardiovascular disease in FXII deficiency is not established, and other observational studies of the general population found no association between FXII levels and predisposition to thrombosis (Girolami et al., *J Thromb Thrombolysis* 2004; 17:139-143; Zeerleder et al., *Thromb Haemost* 1999; 82:1240-1246). Deficiency of FXI, a substrate of FXIIa, may cause a mild to moderate bleeding diathesis, while also reducing the risk of thrombosis (Salomon et al., *Thromb Haemost* 2011; 105:269-273; Preis et al., *Blood* 2017; 129: 1210-1215; Salomon et al., *Blood* 2008; 111:4113-4117). FXI inhibitors are in clinical development (Tillman et al., *Blood Rev* 2018; 32:433-448; Gailani et al., *J Thromb Haemost* 2015; 13:1383-1395), with a FXI antisense oligonucleotide demonstrating improved outcomes in a phase 2 trial for venous thromboembolism prevention following knee replacement surgery (Buller et al., *N Engl J Med* 2015; 372:232-240). Inhibition of either FXI or FXII with antisense oligonucleotides showed similar antithrombotic efficacy and safety in a rabbit model of catheter-induced thrombosis (Yau et al., *Blood* 2014; 123:2102-2107). The development of FXII inhibitors is at an early stage. Some monoclonal anti-FXII/FXIIa antibodies have already been described, but none have reached human trials. Several decades ago, the monoclonal anti-FXII antibody C6B7 was found to reduce hypotension in a baboon model of sepsis but did not diminish signs of disseminated intravascular coagulation (DIC); however, this antibody only inhibited FXII activity ~60% in baboon plasma (Pixley et al., *J Clin Invest* 1993; 91:61-68). More recently, the anti-FXIIa monoclonal antibody 3F7 reduced thrombus formation in a rabbit ECMO model and is being evaluated as a potential treatment for hereditary angioedema (Larsson et al., *Sci Transl Med* 2014; 6:222ra17; Worm et al., *Ann Transl Med* 2015; 3:247; Farkas et al., *Expert Opin Investig Drugs* 2018; 27:87-103). Other approaches to target FXII include a synthetic peptide based on CTI (Baeriswyl et al., *ACS Chem Biol* 2015; 10:1861-1870), anti-FXII nanobodies (de Maat et al., *Thromb Haemost* 2013; 110:458-468), and nuclease-resistant FXII inhibitory RNA aptamers (Woodruff et al., *J Thromb Haemost* 2013; 11:1364-1373). FXII antisense oligonucleotides have also been tested in animal studies (Yau et al., *Blood* 2014; 123:2102-2107). Since antisense oligonucleotides require weeks to reach efficacy and produce sustained FXII deficiency (Buller et al., *N Engl J Med* 2015; 372:232-240) they could well be useful for long-term thromboprophylaxis.

The results of this study indicate that 5C12 MAb forms an inhibitory complex with circulating FXII, in vivo, providing effective reduction of platelet-dependent thrombus formation in an extracorporeal membrane oxygenator device, without appreciable change in the template bleeding time. Importantly, it was demonstrated that the combination of 5C12 with heparin improves the antithrombotic efficacy of anticoagulation with heparin alone.

Example 3

Evaluation of FXIIa Inhibition Using 5C12 (AB053) in a Baboon Model of Lethal *S. aureus* Exposure This example describes studies to evaluate the effect of prophylactic 5C12 (hereinafter referred to as "AB053") in a baboon model of lethal systemic inflammatory response syndrome (SIRS). SIRS, with or without intravascular coagulation and/or coagulopathy, can sometimes be observed in patients who receive bactericidal antibiotics to prevent or treat sepsis. A "saturating" dose of AB053 (10 mg/kg) or no antibody was administered intravenously to baboons immediately before a 2 hour-long intravenous infusion of 30 billion heat-inactivated *S. aureus* bacteria. Two additional AB053 doses were administered 8 hours (10 mg/kg) and 24 hours (5 mg/kg) later. Vital signs were monitored and blood samples were taken to measure organ functions and markers of coagulation, inflammation, and organ injury. Untreated animals (n=3) developed severe SIRS and shock with significant alterations in virtually all monitored markers within 6 to 24 hours and had to be euthanized within 48 hours. By contrast, baboons that received AB053 (n=3) survived without development of SIRS, severe illness, and major changes in blood markers. Survivors were euthanized seven days later for terminal analyses. The results of this study indicate that near-complete FXIIa inhibition with AB053 may prevent the development of *S. aureus* exposure-induced lethal SIRS in baboons.

Biochemical Tests

Blood glucose was measured using a Contour Next blood glucose meter (Bayer HealthCare LLC, Mishawaka, IN). Blood lactate was measured by Lactate Scout (EKF Diagnostics GmbH, Barleben, Germany). Serum alanine aminotransferase, aspartate aminotransferase, amylase, creatinine, blood urea nitrogen, potassium, phosphate, and lactate dehydrogenase levels were measured using standard clinical tests. Myeloperoxidase (MPO) activity in plasma was quantified by using a FluoroMPO myeloperoxidase detection kit (Cell Technology, Fremont, CA)

CBC

Complete blood count (CBC) was measured using blood collected into $K_2$-EDTA coated vials and analyzed using an Abaxis Vetscan HM5 (Abaxis, Union City, CA).

aPTT

The activated partial thromboplastin time (aPTT) was determined in plasma samples anticoagulated with 0.32% sodium citrate (final concentration). 50 µL of plasma was incubated with 50 µL of aPTT reagent (Pacific Hemostasis Kontact, Cat #100312TS, Thermo Fisher Scientific, Waltham, MA) for 3 minutes at 37° C. After incubation, 50 µL of 25 mM $CaCl_2$ (Pacific Hemostasis $CaCl_2$, Cat #100314TS, Thermo Fisher Scientific, Waltham, MA) was added and time to clot was determined on a KC4A Analyzer (Amelung GmbH, Lemgo, Germany).

PT

The prothrombin time (PT) was determined in plasma samples anticoagulated with 0.32% sodium citrate. 50 µL of plasma was incubated for 1 minute at 37° C. After incubation, 100 μL of Pacific Hemostasis Thromboplastin-DS (Cat #100354TS, Thermo Fisher Scientific, Waltham, MA) was added and time to clot was determined on a KC4A Analyzer.

Antithrombin ELISA Assays

Complexes of activated factors with antithrombin (FXIIa-AT, Kallikrein-AT, FXIa-AT, FVIIa-AT, TAT) were measured via custom enzyme-linked immunosorbent assays. Plates were coated overnight at 4° C. with one of the following affinity-purified antibodies (100 μL/well): (i) goat anti-human FXII (2 μg/mL); (ii) sheep anti-human FXI (2 μg/mL); (iii) sheep anti-human thrombin (2 μg/mL), all from Affinity Biologicals; or (iv) goat anti-human FVII (0.3 μg/mL, R&D Systems, Minneapolis, MN, USA) or (v) (sheep anti-human prekallikrein antibody, Affinity Biologicals). After each step, plates were washed with PBS containing 0.1% Tween-20 and then blocked with the same buffer containing 1% BSA. EDTA plasma samples were incubated for 60 minutes in PBS containing 1% BSA, 5 mM EDTA, 5 mM benzamidine hydrochloride, 0.1% Tween-20. Biotinylated affinity purified sheep anti-human antithrombin (0.5 μg/mL, Affinity Biologicals) was used for detection followed by streptavidin-HRP (400 ng/mL, Jackson ImmunoResearch Laboratories, West Grove, PA, USA) and ortho-phenylenediamine (OPD) as substrate. The absorbance values were recorded at 492 nm.

Other ELISA Assays

Plasma kininogen (all forms), plasminogen activator inhibitor 1 (PAI-1) and tissue type plasminogen activator (tPA) were quantified using DuoSet ELISA kits (R&D Systems, Minneapolis, MN). For plasmin-antiplasmin complexes, affinity purified goat anti-human plasminogen (2 μg/mL, Affinity Biologicals) was used as capture and horseradish peroxidase-conjugated goat anti-human α2-antiplasmin (1 μg/mL, Affinity Biologicals) as detection antibodies. D-dimer ELISA was done using mouse monoclonal anti-human D-dimer (clone DD1, 1 μg/mL, Novus Biologicals, Littleton, CO) as capture and horseradish peroxidase-conjugated sheep anti-human fibrinogen as detection antibody (2 μg/mL, Affinity Biologicals). Plasma cytokines were quantified using MILLIPLEX MAP Non-Human Primate Cytokine Magnetic Bead Panel (EMD Millipore, Billerica, MA). C3b was measured using mouse monoclonal anti-human C3b/c IgG, clone C3-28 (Cell Sciences) for capture, and goat anti-human C3 (Complement Technologies) as detection antibody. C5b-9 was measured using the monoclonal antibody aE11 (Enzo Life Sciences) as capture antibody and anti-human C6 biotinylated antibody (Quidel Corporation, San Diego, CA) was used as detection antibody. Nucleosomes were quantified using a Cell Death Detection ELISA PLUS kit (Roche Diagnostics GmbH, Mannheim, Germany).

Bacteria

S. aureus subspecies aureus Rosenbach (ATCC 12598) was purchased from American Type Culture Collection (ATCC, Manassas, VA). To control the standard dosing of bacteria and avoid potentially confounding effects by live organisms, exponential-phase cultured S. aureus was extensively washed with saline solution and counted, then heated for 1 hour at 70° C. Aliquots were stored at −80° C. until use. For uniformity, animals were challenged with bacteria from a single preparation.

Animals

A total of 6 animals were used for these terminal studies. Six healthy juvenile baboons (*Papio anubis* and *ursinus*) weighing between 6.7 and 20.2 kg were used. Data from the control group animals was published as part of the study using a FXI antibody, AB023 that inhibits contact activation of FXI (Silasi et al., *Blood Advances* 3(4):658-669 2019).

Experiments

The experimental design included 2 arms: a control group (n=3) and a treated group (n=3). Animals in both groups were challenged with 30 billion heat-inactivated S. aureus bacteria (an established lethal dose in baboons), given by IV infusion over 2 hours. The untreated control group received only the bacterial infusion, whereas the treated group received a bolus of AB053 (10 mg/kg) 30 minutes before the bacterial infusion was started (pretreatment) and two additional IV bolus injections at 8 hours (10 mg/kg) and at 24 hours (5 mg/kg) post S. aureus infusion start. The time point at which the bacterial infusion began was designated as T0. Eight hours after the start of the bacterial infusion (T+8), the animals were returned to the recovery cage and observed until they exhibited signs of unrecoverable organ failure and septic shock, at which time they were humanely euthanized. Surviving animals were euthanized on day 7.

Critical Care Monitoring

Respiration and heart rate, temperature and mean systemic arterial pressure (MSAP) were monitored with a Cardell Max-12 HD Duo monitor. These physiologic data were recorded before each blood sample collection, every 15 minutes for the first 8 hours until the animals were returned to the recovery cage, and then once daily for 3 days, and then on day 7.

Blood Sample Collection

Systemic blood samples were collected at T−0.5, 0, +2, +4, +6, +8, +24, +48, +72 and +168 hours, using the following anticoagulants and blood volumes: 3 ml of blood into $K_2$-EDTA coated vials, 2 mL of blood into vials containing 0.32% sodium citrate, and 1 mL of blood for serum. The total amount of blood that was withdrawn over the first 24 hours period was less than 10% of the animals' calculated blood volume (70 mL/kg).

Data and Statistical Analysis

Prism (GraphPad Software 7.0d) was used for statistical analysis. Data are given as mean±standard error of the mean. Comparisons between 2 groups were performed using a 2-tailed Student's t-test for each time point. Results were considered significant at *$p<0.05$, $p<0.01$, *$p<0.001$. The log-rank Mantel-Cox test was used for comparison of survival curves.

The primary endpoint of this study was survival. While in the untreated (negative control) group, 2 of 3 animals needed to be euthanized within 24 hours, and the third on the second day, all three AB053-treated animals survived to 7 days. AB053 pretreatment increased aPTT to greater than 100 seconds but did not potentiate the aPTT elevation resulting from S. aureus exposure observed in control animals. In addition, AB053 treatment attenuated the S. aureus-induced increase in PT. Coagulation activation was assessed as changes in the levels of antithrombin complexes with a number of coagulation enzymes. Antithrombin-enzyme complexes increased within hours of S. aureus exposure, and AB053 treatment blunted these responses. AB053 treatment also attenuated fibrinogen consumption and activation of fibrin(ogen) lysis. Analysis of markers for complement activation and cell death, which are both increased after S. aureus exposure, were reduced in the AB053 arm. Activation of several inflammatory cytokines (cytokine storm) that was observed within hours after S. aureus exposure was significantly reduced by AB053. During the first 8 hours post exposure, vital signs of all animals were closely monitored, showing that AB053 treatment counteracted hypotension caused by S. aureus exposure. AB053 also reduced liver, kidney and pancreas injury or helped preserve their function. AB053 prevented white blood cell and platelet count reduction, and reduced systemic markers of platelet activation compared to untreated animals. AB053 also protected against hemoconcentration.

Conclusions

The results of this study indicate that AB053 provides effective protection from *S. aureus* exposure-induced lethal SIRS in baboons. Compared to untreated controls, all AB053 treated animals survived a lethal dose of *S. aureus*. The results suggest that FXII plays an important pathogenetic role in the development of *S. aureus* exposure-induced lethal SIRS.

Example 4

Humanization of 5C12 (AB053)

This example describes the generation of a library of humanized antibodies based on the sequence of murine antibody 5C12 (also referred to herein as "AB053").

Antibodies

AB053 was generated as described in Example 1. Humanization of AB053 was performed by CDR-grafting technology at LakePharma (Belmont, CA).

Construction of Expression Vectors

Full-length antibody genes were constructed by first synthesizing the variable region sequences designed in the humanization experiments. The sequences were optimized for expression in mammalian cells. These variable region sequences were then cloned into expression vectors that already contained human IgG4 (S241P hinge modified) Fc domains.

For comparison, the variable regions of the murine AB053 heavy and light chains were constructed as full-length chimeric chains using the same backbone human Fc sequences as described above.

Small Scale Production

The nine humanized antibodies generated by combination of the three humanized heavy chains and three humanized light chains underwent 0.01 L production. The chimeric parental antibody was also scaled-up for direct comparison. Plasmids for the indicated heavy and light chains were transfected into suspension HEK293 cells using serum-free chemically defined media for antibody production. Full length antibodies were then purified from conditioned media using MabSelect SuRe Protein A resin (GE Healthcare).

Results

Three humanized heavy chains were designed based on two different human heavy chain acceptor frameworks and three humanized light chains were designed based on two different human light chain acceptor frameworks (Table 2).

TABLE 2

Humanized chain information

| Chain Name | Chain Type | Acceptor Framework |
|---|---|---|
| H7879 (chimeric parental) | Heavy chain | N/A |
| L7879 (chimeric parental) | Light chain | N/A |
| H7880 (Humanized HC1) | Heavy chain | HC framework 1 |
| H7881 (Humanized HC2) | Heavy chain | HC framework 1 |
| H7882 (Humanized HC3) | Heavy chain | HC framework 2 |
| L7880 (Humanized LC1) | Light chain | LC framework 1 |
| L7881 (Humanized LC2) | Light chain | LC framework 1 |
| L7882 (Humanized LC3) | Light chain | LC framework 2 |

The first humanized heavy/light chain utilizes the first respective framework and contains the most human sequence with minimal parental antibody framework sequence (Humanized HC1 and LC1; SEQ ID NOs: 7 and 9, respectively). The second humanized heavy/light chain uses the same framework as humanized HC1/LC1 but contains additional parental sequences (Humanized HC2 and LC2; SEQ ID NOs: 13 and 17, respectively). The third humanized heavy/light chain utilizes the second respective framework and, similar to humanized HC2/LC2, also contains additional parental sequences fused with the human framework (Humanized HC3 and LC3; SEQ ID NOs: 15 and 19, respectively).

The humanized heavy and light chains were then combined to create nine variant fully humanized antibodies as well as a chimeric antibody containing the variable regions of the murine monoclonal antibody AB053 and the IgG4, S241P hinge-modified, human Fc region. (Table 3). These antibodies were transiently expressed in HEK293 and produced in small scale production for testing and selection of a lead humanized antibody candidate (see Example 5).

TABLE 3

Antibodies transiently expressed in HEK293 Cells

| Antibody Name | Antibody ID | Titer (mg/L) |
|---|---|---|
| Chimera | PP13892 | 80 |
| HC1 + LC1 | PP13893 | 128 |
| HC1 + LC2 | PP13894 | 59 |
| HC1 + LC3 | PP13895 | 114 |
| HC2 + LC1 | PP13896 | 26 |
| HC2 + LC2 | PP13897 | 63 |
| HC2 + LC3 | PP13898 | 72 |
| HC3 + LC1 | PP13899 | 88 |
| HC3 + LC2 | PP13900 | 71 |
| HC3 + LC3 | PP13901 | 153 |

Example 5

Selection of the Lead Humanized Candidate

This example describes identification of a lead humanized antibody from the nine antibodies described in Example 4. Antibodies were assessed by humanness score, binding characteristics (ELISA, Octet), aPTT and inhibition of FXIIa activity.

Humanness Score

A tool to calculate humanness scores (T20 score) for monoclonal antibodies was developed by LakePharma (Gao et al., *BMC Biotechnology* 13:55, 2013). Briefly, the T20 score represents the degree of antibody humanness by analyzing the primary sequences of the variable regions. For full length heavy chains, a score of 79 or above is indicative of looking human-like; for full length kappa light chains, a score of 86 or above is indicative of looking human-like. Because the T20 scores for full length variable regions could be significantly influenced by the low humanness of the CDR regions which were kept untouched during humanization, T20 scores for the frameworks of humanized antibodies were also calculated. For heavy chain frameworks, a score of 84 or above is indicative of looking human-like; for kappa light chain frameworks, a score of 90 or above is indicative of looking human-like.

ELISA

One μg/mL of human FXII (Enzyme Research Labs, #HFXII 1212) was coated on the ELISA plate at 4° C. overnight. The coated plate was blocked with 2% BSA in phosphate buffered saline (PBS) at room temperature for one hour and then washed three times with PBS. All antibodies to be tested (PP13892-PP13901 or human Fc isotype control) were diluted with sample diluent in an 11 point, 5-fold, serial dilution starting at 10 µg/mL. Each sample was run in duplicate. Each concentration was incubated on the coated plate for one hour at room temperature and then washed three times with PBS. Bound antibody was detected with goat-anti-human IgG-HRP and washed six times with PBS. TMB substrate was added to each well and the reaction was stopped with 1M HCl. Absorbance was read at 450 nm.

$EC_{50}$ for the concentration response curve was calculated by plotting the OD measured at 450 nm against the logarithm of antibody concentration and the $EC_{50}$ was calculated by nonlinear regression analysis.

Octet

Multi-concentration kinetic experiments were performed on the Octet RED96 system (ForteBio). Anti-human Fc biosensors (ForteBio) were hydrated in sample diluent (0.1% BSA in PBS and 0.02% Tween 20) and preconditioned in pH 1.9 Glycine. Antigen was diluted by a 7-point, 3-fold serial dilution starting at 200 nM with sample diluent. Antibodies were diluted to 1 µg/ml with sample diluent and then immobilized onto anti-human Fc biosensors. After baselines were established for 30 seconds in sample diluent, the biosensors were moved to wells containing serially diluted antigen to measure the association and dissociation. Association was observed for 180 seconds and dissociation was observed for 300 seconds. The binding affinities were characterized by fitting the kinetic sensorgrams to a monovalent binding model (1:1 binding).

aPTT

Pooled human plasma (90 µL) anticoagulated with 0.38% sodium citrate (from three individual subjects) was mixed with 10 µL of antibody at varying concentrations (0-75 or 100 µg/mL) or control (PBS) and allowed to incubate at room temperature for 5 minutes. 40 µL of the plasma/antibody mixture was then incubated with 40 µL of aPTT reagent (SynthASil, #0020006800, Instrumentation Laboratory, Bedford, MA) for 3 minutes at 37° C. After the 3 minute incubation, 40 µL of $CaCl_2$ was added and time to clot was determined on a KC4 Analyzer (TCoag). Each sample was assayed in duplicate.

FXIIa Inhibition

A solution of 20 nM FXIIa (Enzyme Research Labs #HFXIIa 3350) in HEPES Buffered Saline (HBS)+0.1% BSA was prepared. Each humanized antibody, as well as the murine monoclonal AB053 and the chimeric antibody, were added to the 20 nM FXIIa solution for a final antibody concentration of 10 nM. 90 µL of each antibody sample was plated in duplicate on a 96-well plate and 10 µL of the chromogenic substrate S-2302 was added to each well. The plate was read at 405 nm for 15 minutes at 37° C.

Calculation of Humanness Scores of Humanized Chains

The T20 scores for the parental and humanized antibodies are shown in Table 4.

TABLE 4

Humanness score for all humanized chains

| VH | Full-length (Framework + CDR) Cutoff = 79 | Framework Only Cutoff = 84 |
|---|---|---|
| Parental | 73 | 72 |
| HC1 | 88 | 93 |
| HC2 | 86 | 89 |
| HC3 | 88 | 90 |

TABLE 4-continued

Humanness score for all humanized chains

| VL | Full-length (Framework + CDR) Cutoff = 79 | Framework Only Cutoff = 84 |
|---|---|---|
| Parental | 63.1 | 68 |
| LC1 | 88 | 96 |
| LC2 | 86 | 93 |
| LC3 | 85 | 91 |

Affinity Measurement by ELISA

Figure 11:
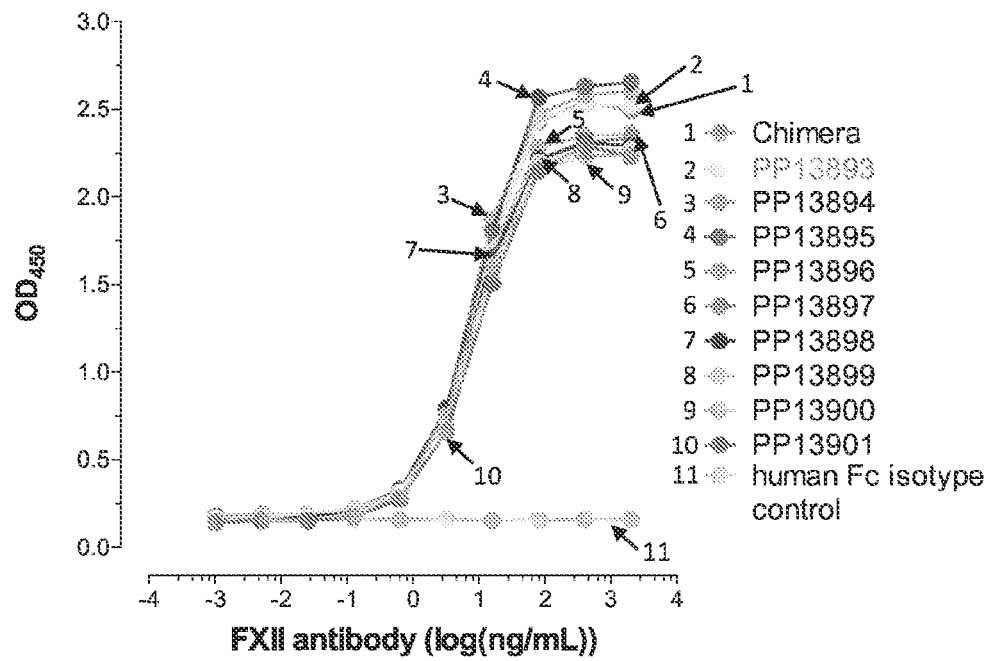
FIG. 11: ELISA curve fitting for humanized and chimeric antibodies. Binding data of each humanized antibody, the chimeric parental antibody, and a human Fc isotype control antibody to human FXII is shown plotted on a semi-logarithmic scale. Samples were run in duplicate and each data point represents the mean of the duplicates±SEM.

The affinity measurement results from the ELISA are shown in FIG. 11 and the calculated EC50 for each antibody is presented in Table 5.

TABLE 5

Calculated $EC_{50}$ of the humanized and chimeric antibodies

| Antibody | ID | $EC_{50}$ (ng/mL) | $R^2$ |
|---|---|---|---|
| Chimera | PP13892 | 9.036 | 0.9989 |
| HC1 + LC1 | PP13893 | 9.116 | 0.9985 |
| HC1 + LC2 | PP13894 | 8.222 | 0.9984 |
| HC1 + LC3 | PP13895 | 9.018 | 0.9990 |
| HC2 + LC1 | PP13896 | 8.238 | 0.9993 |
| HC2 + LC2 | PP13897 | 8.777 | 0.9991 |
| HC2 + LC3 | PP13898 | 8.093 | 0.9994 |
| HC3 + LC1 | PP13899 | 8.479 | 0.9992 |
| HC3 + LC2 | PP13900 | 7.695 | 0.9992 |
| HC3 + LC3 | PP13901 | 9.467 | 0.9987 |

Affinity Measurement by Octet

The affinity measurement of the nine humanized antibodies as well as the chimeric antibody measured by Octet are shown in Table 6.

TABLE 6

Kinetic measurements of the humanized and chimeric antibodies

| Antibody ID | KD (M) | Kon (1/Ms) | Kdis (1/s) |
|---|---|---|---|
| PP13892 | 2.4E−10 | 4.6E+05 | 1.1E−04 |
| PP13893 | 3.0E−10 | 5.3E+05 | 1.6E−04 |
| PP13894 | 3.0E−10 | 5.3E+05 | 1.6E−04 |
| PP13895 | 4.1E−10 | 5.0E+05 | 2.0E−04 |
| PP13896 | 4.4E−10 | 5.0E+05 | 2.2E−04 |
| PP13897 | 1.5E−10 | 6.2E+05 | 9.0E−05 |
| PP13898 | 3.1E−10 | 5.0E+05 | 1.6E−04 |
| PP13899 | 2.7E−10 | 5.6E+05 | 1.5E−04 |
| PP13900 | 3.2E−10 | 5.8E+05 | 1.9E−04 |
| PP13901 | 3.5E−10 | 5.3E+05 | 1.8E−04 |

Figure 12:
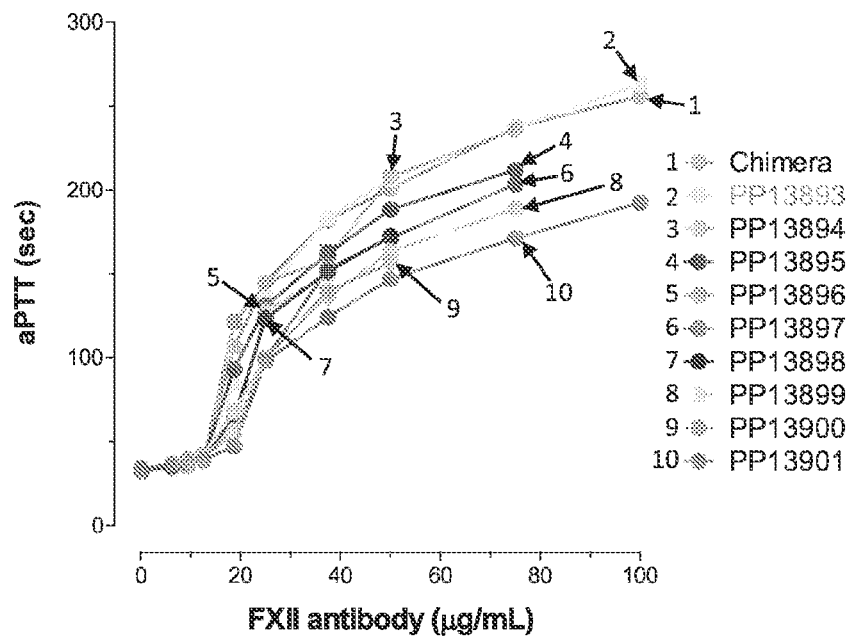
FIG. 12: The effect of the humanized antibodies on concentration-response aPTT curves. All nine humanized antibodies prolonged aPTT in a concentration-dependent manner. The highest possible final concentration of antibody depended on the stock concentration and was either 75 or 100 µg/ml. Each sample was run in duplicate and each data point represents the mean of the duplicates±SEM.

KD = equilibrium dissociation constant
Kon = association constant
Koff = dissociation constant aPTT Screen The results from the aPTT concentration-response curve in human plasma are shown in FIG. 12.

Effect of Humanized Antibodies on FXIIa Activity

Figure 13:
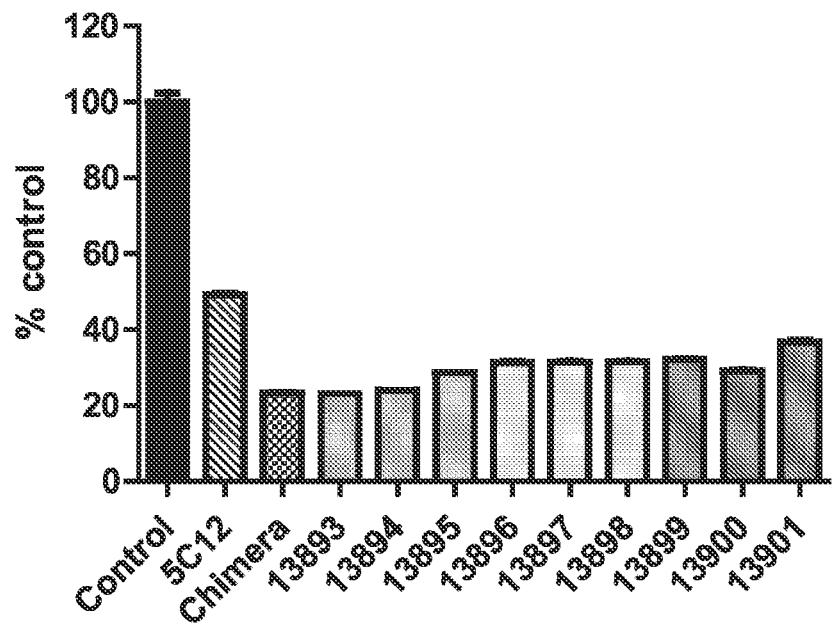
FIG. 13: The effect of humanized antibodies on FXIIa activity. All humanized antibodies (10 nM) inhibited FXIIa (20 nM) activity. Each sample was run in duplicate. The Vmax generated by FXIIa activity (control) was set to 100% and each antibody was compared to control. Data shown is the mean of the duplicates±SEM.

The effect of a fixed concentration of 5C12 antibody variants on FXIIa activity is shown in FIG. 13. Based on the data described above, the humanized antibody PP13893 (HC1+LC1) was selected as the lead candidate for continued development as antibody AB054.

Comparison of AB054 to AB053 on aPTT in Human and Baboon Plasma

Figure 14A:
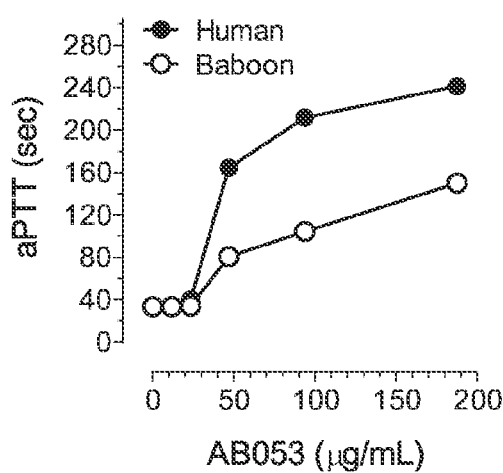
FIGS. 14A-14B: Comparison of AB053 (5C12) and AB054 on aPTT from human and baboon plasma. Comparison of AB053 (FIG. 14A) to the humanized AB054 (FIG. 14B) on aPTT from human (filled circles) and baboon (open circles) plasma. Data represents mean±SEM of 1 to 5 experiments.
Figure 14B:
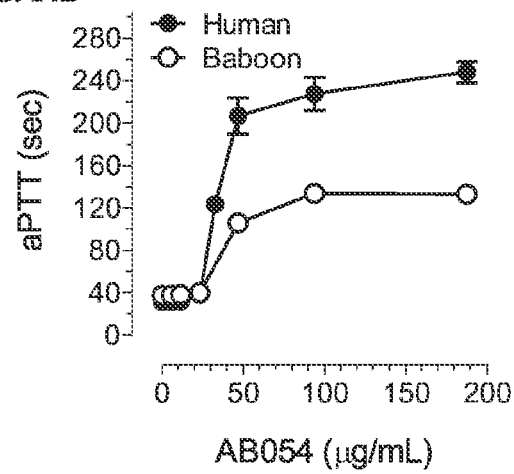

The effect of AB054 on aPTT prolongation in human and baboon plasma was compared to that of the murine parent antibody, AB053 (FIGS. 14A-14B).

Summary

The results described in this example demonstrate that AB053 was successfully humanized, with PP13893 (hereinafter designated as "AB054") selected for further investigation. Antibody AB054 has a KD of 0.3 mM and was shown to prolong aPTT in human and baboon plasma, similar to the murine monoclonal AB053. In addition, AB054 inhibited human FXIIa, confirming that binding to FXII and inhibition of FXIIa activity was maintained after humanization.

Example 6

Evaluation of the Antithrombotic Efficacy of Ab054 in a Membrane Oxygenator Perfusion System This example describes a study to evaluate the antithrombotic effect of AB054 in a model of surface-initiated thrombus formation. The antibody was tested in a model of surface-initiated thrombus formation in baboons. A pediatric membrane oxygenator used for extracorporeal membrane oxygenation was interposed in the extended loop of a baboon arteriovenous shunt. Clot formation and growth within the membrane oxygenator was measured after treatment with AB054, heparin or the combination of the two. The data disclosed herein indicate that AB054 alone or in combination with heparin reduces thrombus formation within a membrane oxygenator device.

Introduction

Blood-contacting medical devices, including catheters, stents, grafts, filters, and extracorporeal organ support systems can fail due to thrombus accumulation in the system, and may also trigger device-associated thromboembolism. To maintain patency, devices that are perfused for various lengths of time require prophylactic anticoagulation that increases the incidence and/or severity of bleeding. Extracorporeal membrane oxygenation (ECMO) has been increasingly used for short-term management of acute respiratory failure, such as in cases of complicated influenza, or in the temporal easement of acute heart failure; however, its benefits are reduced by anticoagulation-associated bleeding. ECMO systems have several components that promote the activation of platelets and the blood coagulation contact system, including the hollow fibers and membranes that are exposed to flowing blood. Inhibiting the blood coagulation contact activation pathway has been proposed as an alternative approach to safer anticoagulation.

aPTT, ACT, PT and CBC

The activated partial thromboplastin time (aPTT) was determined in plasma samples anticoagulated with 0.32% sodium citrate. 40 μL of plasma was incubated with 40 μL of aPTT reagent (SynthASil, #0020006800, Instrumentation Laboratory, Bedford, MA) for 3 minutes at 37° C. After incubation, 40 μL of 20 mM $CaCl_2$ was added and time to clot was determined on a KC4 Analyzer (TCoag, Ltd, Ireland).

The activated clotting time (ACT) was determined in non-anticoagulated blood samples. Immediately after the blood draw, 40 μL blood was added to 40 μL of LupoTek KCT ($r^2$-Diagnostics, South Bend, IN) using a KC4™Analyzer (TCoag, Ltd, Ireland) and time to clot was recorded.

The prothrombin time (PT) was determined in plasma samples anticoagulated with 0.32% sodium citrate. 40 μL of plasma was incubated for 3 minutes at 37° C. After incubation, 40 μL of Dade®Innovin® (Siemens Healthcare, Marburg, Germany) was added and time to clot was determined on a KC4 Analyzer.

Complete blood count (CBC) was measured using 0.25 mL blood collected into $K_2$-EDTA coated vials and analyzed using a Hemavet 950FS (Erba Diagnostics, Germany).

Generation of AB054 Antibody

Experimental grade AB054 was generated by transient expression in HEK293 cells at LakePharma (Belmont, CA). Briefly, each DNA expression construct was scaled up to the appropriate amount for transfection. The plasmid DNA was run on agarose gel for quality assessment and sequence confirmed before proceeding to transfection. Suspension HEK293 cells were seeded in a shake flask and were expanded using serum-free chemically defined medium. On the day of transfection, the expanded cells were seeded into a new flask with fresh medium. Each DNA construct was transiently transfected into HEK293 cells using LakePharma standard operating procedures. The cells were maintained as a batch-fed culture (C4541 and C4542, Medna) until the end of the production run.

The conditioned media from the transient production run was harvested and clarified by centrifugation and filtration. The supernatant was loaded over a Protein A column pre-equilibrated with binding buffer. Washing buffer was passed through the column until the OD280 value (NanoDrop, Thermo Scientific) was measured to be zero. The target protein was eluted with a low pH buffer, fractions were collected, and the OD280 value of each fraction was recorded. Fractions containing the target protein were pooled and filtered through a 0.2 μm membrane filter. The protein concentration was calculated from the OD280 value and the calculated extinction coefficient (1.60 mg/mL$^{-1}$ cm$^{-1}$).

Animals

A total of 9 oxygenator perfusion experiments were performed in two baboons and included 3 treatment groups (Table 7). Experiments were performed over a two-week period in each baboon.

Treatment Groups

Group 1: Heparin (20 U/kg) administered 15 minutes before initiation of membrane oxygenator perfusion (n=3)

Group 2: AB054 (5 mg/kg) administered 30 minutes before initiation of membrane oxygenator perfusion (n=3)

Group 3: AB054 (2 mg/kg) administered 30 minutes and heparin (20 U/kg) administered 15 minutes before initiation of membrane oxygenator perfusion (n=3). In this group, 2 mg/kg AB054 was added on top of the AB054 (5 mg/kg) given 24 hours earlier to maintain full FXII inhibition.

TABLE 7

Summary of treatments for each baboon

| | EXPERIMENT | BABOON 1 | BABOON 2 |
|---|---|---|---|
| WEEK 1 | 1 | 20 U/kg heparin | 20 U/kg heparin |
| | 2 | 20 U/kg heparin | 5 mg/kg AB054 |
| | 3 | | +2 mg/kg AB054 +20 U/kg heparin |
| WEEK 2 | 4 | 5 mg/kg AB054 | 5 mg/kg AB054 |
| | 5 | +2 mg/kg AB054 +20 U/kg heparin | +2 mg/kg AB054 +20 U/kg heparin |

Membrane Oxygenator Perfusion

Non-terminal membrane oxygenator perfusion experiments were performed in juvenile male baboons (*Papio anubis*) weighing 9 to 15 kg. Each baboon had a healed, surgically placed, chronic exteriorized arterio-venous (AV) shunt connecting the femoral artery and vein. The chronic AV shunts were extended to incorporate a saline-primed oxygenator cartridge (Terumo-CAPIOX® RX05, coated hollow fiber design, Terumo Cardiovascular Group, Ann Arbor, MI) for the duration of the perfusion experiment (60 minutes). Perfusion was set at a controlled flow rate of 100 mL/min.

Experiments were conducted on lightly sedated or awake animals that were restrained in a seated position. Animals were sedated with acute ketamine sedation (10 mg/kg) or Telazol (5 mg/kg) before transport from cages to the laboratory. For transport back to the cages, animals were mildly sedated with ketamine (1 to 2 mg/kg as needed) or Telazol (1 mg/kg).

The test articles were administered through, and blood samples were taken from, a silicone rubber extension tubing incorporated into the AV shunt during the experiments. Complete blood counts, including red blood cell counts and hematocrit, were measured daily in each animal, including before and after experiments, and calculated blood loss did not exceed 4% of the total blood volume on any experimental day. Multiple experiments (4 to 5 per animal) were performed in each animal on separate days, over a two-week span. Only animals with shunts that had sufficient unrestricted baseline flow (>250 mL/min) were used in repeat experiments.

Blood Sample Collection

Systemic blood samples (1 mL) were collected proximal to the membrane oxygenator from the midstream of the AV shunt into a 1/10th volume 3.2% citrate anticoagulant at the beginning (0 min) and end (60 min) of each experiment. An additional sample was taken prior to heparin administration (pre heparin) on days when heparin was administered. To measure ACT, 0.2 mL whole blood was collected and analyzed immediately. To measure CBC, 0.25 mL whole blood was collected into $K_2$-EDTA coated tubes and analyzed on an Hemavet 950FS.

Hemostasis Assessment

The effect of the test article on the primary hemostasis of baboons was assessed using the standard template skin bleeding time test (Surgicutt®, International Technidyne Corp, Piscataway, NJ). All bleeding time tests were performed by the same expert technician 15 minutes after initiation of the membrane oxygenator experiment.

Radiolabeling of Platelets and Fibrinogen

For quantification of platelet deposition, autologous baboon platelets were labeled with 1 mCi of $^{111}$In, afterwards, these platelets were re-infused into the animal and allowed to circulate for at least 1 hour and up to 4 days before experiments were performed. Accumulation of platelet-associated radioactivity onto the oxygenator membrane was determined at 5-minute intervals using a GE-Brivo NM 615 interfaced with Xeleris 3.1 software (GE Healthcare, Chicago, IL).

Homologous $^{125}$I-labeled baboon fibrinogen (5-25 µg, 4 µCi, >90% clottable) was injected IV 10 minutes before each study. Incorporation of labeled fibrinogen/fibrin into the thrombus was assessed using a gamma counter (Wizard-3, PerkinElmer, Shelton, CT) at least 30 days after the experiment to allow $^{111}$In attached to platelets to decay. $^{125}$I-radioactivity deposited in the device was measured and compared to the radioactivity of clottable fibrin(ogen) in plasma samples taken during the experiment.

Platelet Deposition in the Membrane Oxygenator

Platelet deposition in the oxygenator was measured in real-time during the perfusion experiment. Radiation data was collected in 5-minute intervals by the gamma camera and the raw data of CPM measured was analyzed to calculate platelet deposition.

Fibrin(ogen) Content

At the end of the experiment, the oxygenator device with the thrombus was stored until $^{111}$In radioactivity had decayed (30+ days). At this point, the only radioactivity remaining in the graft is $^{125}$I from the labeled fibrinogen.

Results

In order to evaluate the antithrombotic efficacy of AB054, an extracorporeal membrane oxygenator interposed into an arteriovenous shunt in baboons was used to model surface-initiated thrombosis.

Figure 15A:
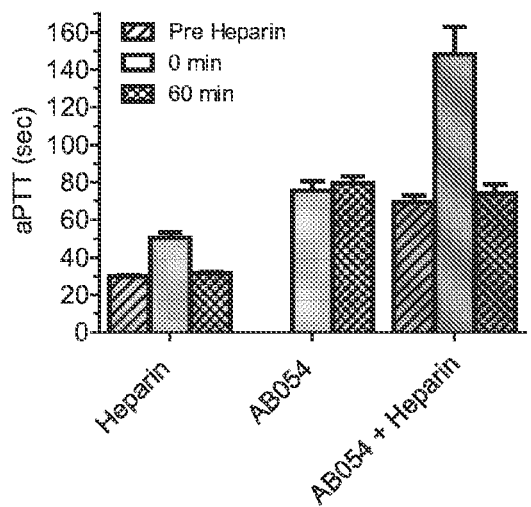
FIGS. 15A-15C: aPTT, ACT and PT measurements during membrane oxygenation perfusion experiments. Coagulation parameters including aPTT (FIG. 15A), ACT (FIG.
Figure 15B:
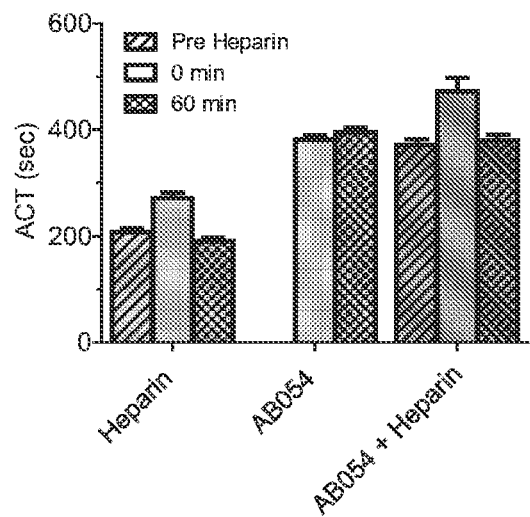
Figure 15C:
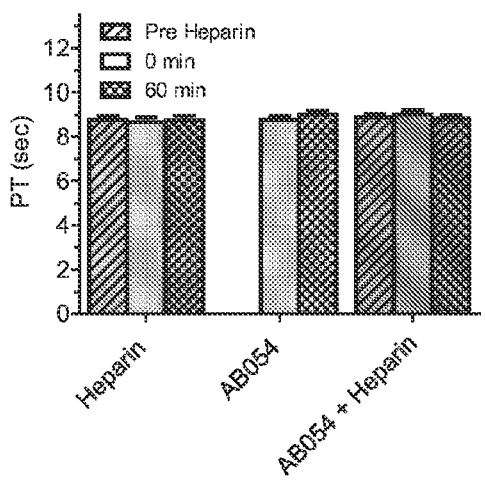

Anticoagulation during the experiment was measured using aPTT, ACT, and PT at three timepoints during the experiments (FIGS. 15A-15C). Plasma samples were taken at the beginning (0 min) and end (60 min) of the experiments. If heparin was given, plasma was also collected before heparin administration.

In each experiment, a skin template bleeding time was performed 15 minutes after the start of perfusion to evaluate hemostasis (FIGS. 16A-16C). Bleeding time, volume and rate did not appear to vary across treatments.

To measure platelet accumulation within the membrane oxygenator, blood from the femoral artery of the shunt was allowed to flow through the device for 60 minutes and returned to the animal's femoral vein. The number of platelets retained in the device and the growth rate of the thrombus was calculated (FIGS. 17A-17B). Compared to treatment with either heparin or AB054 alone, the combination of AB054 with heparin appeared to reduce platelet deposition in the oxygenator.

Terminal platelet deposition and fibrin were evaluated in all groups (FIGS. 18A-18B). Compared to treatment with either heparin or AB054 alone, the combination of AB054 with heparin reduced both platelets and fibrin accumulation measured at the end of the experiment.

Conclusions

The results of this study demonstrated that AB054 reduced platelet-dependent thrombus formation in an extracorporeal oxygenator device, without appreciable changes in the prothrombin or template bleeding times. The combination of AB054 with heparin improved the antithrombotic efficacy compared to heparin alone.

Example 7

Evaluation of the Antithrombotic Efficacy of AB054 in a Baboon Vascular Graft Thrombosis Model This example describes a study to evaluate the antithrombotic effect of AB054 in a baboon thrombosis model. Synthetic vascular graft devices were coated with either collagen or tissue factor to produce thrombogenic surfaces. The data disclosed herein demonstrate that AB054 limits collagen-initiated thrombus accumulation compared with controls, while having no antithrombotic activity when thrombi were initiated by tissue factor. These data are consistent with AB054's mechanism of action as a contact pathway inhibitor.

Introduction

Blood-contacting medical devices, including catheters, stents, and grafts can fail due to thrombus accumulation, and may also trigger device-associated thromboembolism. To maintain patency, devices that are perfused for various lengths of time require prophylactic anticoagulation that increases the incidence and/or severity of bleeding. Inhibiting the blood coagulation contact activation pathway has been proposed as an alternative approach to safer anticoagulation.

Reagents and Measurements aPTT, ACT, PT and CBC were measured as described in Example 6. Experimental grade AB054 was generated as described in Example 6.

Animals

A total of 72 vascular graft thrombosis experiments were performed in a single baboon. (FIG. 19). Experiments were performed over a 7-week period.

Treatment Groups

A total of 72 graft thrombosis experiments were performed. On 18 study days, 2 perfusion experiments with one collagen- and one tissue factor-coated graft inserted into the extended shunt loop were performed, comprising 4 graft experiments each day—2 with collagen-coated and 2 with tissue-factor coated grafts. The animal received three weekly injections of 9 mg/kg AB054 in weeks 2, 3, and 4, and experiments were performed the same day (Day 1) and the two following days—24 hours post injection (Day 2) and 48 hours post injection (Day 3). After the final injection, experiments were performed in both week 1 and week 2 of the clear out period. Each week consisted of 3 days of experiments. Saline controls were performed in week 1 and in week 7 after clear-out of the antibody. N=6 for all groups.

Vascular Graft Perfusion

Non-terminal graft perfusion experiments were performed in a juvenile male baboon (*Papio anubis*) weighing 10 kg. The baboon had a healed, surgically placed, chronic exteriorized arterio-venous (AV) shunt connecting the femoral artery and vein.

The chronic AV shunts were extended to incorporate a saline-primed ePTFE (expanded-polytetrafluoroethylene, Gore-Tex; W. L. Gore and Associates, Flagstaff, AZ) graft with a 4 mm inner diameter and 20 mm length that was either coated with equine type I collagen (Chrono-Log Corporation, Haverton, PA) or tissue factor (Dade®Innovin®, Siemens Healthcare, Marburg, Germany) for the duration of the perfusion experiment (60 minutes).

The flow of blood through the shunt in non-anticoagulated baboons consistently triggered acute thrombus formation in the collagen-coated ePTFE graft segments. During each experiment, maximum blood flow rate through the grafts (typically about 250 ml/min) was restricted by distal clamping to 100 ml/min, producing average initial wall shear rates of 265 $s^{-1}$ in 4 mm grafts. Flow rate was continuously monitored using an ultrasonic flow meter (Transonics Systems, Ithaca, NY). The 4 mm grafts did not occlude and pulsatile flow rates remained at 100 ml/min during thrombus formation. The graft segment (and thrombus) was removed from the shunt at 60 minutes and the permanent shunt was restored after each experiment. Since thrombus formation typically extends downstream from the collagen surface over time, platelet accumulation was also measured within a 10 cm-long region of the AV shunt immediately distal to the graft. In this model, thrombus growth is on the proximal collagen or tissue factor surface ("graft" thrombus), with a thrombus that propagates distal to the collagen segment (forming a thrombus "tail").

Experiments were conducted while the animal was lightly sedated and restrained in a seated position. The animal was sedated with acute ketamine sedation (10 mg/kg) or Telazol (5 mg/kg) before transport from cages to the laboratory. For transport back to the cages, the animal was mildly sedated with ketamine (1 to 2 mg/kg as needed) or Telazol (1 mg/kg).

AB054 (9 mg/kg) was administered through, and blood samples were taken from, a silicone rubber extension tubing incorporated into the AV shunt during the experiments. Complete blood counts, including red blood cell counts and hematocrit were measured daily in each animal, including before and after experiments, and calculated blood loss did not exceed 4% of the total blood volume on any experimental day.

Blood Sample Collection

Systemic blood samples (1 mL) were collected proximal to the graft devices from the midstream of the AV shunt into a ⅒th volume 3.2% citrate anticoagulant at the beginning (0 min) and end (60 min) of each experiment. An additional sample was taken prior to dosing of AB054 in weeks 3 and 4. To measure ACT, 0.2 mL whole blood was collected and analyzed immediately. To measure CBC, 0.25 mL whole blood was collected into $K_2$-EDTA coated tubes and analyzed on an Hemavet 950FS.

Hemostasis Assessment

The effect of the test article on the primary hemostasis of baboons was assessed using the standard template skin bleeding time test (Surgicutt®, International Technidyne Corp, Piscataway, NJ). All bleeding time tests were performed by the same expert technician 15 minutes after initiation of the perfusion experiment.

Graft Coating and Assembly ePTFE vascular graft material with a 4 mm inner diameter was either coated with equine type I collagen (Chrono-Log Corporation, Haverton, PA) or tissue factor (Dade®Innovin®, Siemens Healthcare, Marburg, Germany).

Radiolabeling of Platelets and Fibrinogen

For quantification of platelet deposition, autologous baboon platelets were labeled with 1 mCi of $^{111}$In, afterwards these platelets were re-infused into the animal and allowed to circulate for at least 1 hour and up to 4 days before experiments were performed. Accumulation of platelet-associated radioactivity on the graft surface and in the distal shunt segment was determined at 1-minute intervals using a GE-Brivo NM 615 interfaced with Xeleris 3.1 software (GE Healthcare, Chicago, IL). From this data, platelet accumulation over a 5-minute interval was calculated.

Homologous $^{125}$I-labeled baboon fibrinogen (5-25 µg, 4 µCi, >90% clottable) was injected IV 10 minutes before each study. Incorporation of labeled fibrinogen/fibrin into the thrombus was assessed using a gamma counter (Wizard-3, PerkinElmer, Shelton, CT) at least 30 days after the experiment to allow $^{111}$In attached to platelets to decay. $^{125}$I-radioactivity deposited in the device was measured and compared to the radioactivity of clottable fibrin(ogen) in plasma samples taken during the experiment.

Platelet Deposition in the Grafts

Platelet deposition in the grafts was measured in real time during the perfusion experiment. Radiation data was collected in 1-minute intervals by the gamma camera and the raw data of CPM measured was analyzed to calculate platelet deposition. Cumulative platelet deposition for 5-minute intervals was calculated.

Fibrin(ogen) Content

At the end of the experiment, the grafts and tail segments with the thrombus were cut out of the shunt loop and stored until $^{111}$In radioactivity had decayed (30+ days). At this point, the only radioactivity remaining in the graft was $^{125}$I from the labeled fibrinogen.

Statistical Analysis

Real-time platelet deposition of the complete thrombus for both collagen-coated and tissue factor-coated grafts was analyzed using two-way ANOVA for factors of time and treatment with Bonferroni posthoc analysis for comparison vs. control. All other measurements (aPTT, ACT, terminal platelet accumulation, terminal fibrin content, bleeding time, PT) was analyzed using one-way ANOVA with Dunnett's posthoc analysis for comparison vs. control. All analyses were performed using GraphPad Prism 5.

Results

To evaluate the antithrombotic potential of AB054 in response to thrombogenic surfaces, synthetic vascular graft devices were coated with collagen (an activator of the contact pathway) or tissue factor (an initiator of the extrinsic pathway) and these devices were deployed into an arteriovenous shunt of a baboon.

Repeat experiments were performed in a single baboon that received three weekly injections of AB054 (9 mg/kg) as outlined in FIG. 19. Anticoagulation during the experiment was measured using aPTT and ACT. Plasma samples were taken at the beginning (0 min) and end (60 min) of the perfusion experiment. The timeline in FIG. 1 shows the aPTT data from measurements taken at the beginning of each experiment over the 7-week period. FIGS. 20A-20D show the aPTT and ACT measurements at the beginning and end of each experiment grouped either by timepoint or treatment group.

During each experiment, hemostasis was assessed by PT measurements and skin template bleeding times. PT was measured using plasma samples taken at the beginning and end of the perfusion experiment (FIGS. 21A-21B). A template skin bleeding test (Surgicutt) was performed 15 minutes after start of the perfusion experiment (FIG. 22).

To assess thrombus accumulation on the thrombogenic surfaces, blood from the femoral artery of the shunt was allowed to flow through the grafts for 60 minutes. The number of platelets retained by the collagen-coated (FIGS. 23A-23D) and tissue factor-coated (FIGS. 24A-24D) grafts was measured in real-time. Analysis of the platelet accumulation in the growing thrombi was performed for both the graft and the tail portion as well as for combined total thrombus.

Terminal platelet deposition and fibrin content of the formed thrombi at 60 minutes were evaluated for both the collagen-coated (FIGS. 25A-25F) and tissue factor coated (FIGS. 26A-26F) grafts. As above, the graft and tail were evaluated separately and together. Complete blood counts were measured at the beginning and end of each experiment (FIGS. 27A-27E).

Conclusions

The results of this study demonstrated that AB054 significantly reduced thrombus development caused by blood exposure to collagen-coated vascular graft surfaces in a baboon. The antithrombotic activity of AB054 persisted for at least 2-weeks following the last dose. Consistent with AB054's mechanism of action, tissue factor-initiated thrombus development was not inhibited. No appreciable changes in the prothrombin or template bleeding times were observed.

In view of the many possible embodiments to which the principles of the disclosure may be applied, it should be recognized that the illustrated embodiments are only preferred examples of the disclosure and should not be taken as limiting the scope of the invention. Rather, the scope of the invention is defined by the following claims. We therefore claim as our invention all that comes within the scope and spirit of these claims.

---

The invention claimed is:

1. A monoclonal antibody that binds blood protein factor XII (FXII), or an antigen-binding fragment thereof, comprising a variable heavy (VH) domain and a variable light (VL) domain, wherein:
the amino acid sequence of the VH domain comprises SEQ ID NO: 8; and
the amino acid sequence of the VL domain comprises SEQ ID NO: 10.

2. The monoclonal antibody of claim 1, comprising a heavy chain and a light chain, wherein:
the amino acid sequence of the heavy chain comprises SEQ ID NO: 7; and/or
the amino acid sequence of the light chain comprises SEQ ID NO: 9.

3. The antigen-binding fragment of claim 1, wherein the antigen-binding fragment is an Fab fragment, an Fab' fragment, an F(ab)'₂ fragment, a single chain variable fragment (scFv) or a disulfide stabilized variable fragment (dsFv).

4. The monoclonal antibody or antigen-binding fragment of claim 1, which is a humanized antibody or antigen-binding fragment.

5. A fusion protein comprising the monoclonal antibody or antigen-binding fragment of claim 1 and a heterologous protein.

6. An antibody conjugate comprising the monoclonal antibody or antigen-binding fragment of claim 1 and a detectable label.

7. A composition comprising a pharmaceutically acceptable carrier and the monoclonal antibody or antigen-binding fragment of claim 1.

8. A nucleic acid molecule encoding the monoclonal antibody or antigen-binding fragment of claim 1.

9. The nucleic acid molecule of claim 8, comprising the nucleotide sequence of SEQ ID NO: 11, SEQ ID NO: 12, SEQ ID NO: 21, SEQ ID NO: 22, SEQ ID NO: 23 and/or SEQ ID NO: 24.

10. The nucleic acid molecule of claim 8, operably linked to a promoter.

11. A vector comprising the nucleic acid molecule of claim 8.

12. An isolated cell comprising the vector of claim 11.

13. A method for detecting FXII in a sample, comprising contacting the sample with the monoclonal antibody or antigen-binding fragment of claim 1; and
detecting binding of the antibody to the sample, thereby detecting FXII in the sample.

14. An in vitro method of inhibiting activation and/or activity of FXII in a sample comprising FXII, comprising contacting the sample with the antibody or antigen-binding fragment of claim 1.

15. The method of claim 14, wherein the sample comprises a blood sample.

16. A method of inhibiting activation and/or activity of FXII in a subject, treating pathologic hypercoagulation involving activation of FXII and/or activity of activated FXII (FXIIa) in a subject, or inhibiting thrombosis involving activation of FXII and/or activity of FXIIa in a subject, comprising administering to the subject an effective amount of the antibody or antigen-binding fragment of claim 1.

17. The method of claim 16, wherein the subject suffers from or is at risk of developing a bacterial infection, a fungal infection, a viral infection, a parasitic infection, an ischemic organ disease, microvascular thrombosis, macrovascular thrombosis, thromboembolism, disseminated intravascular coagulation, severe systemic inflammatory response syndrome, allergic or inflammatory reactions involving FXIIa activity, acute respiratory distress syndrome, cancer, amniotic fluid embolism, trauma, transplant rejection, sickle cell disease, autoimmune disease, or has received a medical device implantation.

18. The method of claim 17, wherein the ischemic organ disease is myocardial infarction or ischemic stroke, the cancer is a non-metastatic solid tumor cancer, a metastatic solid tumor cancer or a leukemia, or the medical device implantation is implantation of a catheter, a heart valve, a stent or a graft.

19. The method of claim 16, further comprising administering to the subject an effective amount of a second anti-coagulant therapy, or an antithrombotic or thrombolytic therapy.

20. The method of claim 16, wherein the monoclonal antibody or antigen-binding fragment is administered at a dose of about 0.1 mg/kg to about 2 g/kg.

21. A kit comprising the monoclonal antibody or antigen-binding fragment of claim 1.

* * * * *

SEQUENCE LISTING

<160> NUMBER OF SEQ ID NOS: 24

<210> SEQ ID NO 1
<211> LENGTH: 439
<212> TYPE: PRT
<213> ORGANISM: Artificial Sequence
<220> FEATURE:
<223> OTHER INFORMATION: Synthetic polypeptide

<400> SEQUENCE: 1

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Asn Leu Glu Trp
        35                  40                  45

Met Gly Tyr Ile Gln Tyr Ser Gly Asn Thr Asn Ser Asn Pro Ser Leu
    50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Glu Asp Thr Ala Thr Tyr Tyr Cys
                85                  90                  95

Ala Arg Trp Gly Ser Phe Asp Tyr Trp Gly Gln Gly Thr Thr Leu Thr
            100                 105                 110
```

Val Ser Ser Ala Lys Thr Thr Pro Pro Ser Val Tyr Pro Leu Ala Pro
            115                 120                 125

Gly Ser Ala Ala Gln Thr Asn Ser Met Val Thr Leu Gly Cys Leu Val
        130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp Cys Gly Cys Lys Pro Cys Ile Cys
210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
        275                 280                 285

Asn Ser Thr Phe Arg Ser Val Ser Glu Leu Pro Ile Met His Gln Asp
        290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
            340                 345                 350

Asp Lys Val Ser Leu Thr Cys Met Ile Thr Asp Phe Phe Pro Glu Asp
        355                 360                 365

Ile Thr Val Glu Trp Gln Trp Asn Gly Gln Pro Ala Glu Asn Tyr Lys
        370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
            420                 425                 430

Leu Ser His Ser Pro Gly Lys
            435

<210> SEQ ID NO 2
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 2

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Asn Leu Glu Trp
            35                  40                  45

Met Gly Tyr Ile Gln Tyr Ser Gly Asn Thr Asn Ser Asn Pro Ser Leu
 50                  55                  60

Lys Ser Arg Ile Ser Ile Thr Arg Asp Thr Ser Lys Asn Gln Phe Phe
 65                  70                  75                  80

Leu His Leu Asn Ser Val Thr Thr Glu Asp Thr Ala Thr Tyr Tyr Cys
                85                  90                  95

Ala Arg Trp Gly Ser Phe Asp Tyr Trp Gly Gln Gly Thr Thr Leu Thr
            100                 105                 110

Val Ser Ser
        115

<210> SEQ ID NO 3
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 3

Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Val Asn Tyr Met
            20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Gly Asn Pro Pro Thr
                85                  90                  95

Phe Gly Gly Gly Thr Ile Leu Glu Ile Lys Arg Ala Asp Ala Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
            130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
    210

<210> SEQ ID NO 4
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 4

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Gly
65                  70                  75                  80

Asp Ala Ala Thr Tyr Tyr Cys Gln Gln Trp Ser Gly Asn Pro Pro Thr
                85                  90                  95

Phe Gly Gly Gly Thr Ile Leu Glu Ile Lys
            100                 105
```

<210> SEQ ID NO 5
<211> LENGTH: 1317
<212> TYPE: DNA
<213> ORGANISM: Artificial Sequence
<220> FEATURE:
<223> OTHER INFORMATION: Synthetic nucleic acid

<400> SEQUENCE: 5

```
gatgtgcagc ttcaggagtc aggacctgac ctggtgaaac cttctcagtc actttcactc      60
acctgcactg tcactggcta ctccatcacc agtggttata ctggcactg atccggcag      120
tttccaggaa acaatctgga atggatgggc tacatacagt acagtggtaa cactaattcc     180
aacccatctc tcaaaagtcg aatctctatc actcgagaca catccaagaa ccagttcttc     240
ctgcatttga attctgtgac tactgaggac acagccacat attattgtgc aagatggggg     300
tcctttgact actggggcca aggcaccact ctcacagtct cctcagccaa acgacaccc      360
ccatctgtct atccactggc ccctggatct gctgcccaaa ctaactccat ggtgaccctg     420
ggatgcctgg tcaagggcta tttccctgag ccagtgacag tgacctggaa ctctggatcc     480
ctgtccagcg gtgtgcacac cttcccagct gtcctgcagt ctgacctcta cactctgagc     540
agctcagtga ctgtcccctc agcacctgg cccagcgaga ccgtcacctg caacgttgcc     600
cacccggcca gcagcaccaa ggtggacaag aaaattgtgc cagggattg tggttgtaag     660
ccttgcatat gtacagtccc agaggtatca tctgtcttca tcttccccc aaagcccaag     720
gatgtgctca ccattactct gactcctaag gtcacgtgtg ttgtggtaga catcagcaag     780
gatgatcccg aggtccagtt cagctggttt gtagatgatg tggaggtgca cacagctcag     840
acgcaacccc gggaggagca gttcaacagc actttccgct cagtcagtga acttcccatc     900
atgcaccagg actggctcaa tggcaaggag ttcaaatgca gggtcaacag tgcagctttc     960
cctgccccca tcgagaaaac catctccaaa accaaaggca gaccgaaggc tccacaggtg    1020
tacaccattc cacctcccaa ggagcagatg gccaaggata aagtcagtct gacctgcatg    1080
ataacagact tcttccctga agacattact gtggagtggc agtggaatgg cagccagcg    1140
gagaactaca gaacactca gcccatcatg gacacagatg gctcttactt cgtctacagc    1200
aagctcaatg tgcagaagag caactgggag gcaggaaata ctttcacctg ctctgtgtta    1260
catgagggcc tgcacaacca ccatactgag aagagcctct cccactctcc tggtaaa       1317
```

<210> SEQ ID NO 6

<211> LENGTH: 639
<212> TYPE: DNA
<213> ORGANISM: Artificial Sequence
<220> FEATURE:
<223> OTHER INFORMATION: Synthetic nucleic acid

<400> SEQUENCE: 6

```
caaattgttc tcacccagtc tccagctatc atgtctgcat ctccagggga gaaggtcacc    60
atgacctgca gtgccagctc aagtgtaaat tacatgcact ggtaccagca gaagtcaggc   120
acctccccca aaagatggat ttatgacaca tccaaactgg cttctggagt ccctgctcgc   180
ttcagtggca gtgggtctgg gacctcttac tctctcacaa tcagcagcat ggaggctgga   240
gatgctgcca cttattactg ccagcagtgg agtggtaacc caccgacgtt cggtggaggc   300
accatactgg aaatcaaacg ggctgatgct gcaccaactg tatccatctt cccaccatcc   360
agtgagcagt taacatctgg aggtgcctca gtcgtgtgct tcttgaacaa cttctacccc   420
aaagacatca atgtcaagtg gaagattgat ggcagtgaac gacaaaatgg cgtcctgaac   480
agttggactg atcaggacag caagacagc acctacagca tgagcagcac cctcacgttg   540
accaaggacg agtatgaacg acataacagc tatacctgtg aggccactca caagacatca   600
acttcaccca ttgtcaagag cttcaacagg aatgagtgt                          639
```

<210> SEQ ID NO 7
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 7

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Ile Gly Tyr Ile Gln Tyr Ser Gly Asn Thr Asn Ser Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Gly Ser Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205
```

Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
                260                 265                 270

Tyr Val Asp Gly Val Glu Val His Asn Ala Lys Thr Lys Pro Arg Glu
            275                 280                 285

Glu Gln Phe Asn Ser Thr Tyr Arg Val Val Ser Val Leu Thr Val Leu
        290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
                340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
                420                 425                 430

Gln Lys Ser Leu Ser Leu Ser Leu Gly
            435                 440

<210> SEQ ID NO 8
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 8

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
                20                  25                  30

Tyr Ser Trp His Trp Ile Arg Gln His Pro Gly Lys Gly Leu Glu Trp
            35                  40                  45

Ile Gly Tyr Ile Gln Tyr Ser Gly Asn Thr Asn Ser Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Gly Ser Phe Asp Tyr Trp Gly Gln Gly Thr Leu Val Thr
                100                 105                 110

Val Ser Ser
        115

```
<210> SEQ ID NO 9
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Asn Tyr Leu
            20                  25                  30

His Trp Tyr Gln Gln Lys Pro Gly Gln Ala Pro Arg Arg Leu Ile Tyr
        35                  40                  45

Asp Thr Ser Lys Leu Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Gly Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 10
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Asn Tyr Leu
            20                  25                  30

His Trp Tyr Gln Gln Lys Pro Gly Gln Ala Pro Arg Arg Leu Ile Tyr
        35                  40                  45

Asp Thr Ser Lys Leu Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Gly Asn Pro Pro Thr
                85                  90                  95
```

Phe Gly Gly Gly Thr Lys Val Glu Ile Lys
            100                 105

<210> SEQ ID NO 11
<211> LENGTH: 1329
<212> TYPE: DNA
<213> ORGANISM: Artificial Sequence
<220> FEATURE:
<223> OTHER INFORMATION: Synthetic nucleic acid

<400> SEQUENCE: 11

| | | | |
|---|---|---|---|
| caggtgcagc | tccaggagag | cggacccggt | ctggtgaagc ccagccagac cctgagcctg | 60 |
| acctgcaccg | tgagcggcta | ctcaatcacc | tctggctaca gctggcactg gatcaggcag | 120 |
| caccccggca | agggcctgga | gtggattggc | tatatccagt acagcggcaa caccaacagc | 180 |
| aaccccagcc | tcaagagcag | ggtgaccatc | agcagggata caagcaagaa ccagttcagc | 240 |
| ctgaagctga | gcagcgtgac | cgccgctgac | accgccgtgt actactgcgc caggtggggc | 300 |
| agcttcgact | actggggcca | gggcaccctg | gtgaccgtgt cttctgctag caccaagggc | 360 |
| cccagcgtgt | tcctctcgc  | tccctgcagc | cggagcacat ccgagagcac cgctgctctg | 420 |
| ggctgtctcg | tgaaggacta | cttccctgaa | cccgtcaccg tcagctggaa tagcggcgcc | 480 |
| ctgacatccg | gcgtccacac | attccccgct | gtcctgcaga gcagcggcct gtacagcctg | 540 |
| agctccgtgg | tcaccgtgcc | tagcagcagc | ctgggaacaa agacctacac ctgcaacgtg | 600 |
| gaccataagc | cctccaacac | caaggtggac | aagcgggtgg aatccaagta tggaccccc  | 660 |
| tgtcctcctt | gccctgctcc | tgaatttctc | ggaggcccct ccgtcttcct gtttcccccc | 720 |
| aagcccaagg | acaccctgat | gatctcccgg | acacccgaag tcacctgcgt cgtggtggat | 780 |
| gtcagccagg | aagatcccga | ggtgcagttc | aactggtacg tggacggagt ggaggtgcat | 840 |
| aacgccaaaa | ccaagcccag | ggaagagcag | ttcaacagca cctatcgggt cgtgtccgtg | 900 |
| ctcaccgtcc | tgcatcagga | ttggctcaac | ggcaaggagt acaagtgcaa ggtgtccaac | 960 |
| aagggcctgc | cctcctccat | cgagaagacc | atctccaagg ctaagggcca acctcgggag | 1020 |
| ccccaagtgt | ataccctccc | tcccagccag | gaggagatga ccaagaatca agtgagcctg | 1080 |
| acctgcctcg | tgaagggatt | ttacccctcc | gacatcgctg tggaatggga aagcaatggc | 1140 |
| caacctgaga | caactacaa  | gaccacaccc | cccgtgctgg actccgatgg ctccttcttc | 1200 |
| ctgtacagca | ggctgaccgt | ggacaaatcc | cggtggcaag agggaaacgt gttcagctgc | 1260 |
| tccgtgatgc | acgaggctct | ccacaaccac | tacacccaga gagcctctc cctgagcctc  | 1320 |
| ggctagtaa  | | | | 1329 |

<210> SEQ ID NO 12
<211> LENGTH: 642
<212> TYPE: DNA
<213> ORGANISM: Artificial Sequence
<220> FEATURE:
<223> OTHER INFORMATION: Synthetic nucleic acid

<400> SEQUENCE: 12

| | | | |
|---|---|---|---|
| gagatcgtgc | tgacccagag | cccagcaacc | ctgagcttga gccccggtga gagggccacc | 60 |
| ctgtcatgca | gggccagcag | cagcgtgaac | tacctgcact ggtatcagca gaagcccggt | 120 |
| caagcccca  | ggaggctgat | ctacgacacc | agcaagctgg ccaccggcat ccccgccagg | 180 |
| ttttccggca | gcgggtcagg | caccgactac | accctcacca taagcagcct ggagcccgag | 240 |
| gacttcgccg | tgtactactg | tcagcagtgg | agcggcaacc cacctacctt tggcggaggc | 300 |

```
actaaggtgg agatcaagcg gaccgtggcc gcccccagcg tgttcatctt ccctcccagc    360
gacgagcagc tgaagtctgg caccgccagc gtggtgtgcc tgctgaacaa cttctacccc    420
cgcgaggcca aggtgcagtg gaaggtggac aacgccctgc agagcggcaa cagccaggag    480
agcgtgaccg agcaggactc caaggacagc acctacagcc tgagcagcac cctgaccctg    540
agcaaggccg actacgagaa gcacaaggtg tacgcctgcg aggtgaccca ccagggactg    600
tctagccccg tgaccaagag cttcaaccgg ggcgagtgct aa                       642

<210> SEQ ID NO 13
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 13
```

Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Gly
            20                  25                  30

Tyr Ser Trp His Trp Ile Arg Gln His Pro Gly Lys Gly Leu Glu Trp
        35                  40                  45

Met Gly Tyr Ile Gln Tyr Ser Gly Asn Thr Asn Ser Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Gly Ser Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

```
His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
            325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440
```

<210> SEQ ID NO 14
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 14

```
Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Gly
            20                  25                  30

Tyr Ser Trp His Trp Ile Arg Gln His Pro Gly Lys Gly Leu Glu Trp
        35                  40                  45

Met Gly Tyr Ile Gln Tyr Ser Gly Asn Thr Asn Ser Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Gly Ser Phe Asp Tyr Trp Gly Gln Gly Thr Leu Val Thr
            100                 105                 110

Val Ser Ser
        115
```

<210> SEQ ID NO 15
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 15

```
Asp Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Pro Pro Gly Lys Gly Leu Glu Trp
```

```
                35                  40                  45
Ile Gly Tyr Ile Gln Tyr Ser Gly Asn Thr Asn Ser Asn Pro Ser Leu
 50                  55                  60

Lys Ser Arg Val Thr Ile Ser Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Trp Gly Ser Phe Asp Tyr Trp Gly Gln Gly Thr Met Val Thr
                100                 105                 110

Val Ser Ser Ala Ser Thr Lys Gly Pro Ser Val Phe Pro Leu Ala Pro
                115                 120                 125

Cys Ser Arg Ser Thr Ser Glu Ser Thr Ala Ala Leu Gly Cys Leu Val
                130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
                195                 200                 205

Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
                260                 265                 270

Tyr Val Asp Gly Val Glu Val His Asn Ala Lys Thr Lys Pro Arg Glu
                275                 280                 285

Glu Gln Phe Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
                340                 345                 350

Met Thr Lys Asn Gln Val Ser Leu Thr Cys Leu Val Lys Gly Phe Tyr
                355                 360                 365

Pro Ser Asp Ile Ala Val Glu Trp Glu Ser Asn Gly Gln Pro Glu Asn
                370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
                420                 425                 430

Gln Lys Ser Leu Ser Leu Ser Leu Gly
                435                 440

<210> SEQ ID NO 16
```

```
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 16

Asp Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Pro Pro Gly Lys Gly Leu Glu Trp
        35                  40                  45

Ile Gly Tyr Ile Gln Tyr Ser Gly Asn Thr Asn Ser Asn Pro Ser Leu
    50                  55                  60

Lys Ser Arg Val Thr Ile Ser Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Trp Gly Ser Phe Asp Tyr Trp Gly Gln Gly Thr Met Val Thr
            100                 105                 110

Val Ser Ser
        115

<210> SEQ ID NO 17
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Asn Tyr Leu
            20                  25                  30

His Trp Tyr Gln Gln Lys Pro Gly Gln Ala Pro Lys Arg Trp Ile Tyr
        35                  40                  45

Asp Thr Ser Lys Leu Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Gly Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

Asn Arg Gly Glu Cys
    210

<210> SEQ ID NO 18
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Asn Tyr Leu
            20                  25                  30

His Trp Tyr Gln Gln Lys Pro Gly Gln Ala Pro Lys Arg Trp Ile Tyr
        35                  40                  45

Asp Thr Ser Lys Leu Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Gly Asn Pro Pro Thr
                85                  90                  95

Phe Gly Gly Gly Thr Lys Val Glu Ile Lys
            100                 105

<210> SEQ ID NO 19
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 19

Asp Ile Val Leu Thr Gln Thr Pro Ala Thr Leu Ser Leu Ser Pro Gly
1               5                   10                  15

Glu Arg Ala Thr Leu Ser Cys Arg Ala Ser Ser Ser Val Asn Tyr Leu
            20                  25                  30

His Trp Tyr Gln Gln Lys Pro Gly Gln Ala Pro Lys Arg Leu Ile Tyr
        35                  40                  45

Asp Thr Ser Lys Leu Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Gly Asn Pro Pro Thr
                85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 20
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 20

Asp Ile Val Leu Thr Gln Thr Pro Ala Thr Leu Ser Leu Ser Pro Gly
1               5                   10                  15

Glu Arg Ala Thr Leu Ser Cys Arg Ala Ser Ser Ser Val Asn Tyr Leu
            20                  25                  30

His Trp Tyr Gln Gln Lys Pro Gly Gln Ala Pro Lys Arg Leu Ile Tyr
        35                  40                  45

Asp Thr Ser Lys Leu Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Gly Asn Pro Pro Thr
                85                  90                  95

Phe Gly Gln Gly Thr Arg Leu Glu Ile Lys
            100                 105

<210> SEQ ID NO 21
<211> LENGTH: 1329
<212> TYPE: DNA
<213> ORGANISM: Artificial Sequence
<220> FEATURE:
<223> OTHER INFORMATION: Synthetic nucleic acid

<400> SEQUENCE: 21
gacgtgcagc tccaggagag cggacccggt ctggtgaagc ccagccagac cctgagcctg      60
acctgcaccg tgaccggcta ctcaatcacc tctggctaca gctggcactg gatcaggcag     120
caccccggca agggcctgga gtggatgggc tatatccagt acagcggcaa caccaacagc     180
aaccccagcc tcaagagcag ggtgaccatc agcagggata caagcaagaa ccagttcagc     240
ctgaagctga gcagcgtgac cgccgctgac accgccgtgt actactgcgc caggtggggc     300
agcttcgact actggggcca gggcacgctg gtgaccgtgt cttctgctag caccaagggc     360
cccagcgtgt tcctctcgc tccctgcagc cggagcacat ccgagagcac cgctgctctg     420
ggctgtctcg tgaaggacta cttccctgaa cccgtcaccg tcagctggaa tagcggcgcc     480
ctgacatccg gcgtccacac attccccgct gtcctgcaga gcagcggcct gtacagcctg     540
agctccgtgg tcaccgtgcc tagcagcagc ctgggaacaa agacctacac ctgcaacgtg     600
gaccataagc cctccaacac caaggtggac aagcgggtgg aatccaagta tggacccccc     660
tgtcctcctt gccctgctcc tgaatttctc ggaggcccct ccgtcttcct gtttccccc      720 aagcccaagg acaccctgat gatctcccgg acacccgaag tcacctgcgt cgtggtggat     780
gtcagccagg aagatcccga ggtgcagttc aactggtacg tggacggagt ggaggtgcat     840
aacgccaaaa ccaagcccag ggaagagcag ttcaacagca cctatcgggt cgtgtccgtg     900

```
ctcaccgtcc tgcatcagga ttggctcaac ggcaaggagt acaagtgcaa ggtgtccaac    960
aagggcctgc cctcctccat cgagaagacc atctccaagg ctaagggcca acctcgggag   1020
ccccaagtgt ataccctccc tcccagccag gaggagatga ccaagaatca agtgagcctg   1080
acctgcctcg tgaagggatt ttaccccucc gacatcgctg tggaatggga agcaatggc    1140 caacctgaga caactacaa gaccacaccc cccgtgctgg actccgatgg ctccttcttc    1200
ctgtacagca ggctgaccgt ggacaaatcc cggtggcaag agggaaacgt gttcagctgc   1260
tccgtgatgc acgaggctct ccacaaccac tacacccaga gagcctctc cctgagcctc    1320 ggctagtaa                                                           1329
```

<210> SEQ ID NO 22
<211> LENGTH: 642
<212> TYPE: DNA
<213> ORGANISM: Artificial Sequence
<220> FEATURE:
<223> OTHER INFORMATION: Synthetic nucleic acid

<400> SEQUENCE: 22

```
gagatcgtgc tgacccagag cccagcaacc ctgagcttga gccccggtga gagggccacc     60
ctgtcatgca gggccagcag cagcgtgaac tacctgcact ggtatcagca gaagcccggt    120
caagccccca gaggtggat ctacgacacc agcaagctgg ccaccggcat ccccgccagg     180
ttttccggca gcgggtcagg caccgactac accctcacca taagcagcct ggagcccgag   240
gacttcgccg tgtactactg tcagcagtgg agcggcaacc cacctacctt tggcggaggc    300
actaaggtgg agatcaagcg gaccgtggcc gcccccagcg tgttcatctt ccctcccagc    360
gacgagcagc tgaagtctgg caccgccagc gtggtgtgcc tgctgaacaa cttctacccc    420
cgcgaggcca aggtgcagtg gaaggtggac aacgccctgc agagcggcaa cagccaggag    480
agcgtgaccg agcaggactc caaggacagc acctacagcc tgagcagcac cctgaccctg    540
agcaaggccg actacgagaa gcacaaggtg tacgcctgcg aggtgaccca ccagggactg    600
tctagccccg tgaccaagag cttcaaccgg ggcgagtgct aa                       642
```

<210> SEQ ID NO 23
<211> LENGTH: 1329
<212> TYPE: DNA
<213> ORGANISM: Artificial Sequence
<220> FEATURE:
<223> OTHER INFORMATION: Synthetic nucleic acid

<400> SEQUENCE: 23

```
gacgtgcagc tccaggagag cggacccggt ctggtgaagc ccagcgagac cctgagcctg     60
acctgcaccg tgagcggcta ctcaatcacc tctggctaca gctggcactg gatcaggcag    120
ccacccggca agggcctgga gtggattggc tatatccagt acagcggcaa caccaacagc    180 aacccccagcc tcaagagcag ggtgaccatc agcagggata caagcaagaa ccagttcagc    240
ctgaggctga gcagcgtgac cgccgctgac accgccgtgt actactgcgc caggtggggc    300
agcttcgact actggggcca gggcaccatg gtgaccgtgt cttctgctag caccaagggc    360
cccagcgtgt ttcctctcgc tccctgcagc cggagcacat ccgagagcac cgctgctctg    420
ggctgtctcg tgaaggacta cttccctgaa cccgtcaccg tcagctggaa tagcggcgcc    480
ctgacatccg gcgtccacac attccccgct gtcctgcaga gcagcggcct gtacagcctg    540
agctccgtgg tcaccgtgcc tagcagcagc ctgggaacaa agacctacac ctgcaacgtg    600
```

-continued

```
gaccataagc cctccaacac caaggtggac aagcgggtgg aatccaagta tggacccccc    660
tgtcctcctt gccctgctcc tgaatttctc ggaggcccct ccgtcttcct gtttcccccc    720
aagcccaagg acaccctgat gatctcccgg acacccgaag tcacctgcgt cgtggtggat    780
gtcagccagg aagatcccga ggtgcagttc aactggtacg tggacggagt ggaggtgcat    840
aacgccaaaa ccaagcccag ggaagagcag ttcaacagca cctatcgggt cgtgtccgtg    900
ctcaccgtcc tgcatcagga ttggctcaac ggcaaggagt acaagtgcaa ggtgtccaac    960
aagggcctgc cctcctccat cgagaagacc atctccaagg ctaagggcca acctcgggag   1020
ccccaagtgt ataccctccc tcccagccag gaggagatga ccaagaatca agtgagcctg   1080
acctgcctcg tgaagggatt ttacccctcc gacatcgctg tggaatggga aagcaatggc   1140
caacctgaga caactacaa gaccacaccc cccgtgctgg actccgatgg ctccttcttc    1200
ctgtacagca ggctgaccgt ggacaaatcc cggtggcaag agggaaacgt gttcagctgc   1260
tccgtgatgc acgaggctct ccacaaccac tacacccaga gagcctctc cctgagcctc    1320 ggctagtaa                                                            1329

<210> SEQ ID NO 24
<211> LENGTH: 642
<212> TYPE: DNA
<213> ORGANISM: Artificial Sequence
<220> FEATURE:
<223> OTHER INFORMATION: Synthetic nucleic acid

<400> SEQUENCE: 24
gacatcgtgc tgacccagac cccagcaacc ctgagcttga gccccggtga gagggccacc     60
ctgtcatgca gggccagcag cagcgtgaac tacctgcact ggtatcagca gaagcccggt    120
caagccccca agaggctgat ctacgacacc agcaagctgg ccaccggcat ccccgccagg    180
ttttccggca gcgggtcagg caccgactac accctcacca taagcagcct ggagcccgag    240
gacttcgccg tgtactactg tcagcagtgg agcggcaacc cacctacctt tggccagggc    300
actaggttgg agatcaagcg gaccgtggcc gcccccagcg tgttcatctt ccctcccagc    360
gacgagcagc tgaagtctgg caccgccagc gtggtgtgcc tgctgaacaa cttctacccc    420
cgcgaggcca aggtgcagtg gaaggtggac aacgccctgc agagcggcaa cagccaggag    480
agcgtgaccg agcaggactc caaggacagc acctacagcc tgagcagcac cctgaccctg    540
agcaaggccg actacgagaa gcacaaggtg tacgcctgcg aggtgaccca ccagggactg    600
tctagccccg tgaccaagag cttcaaccgg ggcgagtgct aa                       642
```